United States Patent
Hoge et al.

(10) Patent No.: US 10,072,057 B2
(45) Date of Patent: *Sep. 11, 2018

(54) ALTERNATIVE NUCLEIC ACID MOLECULES CONTAINING REDUCED URACIL CONTENT AND USES THEREOF

(71) Applicant: ModernaTX, Inc., Cambridge, MA (US)

(72) Inventors: Stephen G. Hoge, Brookline, MA (US); William Joseph Issa, Dedham, MA (US); Edward John Miracco, Cambridge, MA (US); Jennifer Nelson, Brookline, MA (US); John Reynders, Newton, MA (US); Matthew Stanton, Marlton, NJ (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/656,740

(22) Filed: Jul. 21, 2017

(65) Prior Publication Data

US 2018/0009866 A1   Jan. 11, 2018

Related U.S. Application Data

(63) Continuation of application No. 14/960,031, filed on Dec. 4, 2015, now Pat. No. 9,751,925, which is a continuation of application No. PCT/US2015/059112, filed on Nov. 4, 2015.

(60) Provisional application No. 62/077,871, filed on Nov. 10, 2014.

(51) Int. Cl.
| | |
|---|---|
| C07K 14/535 | (2006.01) |
| C12P 19/34 | (2006.01) |
| C07K 14/505 | (2006.01) |
| C12N 9/00 | (2006.01) |
| A61K 48/00 | (2006.01) |
| C12P 21/02 | (2006.01) |
| C12N 9/02 | (2006.01) |

(52) U.S. Cl.
CPC .......... *C07K 14/535* (2013.01); *A61K 48/005* (2013.01); *C07K 14/505* (2013.01); *C12N 9/0069* (2013.01); *C12P 19/34* (2013.01); *C12P 21/02* (2013.01); *C12Y 113/12007* (2013.01)

(58) Field of Classification Search
CPC ..... C12P 19/34; C07K 14/505; C07K 14/535; C12N 9/0069; C12Y 113/12007
See application file for complete search history.

(56) References Cited

U.S. PATENT DOCUMENTS

| | | |
|---|---|---|
| 9,334,328 B2 | 5/2016 | Schrum et al. |
| 9,428,535 B2 | 8/2016 | de Fougerolles et al. |
| 9,751,925 B2 | 9/2017 | Hoge et al. |
| 2005/0032730 A1 | 2/2005 | Von Der Mulbe et al. |
| 2007/0280929 A1 | 12/2007 | Hoerr et al. |
| 2009/0286852 A1 | 11/2009 | Kariko et al. |
| 2011/0143397 A1 | 6/2011 | Kariko et al. |
| 2011/0143436 A1 | 6/2011 | Dahl et al. |
| 2012/0237975 A1 | 9/2012 | Schrum et al. |
| 2013/0102034 A1 | 4/2013 | Schrum |
| 2013/0115272 A1 | 5/2013 | de Fougerolles et al. |
| 2013/0189741 A1 | 7/2013 | Meis et al. |
| 2016/0237134 A1 | 8/2016 | Hoge et al. |

FOREIGN PATENT DOCUMENTS

| | | |
|---|---|---|
| WO | WO 99/14346 A2 | 3/1999 |
| WO | WO 02/098443 A2 | 12/2002 |
| WO | WO 03/086280 A2 | 10/2003 |
| WO | WO 2007/024708 A2 | 3/2007 |
| WO | WO 2007/024798 A2 | 3/2007 |
| WO | WO 2008/052770 A2 | 5/2008 |
| WO | WO 2008/083949 A2 | 7/2008 |
| WO | WO 2009/046974 A2 | 4/2009 |
| WO | WO 2011/071931 A2 | 6/2011 |
| WO | WO 2011/071936 A2 | 6/2011 |
| WO | WO 2011/130624 A2 | 10/2011 |
| WO | WO 2012/045075 A1 | 4/2012 |
| WO | WO 2013/052523 A1 | 4/2013 |
| WO | WO 2013/185069 A1 | 12/2013 |
| WO | WO 2014/093924 A1 | 6/2014 |
| WO | WO 2014/160243 A1 | 10/2014 |
| WO | WO 2014/160284 A1 | 10/2014 |

OTHER PUBLICATIONS

Diebold, S.S., et al., "Nuclei acid agonists for Toll-like receptor 7 are defined by the presence of uridine ribonucleotides," *European Journal of Immunology* 36:3256-3267, Wiley-VCH Verlag GmbH & Co. KGaA, Germany (2006).

Gustafsson, C., et al., "Codon bias and heterologous protein expression," *TRENDS in Biotechnology* 22(7):346-353, Elsevier Ltd., England (2004).

Karikó, K., et al., "Suppression of RNA recognition by Toll-like receptors: the impact of nucleoside modification and the evolutionary origin of RNA," *Immunity* 23(2):165-175, Elsevier Inc., United States (2005).

Karikó, K., et al., "Incorporation of pseudouridine into mRNA yields superior nonimmunogenic vector with increased translational capacity and biological stability," *Mol Ther.* 16(11):1833-1840, The American Society of Gene Therapy, United States (2008).

(Continued)

*Primary Examiner* — Addison D Ault
(74) *Attorney, Agent, or Firm* — Clark & Elbing LLP

(57) ABSTRACT

The present disclosure provides alternative nucleosides, nucleotides, and nucleic acids, and methods of using them. In some aspects, the disclosure provides mRNA wherein the uracil content has been modified and which may be particularly effective for use in therapeutic compositions, because they may benefit from both high expression levels and limited induction of the innate immune response. In some aspects, the disclosure provides methods for the production of pharmaceutical compositions including mRNA without reverse phase chromatography.

21 Claims, 4 Drawing Sheets

Specification includes a Sequence Listing.

(56) References Cited

OTHER PUBLICATIONS

Karikó, K., et al., "Generating the optimal mRNA for therapy: HPLC purification eliminates immune activation and improves translation of nucleoside-modified, protein-encoding mRNA," *Nucleic Acids Res.* 39(21):e142, Oxford University Press, England, 10 pages (2011).
Krokan, H.E., et al., "Uracil in DNA—occurrence, consequences and repair," *Oncogene* 21(58):8935-8948, Nature Publishing Group, England (2002).
International Search Report and Written Opinion for International Application No. PCT/US2015/059112, International Searching Authority, Alexandria, VA, dated Feb. 5, 2016, 18 pages.
Non-Final Office Action dated Jan. 29, 2014 in U.S. Appl. No. 13/252,049, Schrum, et al., filed Oct. 3, 2011.
Final Office Action dated Jun. 13, 2014 in U.S. Appl. No. 13/252,049, Schrum, et al., filed Oct. 3, 2011.
Non-Final Office Action dated Dec. 4, 2014 in U.S. Appl. No. 13/644,072, de Fougerolles, et al., filed Oct. 3, 2012.
Final Office Action dated Sep. 24, 2015 in U.S. Appl. No. 13/644,072, de Fougerolles, et al., filed Oct. 3, 2012.
Non-Final Office Action dated Sep. 26, 2014 in U.S. Appl. No. 13/739,212, Schrum, et al., filed Jan. 11, 2013.
Final Office Action dated Oct. 9, 2015 in U.S. Appl. No. 13/739,212, Schrum, et al., filed Jan. 11, 2013.
Non-Final Office Action dated Aug. 7, 2013 in U.S. Appl. No. 13/897,363, Schrum, et al., filed May 18, 2013.
Final Office Action dated Nov. 14, 2013 in U.S. Appl. No. 13/897,363, Schrum, et al., filed May 18, 2013.
Non-Final Office Action dated Mar. 5, 2015 in U.S. Appl. No. 13/897,363, Schrum, et al., filed May 18, 2013.
Non-Final Office Action dated Mar. 15, 2013 in U.S. Appl. No. 13/743,518, de Fougerolles, et al., filed Jan. 17, 2013.
Final Office Action dated Aug. 30, 2013 in U.S. Appl. No. 13/743,518, de Fougerolles, et al., filed Jan. 17, 2013.
Non-Final Office Action dated Nov. 17, 2014 in U.S. Appl. No. 13/743,518, de Fougerolles, et al., filed Jan. 17, 2013.
Non-Final Office Action dated Jun. 29, 2015 in U.S. Appl. No. 13/743,518, de Fougerolles, et al., filed Jan. 17, 2013.
Final Office Action dated Feb. 17, 2016 in U.S. Appl. No. 13/743,518, de Fougerolles, et al., filed Jan. 17, 2013.
Prakash, M., "Compositional Organization of the Vertebrate Genome," in *Genomic Evolution*, pp. 70-73, Discovery Publishing House, United States (2007).
"Sequence Overview and Analysis: MUC 1 RNA sequence," 2 pages.
Non-Final Office Action dated Nov. 16, 2016 in U.S. Appl. No. 14/960,031, Hoge, et al., § 371(c) dated Dec. 4, 2015.
Final Office Action dated Feb. 16, 2017 in U.S. Appl. No. 14/960,031, Hoge, et al., § 371(c) dated Dec. 4, 2015.
Notice of Allowance dated Apr. 25, 2016 in U.S. Appl. No. 13/644,072, de Fougerolles, et al., filed Oct. 3, 2012.
Notice of Allowance dated Mar. 3, 2016 in U.S. Appl. No. 13/739,212, Schrum, et al., filed Jan. 11, 2013.
Notice of Allowance dated Jun. 8, 2017 in U.S. Appl. No. 14/960,031, Hoge, et al., § 371(c) dated Dec. 4, 2015.
Notice of Allowance dated Jun. 29, 2017 in U.S. Appl. No. 14/960,031, Hoge, et al., § 371(c) dated Dec. 4, 2015.

SEQUENCE LISTING

```
<160> NUMBER OF SEQ ID NOS: 17

<210> SEQ ID NO 1
<211> LENGTH: 10
<212> TYPE: DNA
<213> ORGANISM: Artificial Sequence
<220> FEATURE:
<223> OTHER INFORMATION: 3'-U Rich Region

<400> SEQUENCE: 1
tttttctttt                                                          10

<210> SEQ ID NO 2
<211> LENGTH: 11
<212> TYPE: DNA
<213> ORGANISM: Artificial Sequence
<220> FEATURE:
```

<223> OTHER INFORMATION: 3'-U Rich Region

<400> SEQUENCE: 2
ttttgctttt t                                                            11

<210> SEQ ID NO 3
<211> LENGTH: 10
<212> TYPE: DNA
<213> ORGANISM: Artificial Sequence
<220> FEATURE:
<223> OTHER INFORMATION: 3'-U Rich Region

<400> SEQUENCE: 3
ttttgctttt                                                              10

<210> SEQ ID NO 4
<211> LENGTH: 11
<212> TYPE: DNA
<213> ORGANISM: Artificial Sequence
<220> FEATURE:
<223> OTHER INFORMATION: 3'-A Rich Region

<400> SEQUENCE: 4
aaaaagcaaa a                                                            11

<210> SEQ ID NO 5
<211> LENGTH: 796
<212> TYPE: DNA
<213> ORGANISM: Artificial Sequence
<220> FEATURE:
<223> OTHER INFORMATION: Synthetic Construct

<400> SEQUENCE: 5
tcaagctttt ggaccctcgt acagaagcta atacgactca ctatagggaa ataagagaga        60
aagaagagt  aagaagaaat ataagagcca ccatgggagt gcacgagtgt cccgcgtggt       120
tgtggttgct gctgtcgctc ttgagcctcc cactgggact gcctgtgctg ggggcaccac       180
ccagattgat ctgcgactca cgggtacttg agaggtacct tcttgaagcc aaagaagccg       240
aaaacatcac aaccggatgc gccgagcact gctccctcaa tgagaacatt actgtaccgg       300
atacaaaggt caatttctat gcatggaaga gaatggaagt aggacagcag gccgtcgaag       360
tgtggcaggg gctcgcgctt ttgtcggagg cggtgttgcg gggtcaggcc ctcctcgtca       420
actcatcaca gccgtgggag cccctccaac ttcatgtcga taaagcggtg tcggggctcc       480
gcagcttgac gacgttgctt cgggctctgg gcgcacaaaa ggaggctatt tcgccgcctg       540
acgcggcctc cgcggcaccc ctccgaacga tcaccgcgga cacgtttagg aagcttttta       600
gagtgtacag caatttcctc cgcggaaagc tgaaattgta tactggtgaa gcgtgtagga       660
caggggatcg ctgataatag gctggagcct cggtggccat gcttcttgcc ccttgggcct       720
cccccagcc  cctcctcccc ttcctgcacc cgtaccccg  tggtctttga ataaagtctg       780
agtgggcggc tctaga                                                      796

<210> SEQ ID NO 6
<211> LENGTH: 790
<212> TYPE: DNA
<213> ORGANISM: Artificial Sequence
<220> FEATURE:
<223> OTHER INFORMATION: Synthetic Construct

<400> SEQUENCE: 6
tcaagctttt ggaccctcgt acagaagcta atacgactca ctatagggaa ataagagaga        60

```
aaagaagagt aagaagaaat ataagagcca ccatgggcgt gcacgagtgc cccgcctggc    120
tgtggctgct gctgagcctg ctgagcctgc cctgggcct gccgtgctg ggcgccccc      180 cccgcctcat ctgcgactcc cgcgtcctcg agcgctacct cctcgaggcc aaggaggccg    240
agaacatcac caccggctgc gccgagcact gctccctcaa cgagaacatc accgtccccg    300
acaccaaggt caacttctac gcctggaagc gcatggaggt cggccagcag gccgtcgagg    360
tctggcaggg cctcgccctc ctctccgagg ccgtcctccg cggccaggcc ctcctcgtca    420
actcctccca gccctgggag cccctccagc tccacgtcga caaggccgtc tccggcctcc    480
gctccctcac caccctcctc cgcgcccctcg gcgcccagaa ggaggccatc tcccccccg    540 acgccgcctc cgccgcccc ctccgcacca tcaccgccga caccttccgc aagctcttcc    600
gcgtctactc caacttcctc gcggcaagc tcaagctcta caccggcgag gcctgccgca    660
ccggcgaccg ctgataatag gctggagcct cggtggccat gcttcttgcc ccttgggcct    720 cccccagcc cctcctcccc ttcctgcacc cgtacccccg tggtctttga ataaagtctg    780
agtgggcggc                                                          790

<210> SEQ ID NO 7
<211> LENGTH: 823
<212> TYPE: DNA
<213> ORGANISM: Artificial Sequence
<220> FEATURE:
<223> OTHER INFORMATION: Synthetic Construct

<400> SEQUENCE: 7
tcaagctttt ggaccctcgt acagaagcta atacgactca ctatagggaa ataagagaga     60
aaagaagagt aagaagaaat ataagagcca ccatggccgg ccccgccacc cagagcccca    120
tgaagctgat ggccctgcag ctgctgctgt ggcacagcgc cctgtggacc gtgcaggagg    180
ccacaccttt aggacctgct tcttctttac ctcaatcttt tttattaaaa tgtttagaac    240
aagttagaaa aattcaagga gatggagctg ctttacaaga aaaattatgt gctacatata    300
aattatgtca tcctgaagaa ttagttttat taggacattc tttaggaatt ccttgggctc    360
ctttatcttc ttgtccttct caagctttac aattagctgg atgtttatct caattacatt    420
ctggattatt tttatatcaa ggattattac aagctttaga aggaatttct cctgaattag    480
gacctacatt agatacatta caattagatg ttgctgattt tgctcaaaca atttggcaac    540
aaatggaaga attaggaatg gctcctgctt tacaacctac acaaggagct atgcctgctt    600
ttgcttctgc ttttcaaaga agagctggag gagttttagt tgcttctcat ttacaatctct    660 ttttagaagt tcttatagag gttttaagac atttagctca accttgataa taggctggag    720
cctcggtggc catgcttctt gccccttggg cctcccccca gccctcctc ccttcctgc      780 acccgtaccc ccgtggtctt tgaataaagt ctgagtgggc ggc                      823

<210> SEQ ID NO 8
<211> LENGTH: 823
<212> TYPE: DNA
<213> ORGANISM: Artificial Sequence
<220> FEATURE:
<223> OTHER INFORMATION: Synthetic Construct

<400> SEQUENCE: 8
tcaagctttt ggaccctcgt acagaagcta atacgactca ctatagggaa ataagagaga     60
aaagaagagt aagaagaaat ataagagcca ccatggccgg ccccgccacc cagagcccca    120
```

| | |
|---|---|
| tgaagctgat ggccctgcag ctgctgctgt ggcacagcgc cctgtggacc gtgcaggagg | 180 |
| ccaccccct gggccccgcc agcagcctgc cccagagctt cctgctgaag tgcctggagc | 240 |
| aggtgcggaa gatccagggc gacggcgccg ccctgcagga aagctgtgc gccacctaca | 300 |
| agctgtgcca ccccgaggag ctggtgctgc tgggccacag cctgggcatc cctgggccc | 360 |
| ccctgagcag ctgccccagc caggccctgc agctggccgg ctgcctgagc cagctgcaca | 420 |
| gcggcctgtt cctgtaccag ggcctgctgc aggccctgga gggcatcagc cccgagctgg | 480 |
| gccccaccct ggacaccctg cagctggacg tggccgactt cgccaccacc atctggcagc | 540 |
| agatggagga gctgggcatg gccccgccc tgcagcccac ccagggcgcc atgcccgcct | 600 |
| tcgccagcgc cttccagcgg cgggccggcg gcgtgctggt ggccagccac ctgcagagct | 660 |
| tcctggaggt gagctaccgg gtgctgcggc acctggccca gcctgataaa taggctggag | 720 |
| cctcggtggc catgcttctt gcccttggg cctccccca gccctcctc cccttcctgc | 780 |
| acccgtaccc ccgtggtctt tgaataaagt ctgagtgggc ggc | 823 |

<210> SEQ ID NO 9
<211> LENGTH: 823
<212> TYPE: DNA
<213> ORGANISM: Artificial Sequence
<220> FEATURE:
<223> OTHER INFORMATION: Synthetic Construct

<400> SEQUENCE: 9

| | |
|---|---|
| tcaagctttt ggaccctcgt acagaagcta atacgactca ctatagggaa ataagagaga | 60 |
| aaagaagagt aagaagaaat ataagagcca ccatggccgg ccccgccacc cagagcccca | 120 |
| tgaagctgat ggccctgcag ctgctgctgt ggcacagcgc cctgtggacc gtgcaggagg | 180 |
| ccacgccgct ggggccggcg agcagcctgc cgcagagctt cctgctgaag tgcctggagc | 240 |
| aggtgaggaa gatccagggg gacggggcgg cgctgcagga aagctgtgc gcgacgtaca | 300 |
| agctgtgcca ccccggaggag ctggtgctgc tgggcacag cctggggatc ccgtgggcgc | 360 |
| cgctgagcag ctgcccgagc caggcgctgc agctggcggg gtgcctgagc cagctgcaca | 420 |
| gcgggctgtt cctgtaccag gggctgctgc aggcgctgga ggggatcagc ccggagctgg | 480 |
| ggccgacgct ggacacgctg cagctggacg tggcggactt cgcgacgacg atctggcagc | 540 |
| agatggagga gctggggatg gcgccggcgc tgcagccgac gcagggggcg atgccggcgt | 600 |
| tcgcgagcgc gttccagagg agggcggggg gggtgctggt ggcgagccac ctgcagagct | 660 |
| tcctggaggt gagctacagg gtgctgaggc acctggcgca gccgtgataa taggctggag | 720 |
| cctcggtggc catgcttctt gcccttggg cctccccca gccctcctc cccttcctgc | 780 |
| acccgtaccc ccgtggtctt tgaataaagt ctgagtgggc ggc | 823 |

<210> SEQ ID NO 10
<211> LENGTH: 823
<212> TYPE: DNA
<213> ORGANISM: Artificial Sequence
<220> FEATURE:
<223> OTHER INFORMATION: Synthetic Construct

<400> SEQUENCE: 10

| | |
|---|---|
| tcaagctttt ggaccctcgt acagaagcta atacgactca ctatagggaa ataagagaga | 60 |
| aaagaagagt aagaagaaat ataagagcca ccatggccgg ccccgccacc cagagcccca | 120 |
| tgaagctgat ggccctgcag ctgctgctgt ggcacagcgc cctgtggacc gtgcaggagg | 180 |
| ccacccccct cggccccgcc tcctcccctcc cccagtcctt cctcctcaag tgcctcgagc | 240 |

```
aggtccgcaa gatccagggc gacggcgccg ccctccagga gaagctctgc gccacctaca    300
agctctgcca ccccgaggag ctcgtcctcc tcggccactc cctcggcatc cctgggccc     360 ccctctcctc ctgcccctcc caggccctcc agctcgccgg ctgcctctcc cagctccact    420
ccggcctctt cctctaccag ggcctcctcc aggccctcga gggcatctcc cccgagctcg    480
gccccaccct cgacaccctc cagctcgacg tcgccgactt cgccaccacc atctggcagc    540
agatggagga gctcggcatg gccccgccc tccagcccac ccagggcgcc atgcccgcct     600
tcgcctccgc cttccagcgc cgcgccggcg gcgtcctcgt cgcctcccac ctccagtcct    660
tcctcgaggt ctcctaccgc gtcctccgcc acctcgccca gccctgataa taggctggag    720
cctcggtggc catgcttctt gcccttgggg cctcccccca gccctcctc ccttcctgc      780 acccgtaccc ccgtggtctt tgaataaagt ctgagtgggc ggc                      823

<210> SEQ ID NO 11
<211> LENGTH: 1861
<212> TYPE: DNA
<213> ORGANISM: Artificial Sequence
<220> FEATURE:
<223> OTHER INFORMATION: Synthetic Construct

<400> SEQUENCE: 11
tcaagctttt ggaccctcgt acagaagcta atacgactca ctatagggaa ataagagaga     60
aaagaagagt aagaagaaat ataagagcca ccatggaaga tgcgaagaac atcaagaagg    120
gacctgcccc gttttaccct ttggaggacg gtacagcagg agaacagctc acaaggcga    180 tgaaacgcta cgccctggtc cccggaacga ttgcgtttac cgatgcacat attgaggtag    240
acatcacata cgcagaatac ttcgaaatgt cggtgaggct ggcggaagcg atgaagagat    300
atggtcttaa cactaatcac cgcatcgtgg tgtgttcgga gaactcattg cagtttttca    360
tgccggtcct tggagcactt ttcatcgggg tcgcagtcgc gccagcgaac gacatctaca    420
atgagcggga actcttgaat agcatggaa tctcccagcc gacggtcgtg tttgtctcca    480 aaaagggggct gcagaaaatc ctcaacgtgc agaagaagct ccccattatt caaaagatca    540
tcattatgga tagcaagaca gattaccaag ggttccagtc gatgtatacc tttgtgacat    600
cgcatttgcc gccagggttt aacgagtatg acttcgtccc cgagtcattt gacagagata    660
aaaccatcgc gctgattatg aattcctcgg gtagcaccgg tttgccaaag ggggtggcgt    720
tgccccaccg cactgcttgt gtgcggttct cgcacgctag ggatcctatc tttggtaatc    780
agatcattcc cgacacagca atcctgtccg tggtaccttt tcatcacggt tttggcatgt    840
tcacgactct cggctatttg atttgcggtt tcagggtcgt acttatgtat cggttcgagg    900
aagaactgtt tttgagatcc ttgcaagatt acaagatcca gtcggccctc cttgtgccaa    960 cgctttctc attctttgcg aaatcgacac ttattgataa gtatgacctt tccaatctgc   1020
atgagattgc ctcaggggga cgccgctta gcaaggaagt cggggaggca gtggccaagc   1080
gcttccacct tcccggaatt cggcagggat acgggctcac ggagacaaca tccgcgatcc   1140
ttatcacgcc cgagggtgac gataagccgg gagccgtcgg aaaagtggtc cccttctttg   1200
aagccaaggt cgtagacctc gacacgggaa aaccctcgg agtgaaccag aggggcgagc    1260
tctgcgtgag agggccgatg atcatgtcag gttacgtgaa taaccctgaa gcgacgaatg   1320
cgctgatcga caaggatggg tggttgcatt cgggagacat tgcctattgg gatgaggatg   1380
agcacttctt tatcgtagat cgacttaaga gcttgatcaa atacaaaggc tatcaggtag   1440
```

```
cgcctgccga gctcgagtca atcctgctcc agcaccccaa cattttcgac gccggagtgg   1500
ccgggttgcc cgatgacgac gcgggtgagc tgccagcggc cgtggtagtc ctcgaacatg   1560
ggaaaacaat gaccgaaaag gagatcgtgg actacgtagc atcacaagtg acgactgcga   1620
agaaactgag gggaggggta gtctttgtgg acgaggtccc gaaaggcttg actgggaagc   1680
ttgacgctcg caaaatccgg gaaatcctga ttaaggcaaa gaaaggcggg aaaatcgctg   1740
tctgataata ggctggagcc tcggtggcca tgcttcttgc cccttgggcc tcccccagc    1800 ccctcctccc cttcctgcac ccgtaccccc gtggtctttg aataaagtct gagtgggcgg   1860
c                                                                   1861

<210> SEQ ID NO 12
<211> LENGTH: 1861
<212> TYPE: DNA
<213> ORGANISM: Artificial Sequence
<220> FEATURE:
<223> OTHER INFORMATION: Synthetic Construct

<400> SEQUENCE: 12
tcaagctttt ggaccctcgt acagaagcta atacgactca ctatagggaa ataagagaga     60
aaagaagagt aagaagaaat ataagagcca ccatggagga cgccaagaac atcaagaagg    120
gccccgcccc cttctacccc ctggaggacg gcaccgccgg cgagcagctg cacaaggcca    180
tgaagcggta cgccctggtg cccggcacca tcgccttcac cgacgcccac atcgaggtgg    240
acatcaccta cgccgagtac ttcgagatga gcgtgcggct ggccgaggcc atgaagcggt    300
acggcctgaa caccaaccac cggatcgtgg tgtgcagcga aaacagcctg cagttcttca    360
tgcccgtgct gggcgccctg ttcatcggcg tggccgtggc ccccgccaac gacatctaca    420
acgagcggga gctgctgaac agcatgggca tcagccagcc caccgtggtg ttcgtgagca    480
agaagggcct gcagaagatc ctgaacgtgc agaagaagct gcccatcatc cagaagatca    540
tcatcatgga cagcaagacc gactaccagg gcttccagag catgtacacc ttcgtgacca    600
gccacctgcc ccccggcttc aacgagtacg acttcgtgcc cgagagcttc gaccgggaca    660
agaccatcgc cctgatcatg aacagcgcg gcagcaccgg cctgcccaag ggcgtggccc    720
tgccccaccg gaccgcctgc gtgcggttca gccacgcccg ggaccccatc ttcggcaacc    780
agatcatccc cgacaccgcc atcctgagcg tggtgcccct tccaccacgg cttcggcatgt    840 tcaccaccct gggctacctg atctgcggct tccgggtggt gctgatgtac cggttcgagg    900
aggagctgtt cctgcggagc ctgcaggact acaagatcca gagcgccctg ctggtgccca    960
ccctgttcag cttcttcgcc aagagcaccc tgatcgacaa gtacgacctg agcaacctgc   1020
acgagatcgc cagcggcggc gcccccctga caaggaggt gggcgaggcc gtggccaagc    1080
ggttccacct gcccggcatc cggcagggct acggcctgac cgagaccacc agcgccatcc   1140
tgatcacccc cgagggcgac gacaagcccg gcgccgtggg caaggtggtg cccttcttcg   1200
aggccaaggt ggtggacctg gacaccggca agaccctggg cgtgaaccag cggggcgagc   1260
tgtgcgtgcg gggccccatg atcatgagcg gctacgtgaa caaccccgag gccaccaacg   1320
ccctgatcga caaggacggc tggctgcaca gcggcgacat cgcctactgg gacgaggacg   1380
agcacttctt catcgtggac cggctgaaga gcctgatcaa gtacaagggc taccaggtgg   1440
cccccgccga gctggagagc atcctgctgc agcaccccaa catcttcgac gccggcgtgg   1500
ccggcctgcc cgacgacgac gccggcgagc tgccgccgc cgtggtggtg ctggagcacg    1560
gcaagaccat gaccgagaag gagatcgtgg actacgtggc cagccaggtg accaccgcca   1620
```

```
agaagctgcg gggcggcgtg gtgttcgtgg acgaggtgcc caagggcctg accggcaagc    1680
tggacgcccg gaagatccgg gagatcctga tcaaggccaa gagggcggc  aagatcgccg    1740 tgtgataata ggctggagcc tcggtggcca tgcttcttgc cccttgggcc tccccccagc    1800
ccctcctccc cttcctgcac ccgtacccccgtggtctttg aataaagtct gagtgggcgg    1860
c                                                                   1861
```

<210> SEQ ID NO 13
<211> LENGTH: 1861
<212> TYPE: DNA
<213> ORGANISM: Artificial Sequence
<220> FEATURE:
<223> OTHER INFORMATION: Synthetic Construct

<400> SEQUENCE: 13

```
tcaagctttt ggaccctcgt acagaagcta atacgactca ctatagggaa ataagagaga      60
aaagaagagt aagaagaaat ataagagcca ccatggagga cgccaagaac atcaagaagg     120
gccccgcccc cttctacccc ctggaggacg gcaccgccgg cgagcagctg cacaaggcca     180
tgaagaggta cgcgctggtg ccggggacga tcgcgttcac ggacgcgcac atcgaggtgg     240
acatcacgta cgcggagtac ttcgagatga gcgtgaggct ggcggaggcg atgaagaggt     300
acgggctgaa cacgaaccac aggatcgtgg tgtgcagcga aacagcctg  cagttcttca     360 tgccggtgct gggggcgctg ttcatcgggg tggcggtggc gccggcgaac gacatctaca     420
acgagaggga gctgctgaac agcatgggga tcagccagcc gacggtggtg ttcgtgagca     480 agaagggct  gcagaagatc ctgaacgtgc agaagaagct gccgatcatc cagaagatca     540
tcatcatgga cagcaagacg gactaccagg ggttccagag catgtacacg ttcgtgacga     600
gccacctgcc gccggggttc aacgagtacg acttcgtgcc ggagagcttc gacagggaca     660 gacgatcgc gctgatcatg aacagcagcg gagcacgggg gctgccgaag ggggtggcgc     720
tgccgcacag gacggcgtgc gtgaggttca gccacgcgag ggacccgatc ttcgggaacc     780
agatcatccc ggacacggcg atcctgagcg tggtgccgtt ccaccacggg ttcgggatgt     840
tcacgacgct ggggtacctg atctgcgggt tcagggtggt gctgatgtac aggttcgagg     900
aggagctgtt cctgaggagc ctgcaggact acaagatcca gagcgcgctg ctggtgccga     960
cgctgttcag cttcttcgcg aagagcacgc tgatcgacaa gtacgacctg agcaacctgc    1020
acgagatcgc gagcgggggg gcgccgctga gcaaggaggt gggggaggcg gtggcgaaga    1080
ggttccacct gccggggatc aggcagggt  acggctgac  ggagacgacg agcgcgatcc    1140
tgatcacgcc ggaggggac  gacaagccgg ggcggtggg  gaaggtggtg ccgttcttcg    1200
aggcgaaggt ggtggacctg gacacgggga agacgctggg ggtgaaccag aggggggagc    1260
tgtgcgtgag ggggccgatg atcatgagcg gtacgtgaa  caacccggag gcgacgaacg    1320
cgctgatcga caaggacggg tggctgcaca gcggggacat cgcgtactgg gacgaggacg    1380
agcacttctt catcgtggac aggctgaaga gcctgatcaa gtacaagggg taccaggtgg    1440
cgccggcgga gctggagagc atcctgctgc agcacccgaa catcttcgac gcggggtgg    1500 cggggctgcc ggacgacgac gcgggggagc tgccggcggc ggtggtggtg ctggagcacg    1560 gaagacgat  gacggagaag gagatcgtgg actacgtggc gagccaggtg acgacggcga    1620
agaagctgag gggggggtg  gtgttcgtgg acgaggtgcc gaaggggctg acggggaagc    1680
tggacgcgag gaagatcagg gagatcctga tcaaggcgaa gaagggggg  aagatcgcgg    1740
```

```
tgtgataata ggctggagcc tcggtggcca tgcttcttgc cccttgggcc tcccccagc    1800 ccctcctccc cttcctgcac ccgtaccccc gtggtctttg aataaagtct gagtgggcgg    1860
c                                                                     1861

<210> SEQ ID NO 14
<211> LENGTH: 919
<212> TYPE: DNA
<213> ORGANISM: Artificial Sequence
<220> FEATURE:
<223> OTHER INFORMATION: Synthetic Construct

<400> SEQUENCE: 14
tcaagctttt ggaccctcgt acagaagcta atacgactca ctatagggaa ataagagaga     60
aaagaagagt aagaagaaat ataagagcca ccatggtatc caaggggggag gaggacaaca   120 tggcgatcat caaggagttc atgcgattca aggtgcacat ggaaggttcg tcaacggac    180 acgaatttga aatcgaagga gagggtgaag aaggcccta tgaagggaca cagaccgcga    240
aactcaaggt cacgaaaggg ggaccacttc ctttcgcctg gacattctt tcgcccagt     300 ttatgtacgg gtccaaagca tatgtgaagc atcccgccga tattcctgac tatctgaaac   360 tcagcttttcc cgagggattc aagtgggagc gggtcatgaa ctttgaggac ggggggtgtag  420 tcaccgtaac ccaagactca agcctccaag acggcgagtt catctacaag gtcaaactgc   480
gggggactaa ctttccgtcg gatgggccgg tgatgcagaa gaaaacgatg ggatgggaag   540
cgtcatcgga gaggatgtac ccagaagatg gtgcattgaa ggggggagatc aagcagagac  600 tgaagttgaa agatgggggga cattatgatg ccgaggtgaa aacgacatac aaagcgaaaa  660
agccggtgca gcttcccgga gcgtataatg tgaatatcaa gttggatatt acttcacaca   720
atgaggacta cacaattgtc gaacagtacg aacgcgctga gggtagacac tcgacgggag   780
gcatggacga gttgtacaaa tgataatagg ctggagcctc ggtggccatg cttcttgccc   840
cttgggcctc ccccagccc ctcctcccct tcctgcaccc gtaccccgt ggtctttgaa     900 taaagtctga gtgggcggc                                                919

<210> SEQ ID NO 15
<211> LENGTH: 919
<212> TYPE: DNA
<213> ORGANISM: Artificial Sequence
<220> FEATURE:
<223> OTHER INFORMATION: Synthetic Construct

<400> SEQUENCE: 15
tcaagctttt ggaccctcgt acagaagcta atacgactca ctatagggaa ataagagaga     60
aaagaagagt aagaagaaat ataagagcca ccatggtgag caagggcgag gaggacaaca   120
tggccatcat caaggagttc atgcggttca aggtgcacat ggagggcagc gtgaacggcc   180
acgagttcga gatcgagggc gagggcgagg ccggcccta cgagggcacc cagaccgcca    240
agctgaaggt gaccaagggc ggccccctgc ccttcgcctg gacatcctg agcccccagt    300 tcatgtacgg cagcaaggcc tacgtgaagc accccgccga catccccgac tacctgaagc   360
tgagcttccc cgagggcttc aagtgggagc gggtgatgaa cttcgaggac ggcggcgtgg   420
tgaccgtgac ccaggacagc agcctgcagg acggcgagtt catctacaag gtgaagctgc   480
ggggcaccaa cttccccagc gacggccccg tgatgcagaa gaagaccatg ggctgggagg   540
ccagcagcga gcggatgtac cccgaggacg gcgccctgaa gggcgagatc aagcagcggc   600
tgaagctgaa ggacggcggc cactacgacg ccgaggtgaa gaccacctac aaggccaaga   660
```

```
agcccgtgca gctgcccggc gcctacaacg tgaacatcaa gctggacatc accagccaca    720
acgaggacta caccatcgtg gagcagtacg agcgggccga gggccggcac agcaccggcg    780
gcatggacga gctgtacaag tgataatagg ctggagcctc ggtggccatg cttcttgccc    840
cttgggcctc cccccagccc ctcctcccct tcctgcaccc gtaccccgt ggtctttgaa     900 taaagtctga gtgggcggc                                                 919
```

<210> SEQ ID NO 16
<211> LENGTH: 919
<212> TYPE: DNA
<213> ORGANISM: Artificial Sequence
<220> FEATURE:
<223> OTHER INFORMATION: Synthetic Construct
<400> SEQUENCE: 16

```
tcaagctttt ggaccctcgt acagaagcta atacgactca ctatagggaa ataagagaga     60
aaagaagagt aagaagaaat ataagagcca ccatggtgag caagggcgag gaggacaaca    120
tggccatcat caaggagttc atgcggttca aggtgcacat ggagggcagc gtgaacggcc    180
acgagttcga gatcgagggg gagggggagg ggaggccgta cgaggggacg cagacggcga    240
agctgaaggt gacgaagggg gggccgctgc cgttcgcgtg ggacatcctg agcccgcagt    300
tcatgtacgg gagcaaggcg tacgtgaagc accggcgga catcccggac tacctgaagc    360
tgagcttccc ggaggggttc aagtgggaga gggtgatgaa cttcgaggac ggggggtgg    420 tgacggtgac gcaggacagc agcctgcagg acggggagtt catctacaag gtgaagctga    480
gggggacgaa cttcccgagc gacgggccgg tgatgcagaa gaagacgatg gggtgggagg    540
cgagcagcga gaggatgtac ccggaggacg ggcgctgaa ggggagatc aagcagaggc     600 tgaagctgaa ggacggggg cactacgacg cggaggtgaa gacgacgtac aaggcgaaga    660
agccggtgca gctgccgggg gcgtacaacg tgaacatcaa gctggacatc acgagccaca    720
acgaggacta cacgatcgtg gagcagtacg agagggcgga ggggaggcac agcacggggg    780
ggatggacga gctgtacaag tgataatagg ctggagcctc ggtggccatg cttcttgccc    840
cttgggcctc cccccagccc ctcctcccct tcctgcaccc gtaccccgt ggtctttgaa     900 taaagtctga gtgggcggc                                                 919
```

<210> SEQ ID NO 17
<211> LENGTH: 919
<212> TYPE: DNA
<213> ORGANISM: Artificial Sequence
<220> FEATURE:
<223> OTHER INFORMATION: Synthetic Construct
<400> SEQUENCE: 17

```
tcaagctttt ggaccctcgt acagaagcta atacgactca ctatagggaa ataagagaga     60
aaagaagagt aagaagaaat ataagagcca ccatggtgag caagggcgag gaggacaaca    120
tggccatcat caaggagttc atgcggttca aggtgcacat ggagggcagc gtgaacggcc    180
acgagttcga gatcgagggc gagggcgagg ccgccccta cgaggcacc cagaccgcca     240 agctcaaggt caccaagggc ggccccctcc ccttcgcctg gacatcctc tcccccagt     300 tcatgtacgg ctccaaggcc tacgtcaagc accccgccga catccccgac tacctcaagc    360
tctccttccc cgaggggcttc aagtgggagc gcgtcatgaa cttcgaggac ggcggcgtcg    420
tcaccgtcac ccaggactcc tccctccagg acggcgagtt catctacaag gtcaagctcc    480
```

```
gcggcaccaa cttcccctcc gacggccccg tcatgcagaa gaagaccatg ggctgggagg    540
cctcctccga gcgcatgtac cccgaggacg gcgccctcaa gggcgagatc aagcagcgcc    600
tcaagctcaa ggacggcggc cactacgacg ccgaggtcaa gaccacctac aaggccaaga    660
agcccgtcca gctccccggc gcctacaacg tcaacatcaa gctcgacatc acctcccaca    720
acgaggacta caccatcgtc gagcagtacg agcgcgccga gggccgccac tccaccggcg    780
gcatggacga gctctacaag tgataatagg ctggagcctc ggtggccatg cttcttgccc    840
cttgggcctc cccccagccc ctcctcccct tcctgcaccc gtaccccgt ggtctttgaa    900 taaagtctga gtgggcggc                                                 919
```

US 10,072,057 B2

ALTERNATIVE NUCLEIC ACID MOLECULES CONTAINING REDUCED URACIL CONTENT AND USES THEREOF

REFERENCE TO A SEQUENCE LISTING

This application contains a Sequence Listing in computer readable form. The computer readable form is incorporated herein by reference.

BACKGROUND OF THE INVENTION

There are multiple problems with prior methodologies of effecting protein expression. For example, heterologous DNA introduced into a cell can be inherited by daughter cells (whether or not the heterologous DNA has integrated into the chromosome) or by offspring. Introduced DNA can integrate into host cell genomic DNA at some frequency, resulting in alterations and/or damage to the host cell genomic DNA. In addition, multiple steps must occur before a protein is made. Once inside the cell, DNA must be transported into the nucleus where it is transcribed into RNA. The RNA transcribed from DNA must then enter the cytoplasm where it is translated into protein. This need for multiple processing steps creates lag times before the generation of a protein of interest. Further, it is difficult to obtain DNA expression in cells; frequently DNA enters cells but is not exprfressed or not expressed at reasonable rates or concentrations. This can be a particular problem when DNA is introduced into cells such as primary cells or modified cell lines.

Naturally occurring RNAs are synthesized from four basic ribonucleotides: ATP, CTP, UTP and GTP, but may contain post-transcriptionally modified nucleotides. Further, approximately one hundred different nucleoside alterations have been identified in RNA (Rozenski, J, Crain, P, and McCloskey, J. (1999). The RNA Modification Database: 1999 update. Nucl Acids Res 27: 196-197).

There is a need in the art for biological modalities to address the modulation of intracellular translation of nucleic acids. The present invention solves this problem by providing new mRNA molecules incorporating chemical alterations which impart properties which are advantageous to therapeutic development.

SUMMARY OF THE INVENTION

The present disclosure provides, inter alia, alternative nucleosides, alternative nucleotides, and alternative nucleic acids including an alternative nucleobase, sugar, or backbone.

In a first aspect, the invention features an mRNA encoding a polypeptide of interest and including an open reading frame, wherein (a) the uracil content of the mRNA is less than 20% of the total nucleotide content in the open reading frame; and (b) at least 90% (e.g., at least 95%, at least 99%, or 100%) of the uracils in the open reading frame are 5-methoxy-uracil. In preferred embodiments, the open reading frame consists of nucleotides including 5-methoxy-uracil and/or uracil, cytosine, adenine, and guanine.

In some embodiments, the uracil content of the mRNA is different than the uracil content of a corresponding wild-type sequence. In other embodiments, the percentage of uracil of the total nucleotide content in the open reading frame is different relative to the corresponding wild-type sequence. In certain embodiments, the percentage of uracils of the total nucleotide content in one or more subsequences (e.g., a subsequence 5 to 40 nucleotides in length) of the open reading frame is different relative to the corresponding wild-type sequence. In some embodiments, the uracil distribution within the open reading frame is different relative to the corresponding wild-type sequence. In other embodiments, the percentage of uracils of the total nucleotide content in the open reading frame is unchanged relative to the corresponding wild-type sequence. In certain embodiments, the number of uracil clusters or the size of one or more uracil clusters in the open reading frame is different relative to the corresponding wild-type sequence. In other embodiments, the distribution of uracil clusters in the open reading frame is different relative to the corresponding wild-type sequence. In certain embodiments, the distance between the uracil clusters or the location of one or more of the uracil clusters in the open reading frame is different relative to the corresponding wild-type sequence.

In some embodiments, the mRNA does not contain more than four consecutive uracils.

In some embodiments, the uracil content of the open reading frame is between a theoretical minimum and 200% of the theoretical minimum (e.g., between the theoretical minimum and 125% of the theoretical minimum, between the theoretical minimum and 150% of the theoretical minimum, or between the theoretical minimum and 175% of the theoretical minimum).

In other embodiments, the uracil content within any 20 nucleotide window within the open reading frame does not exceed 50% (e.g., does not exceed 40%, does not exceed 30%, does not exceed 20%, or does not exceed the theorectical minimum).

In certain embodiments, the guanine content of the open reading frame is maximized for at least 90% (e.g., at least 95%, at least 99%, or 100%) of the codons.

In some embodiments, the cytosine content of the open reading frame is maximized for at least 90% (e.g., at least 95%, at least 99%, or 100%) of the codons.

In another aspect, the invention provides an mRNA encoding a polypeptide of interest and including an open reading frame, wherein (a) at least 90% (e.g., at least 95%, at least 99%, or 100%) of the uracils in the open reading frame are 5-methoxy-uracil and (b) at least 50% (e.g., at least 60%, at least 70%, at least 80%, at least 90%, at least 95%, at least 99%, or 100%) of the codons in the open reading frame are guanine and/or cytosine maximized codons, wherein the open reading frame includes at least one low frequency (i.e., a codon that is not the highest frequency codon) guanine and/or cytosine maximized codon. In some embodiments, at least 50% (e.g., at least 60%, at least 70%, at least 80%, at least 90%, at least 95%, at least 99%, or 100%) of the codons in the open reading frame are guanine maximized codons, wherein the open reading frame comprises at least one low frequency guanine maximized codon. In other embodiments, at least 50% (e.g., at least 60%, at least 70%, at least 80%, at least 90%, at least 95%, at least 99%, or 100%) of the codons in the open reading frame are cytosine maximized codons, wherein the open reading frame comprises at least one low frequency cytosine maximized codon. In certain embodiments, at least 50% (e.g., at least 60%, at least 70%, at least 80%, at least 90%, at least 95%, at least 99%, or 100%) of the codons in the open reading frame are guanine and cytosine maximized codons, wherein the open reading frame comprises at least one low frequency guanine and/or cytosine maximized codon.

In another aspect, the invention features an mRNA encoding a polypeptide of interest and including an open reading frame, wherein (a) at least 90% (e.g., at least 95%, at least 99%, or 100%) of the uracils in the open reading frame are 5-methoxy-uracil and (b) the open reading frame includes at least one of the following codons: GCG, GGG, CCG, AGG, ACG, CUC, CGC, UCC, and GUC. In some embodiments, the open reading frame comprises at least one of the following codons: GCG, GGG, CCG, AGG, and ACG. In other embodiments, the open reading frame comprises at least one of the following codons: CUC, CGC, UCC, and GUC. In certain embodiments, the open reading frame comprises (i) at least one of the following codons: GCG, GGG, CCG, AGG, and ACG and (ii) at least one of the following codons CUC, CGC, UCC, and GUC.

In other embodiments of any of the foregoing mRNAs, the sequence of the mRNA has at least 55% (e.g., at least 60%, at least 65%, at least 70%, at least 75%, at least 80%, at least 85%, at least 90%, or at least 95%) identity to the corresponding wild-type sequence. In some embodiments of any of the foregoing mRNAs, the sequence of the mRNA has 60-80% (e.g., 65-75%, 60-65%, 65-70%, 70-75%, or 75-80%) identity to the corresponding wild-type sequence.

In certain embodiments of any of the foregoing mRNA, the mRNA further includes:
 (i) at least one 5'-cap structure;
 (ii) a 5'-UTR; and
 (iii) a '3'-UTR.

In some embodiments, the at least one 5'-cap structure is Cap0, Cap1, ARCA, inosine, N1-methyl-guanosine, 2'-fluoro-guanosine, 7-deaza-guanosine, 8-oxo-guanosine, 2-amino-guanosine, LNA-guanosine, or 2-azido-guanosine.

In other embodiments of any of the foregoing mRNA, the mRNA further includes a poly-A tail.

In certain embodiments of any of the foregoing mRNA, the mRNA is purified.

In another aspect, the invention features a pharmaceutical composition including any of the foregoing mRNA and a pharmaceutically acceptable excipient.

In another aspect, the invention features any of the foregoing mRNA or pharmaceutical compositions, for use in therapy.

In some embodiments of any of the foregoing mRNA, the mRA induces a detectably lower innate immune response relative to the corresponding wild-type mRNA.

In other embodiments of any of the foregoing mRNA, the mRNA exhibits enhanced ability to produce the encoded protein of interest in a mammalian cell compared to the corresponding wild-type mRNA.

In some embodiments of any of the foregoing mRNA, the mRNA exhibits increased stability. For example, in some embodiments, the mRNA exhibits increased stability in a cell into which it is introduced, relative to a corresponding wild-type mRNA. In some embodiments of any of the foregoing mRNA, the mRNA exhibits increased stability including resistance to nucleases, thermal stability, and/or increased stabilization of secondary structure. In some embodiments of any of the foregoing mRNA, increased stability exhibited by the mRNA is measured by determining the half life of the mRNA (e.g., in a plasma, cell, or tissue sample) and/or determining the area under the curve (AUC) of the protein expression by the mRNA over time (e.g., in vitro or in vivo). An mRNA is identified as having increased stability if the half life and/or the AUC is greater than the corresponding wild-type mRNA.

In some embodiments of any of the foregoing mRNA, the mRNA exhibits enhanced ability to translate or to produce the encoded protein of interest, exhibits increased stability, and/or induces a detectably lower immune response (e.g., innate or acquired) relative to a corresponding wild-type mRNA and/or an mRNA including one or more different alternative nucleic acids of the wild-type mRNA which have been altered in a different manner (e.g., an alternative nucleic acid including an alternative nucleosides other than 5-methoxy-uridine or an alternative nucleic acid for which uridine content has not been reduced) in a cell such as in a mammalian cell.

In another aspect, the invention features a method of expressing a polypeptide of interest in a mammalian cell, the method including the steps of:
 (i) providing any of the foregoing mRNA; and
 (ii) introducing the mRNA to a mammalian cell under conditions that permit the expression of the polypeptide of interest by the mammalian cell.

In another aspect, the invention features a composition including:
 a) a DNA template;
 b) an RNA polymerase;
 c) ATP, GTP, CTP, and 5-methoxy-UTP; and
 d) one or more copies of mRNA produced by the RNA polymerase, and
 e) less than 70% (e.g., less than 60%, less than 50%, less than 40%, less than 30%, less than 20%, less than 10%, less than 5%, less than 4%, less than 3%, less than 2%, less than 1%, between 0.01 and 5%, between 1% and 10%, between 5% and 20%, between 10% and 30%, between 15% and 40%, between 20% and 50%, between 30% and 60%, between 40% and 70%) of aberrant transcription products relative to full length mRNA (e.g., as measured by moles of aberrant transcription products/moles of aberrant transcription products and moles full length mRNA).

In another aspect, the invention features the use of 5-methoxy-uridine in the production of a medicament including an mRNA, wherein the production does not include reverse phase purification, e.g. wherein the reverse phase purification is not needed to remove aberrant transcription products.

In another aspect, the invention features a method of producing a pharmaceutical composition including mRNA molecules, the method including:
 a) performing in vitro synthesis to produce a composition including mRNA molecules; and
 b) determining the level of aberrant transcription products in the composition.

In another aspect, the invention features a method of producing a pharmaceutical composition including mRNA molecules, the method including:
 a) performing in vitro transcription with an RNA polymerase and a DNA template to produce a composition including mRNA molecules; and
 b) determining the level of aberrant transcription products in the composition.

In some embodiments, the method further includes c) purifying the composition if the level of aberrant transcription products in the composition is greater than a predetermined level (e.g., 70%). In some embodiments, purifying includes reverse phase chromatography.

In another aspect, the invention features a method of producing mRNA, the method includes a purification step including removal of aberrant transcription products without reverse phase chromatography including for example affinity chromatography, precipitation, and/or membrane purification such as tangential flow filtration (TFF) methods as are known in the art.

In another aspect, the invention features a method of producing a pharmaceutical composition including mRNA, the method including determining the level of mRNA including aberrant transcription products in the composition.

In another aspect, the invention features a pharmaceutical composition including mRNA, wherein the pharmaceutical composition has been determined to include less than less than 70% (e.g., less than 60%, less than 50%, less than 40%, less than 30%, less than 20%, less than 10%, less than 5%, less than 4%, less than 3%, less than 2%, less than 1%, between 0.01 and 5%, between 1% and 10%, between 5% and 20%, between 10% and 30%, between 15% and 40%, between 20% and 50%, between 30% and 60%, between 40% and 70%) aberrant transcription products relative to full length mRNA (e.g., as measured by moles of aberrant transcription products/moles of aberrant transcription products and moles full length mRNA).

In some embodiments of the foregoing compositions, uses, and methods, a composition including a lower amount of aberrant transcription products exhibits decreased immunogenicity relative to a composition including a higher amount of mRNA including aberrant transcription products. In some embodiments of the foregoing compositions, uses, and methods, the mRNA in the composition includes 5-methoxy-uridine.

In another aspect, the invention features a method of producing a pharmaceutical composition including an mRNA comprising 5-methoxy-uridine, the method including: (a) producing (e.g., directing the production of) a composition including in vitro synthesized mRNA comprising 5-methoxy-uridine; and (b) purifying (e.g., directing the purification of) the composition without reverse phase chromatography, thereby producing a pharmaceutical composition including an mRNA comprising 5-methoxy-uridine.

In some embodiments, step (a) includes in vitro transcription (e.g., with ATP, GTP, CTP, and 5-methoxy-UTP, an RNA polymerase such as T7 RNA polymerase and a DNA template such as cDNA).

In some embodiments, the method further includes (c) formulating the composition for administration. In some embodiments, step (c) includes formulating the composition in unit dosage form. In some embodiments, formulating includes includes one or more of: processing the composition into a drug product; combining the composition with a second component, e.g., an excipient and/or diluent; changing the concentration of the mRNA in the composition; lyophilizing the composition; combining a first and second aliquot of the composition to provide a third, larger, aliquot; dividing the composition into smaller aliquots; disposing the composition into a container, e.g., a gas or liquid tight container; packaging the composition; and/or associating a container including the composition with a label (e.g., labeling).

In some embodiments, the invention features a method of producing a pharmaceutical composition including an mRNA, wherein the mRNA comprises 5-methoxy-uridine, the method including: (a) providing a composition including in vitro synthesized mRNA; and (b) purifying (e.g., directing the purification of) the composition without reverse phase chromatography, thereby producing a pharmaceutical composition including mRNA.

In some embodiments, the in vitro synthesized mRNA is produced by in vitro transcription including an RNA polymerase (e.g., T7 RNA polymerase) and a DNA template (e.g., cDNA).

In some embodiments, the method further includes (c) formulating the composition for administration. In some embodiments, step (c) includes formulating the composition in unit dosage form. In some embodiments, formulating includes includes one or more of: processing the composition into a drug product; combining the composition with a second component, e.g., an excipient or diluent; changing the concentration of the mRNA in the composition; lyophilizing the composition; combining a first and second aliquot of the composition to provide a third, larger, aliquot; dividing the composition into smaller aliquots; disposing the composition into a container, e.g., a gas or liquid tight container; packaging the composition; and/or associating a container including the composition with a label (e.g., labeling).

In some embodiments, the composition exhibits decreased immunogenicity relative to a composition including an mRNA that does not comprise 5-methoxy-uridine and is produced by the same method. In some embodiments, the composition exhibits increased protein expression relative to a composition including an mRNA that does not comprise 5-methoxy-uridine and is produced by the same method. In some embodiments, the mRNA comprising 5-methoxy-uridine exhibits increased stability relative to an mRNA that does not comprise 5-methoxy-uridine and is produced by the same method. In some embodiments, the composition does not exhibit decreased immunogenicity relative to a composition including an mRNA that does not comprise 5-methoxy-uridine and is produced by a method including reverse phase purification. In some embodiments, the composition includes fewer RNA impurities resulting from aberrant transcription products (e.g., short RNAs resulting from abortive transcription, double stranded RNA resulting from RNA dependent RNA polymerase activity, and/or RNA including 3' extension region) relative to a composition including an mRNA that does not comprise 5-methoxy-uridine and is produced by the same method.

In another aspect, the invention features a pharmaceutical composition including an mRNA comprising 5-methoxy-uridine produced by performing in vitro transcription (e.g., with an RNA polymerase such as T7 RNA polymerase and a DNA template such as cDNA), to produce a composition including the mRNA and purifying the composition without reverse phase chromatography.

In some embodiments, the composition is formulated for administration. In some embodiments, the composition is formulated in unit dosage form. In some embodiments, formulating the composition includes one or more of: processing the composition into a drug product; combining the composition with a second component, e.g., an excipient or diluent; changing the concentration of the mRNA in the composition; lyophilizing the composition; combining a first and second aliquot of the composition to provide a third, larger, aliquot; dividing the composition into smaller aliquots; disposing the composition into a container, e.g., a gas or liquid tight container; packaging the composition; and/or associating a container including the composition with a label (e.g., labeling).

In some embodiments, the composition exhibits decreased immunogenicity relative to a composition including mRNA that does not comprise 5-methoxy-uridine produced with a method including purification without reverse phase chromatography. In some embodiments, the composition exhibits increased protein expression relative to a composition including mRNA that does not comprise 5-methoxy-uridine. In some embodiments, the mRNA exhibits increased stability relative to mRNA that does not comprise 5-methoxy-uridine. In some embodiments, the composition does not exhibit decreased immunogenicity relative to a composition including an mRNA that does not comprise 5-methoxy-uridine and that is purified by reverse phase chromatography. In some embodiments, the composition includes fewer RNA impurities such as aberrant transcription products (e.g., short RNAs resulting from abortive transcription, double stranded RNA resulting from RNA dependent RNA polymerase activity, and/or RNA including a 3' extension region) relative to a composition including an mRNA that does not comprise 5-methoxy-uridine and is produced with a method including purification without reverse phase chromatography.

In some embodiments of any of the foregoing methods or compositions, the aberrant transcription products include short RNAs as a result of abortive transcription initiation events. In some embodiments of any of the foregoing methods or compositions, the aberrant transcription products include double stranded (ds)RNAs generated by RNA dependent RNA polymerase activity. In some embodiments of any of the foregoing methods or compositions, the aberrant transcription products include RNA-primed transcription from RNA templates. In some embodiments of any of the foregoing methods or compositions, the aberrant transcription products include RNA comprising a self-complementary 3' extension region.

In some embodiments of any of the foregoing methods or compositions, the level of RNA impurities and/or aberrant transcription products may be determined by any method known in the art (e.g., liquid chromatography such as HPLC, UPLC, or LC-MS analysis or capillary electrophoresis).

In some embodiments of any of the foregoing methods or compositions, the mRNA comprises 5-methoxy-uridine. In some embodiments of any of the foregoing methods or compositions at least 5% (e.g., at least 10%, at least 15%, at least 20%, at least 30%, at least 40%, at least 50%, at least 60%, at least 70%, at least 80%, at least 90%, at least 95%, at least 99%, or 100%) of the uridines in the mRNA are 5-methoxy-uridine.

DETAILED DESCRIPTION OF THE INVENTION

Figure 1:
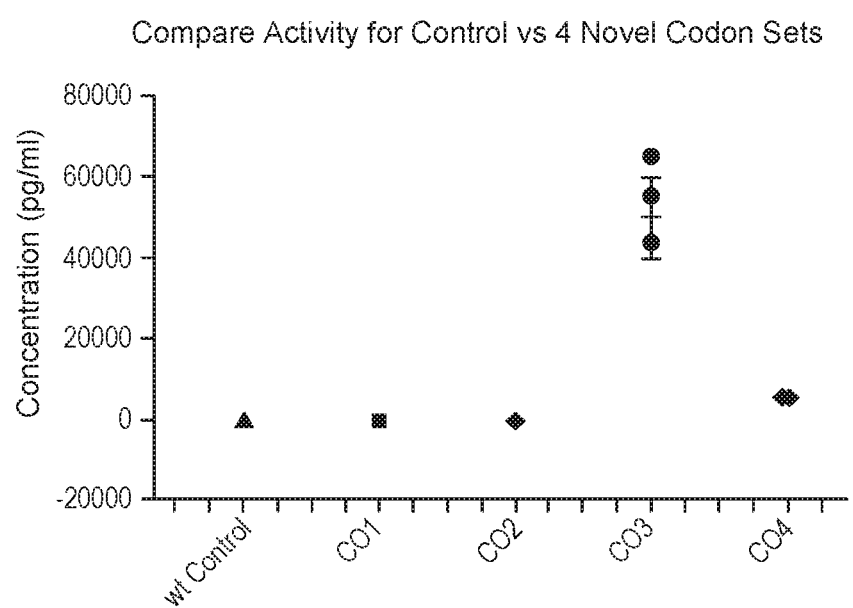
FIG. 1 is a graph of protein expression by uridine-minimized mRNA relative to the corresponding wild-type mRNA.

The present disclosure provides, inter alia, alternative nucleosides, alternative nucleotides, and alternative nucleic acids that exhibit improved therapeutic properties including, but not limited to, increased expression and/or a reduced innate immune response when introduced into a population of cells.

As there remains a need in the art for therapeutic modalities to address the myriad barriers surrounding the efficacious modulation of intracellular translation and processing of nucleic acids encoding polypeptides or fragments thereof, the inventors have shown that certain alternative mRNA sequences have the potential as therapeutics with benefits beyond just evading, avoiding or diminishing the immune response.

The present invention addresses this need by providing nucleic acid based compounds or polynucleotides (e.g., alternative mRNAs) which encode a polypeptide of interest and which have structural and/or chemical features that avoid one or more of the problems in the art, for example, features which are useful for optimizing nucleic acid-based therapeutics while retaining structural and functional integrity, overcoming the threshold of expression, improving expression rates, half life and/or protein concentrations, optimizing protein localization, and avoiding deleterious bio-responses such as the immune response and/or degradation pathways.

In particular, the inventors have identified that mRNA wherein the uracil content has been modified may be particularly effective for use in therapeutic compositions, because they may benefit from both high expression levels and limited induction of the innate immune response, as shown in the Examples (in particular, high performance may be observed across the assays in Examples 6-9). In the invention, a percentage of the uracils in the open reading frame (and optionally other components of an mRNA) are 5-methoxy-uracil. Preferaby, at least 90%, e.g., at least 95% or 100%, of the uracils are 5-methoxy-uracil. Thus, as is apparent from the context, the term uracils can refer to 5-methoxy-uracil and naturally occurring uracil.

Polypeptides of interest, according to the present invention, may be selected from any of those disclosed in US 2013/0259924, US 2013/0259923, WO 2013/151663, WO 2013/151669, WO 2013/151670, WO 2013/151664, WO 2013/151665, WO 2013/151736, U.S. Provisional Patent Application No. 61/618,862, U.S. Provisional Patent Application No. 61/681,645, U.S. Provisional Patent Application No. 61/618,873, U.S. Provisional Patent Application No. 61/681,650, U.S. Provisional Patent Application No. 61/618,878, U.S. Provisional Patent Application No. 61/681,654, U.S. Provisional Patent Application No. 61/618,885, U.S. Provisional Patent Application No. 61/681,658, U.S. Provisional Patent Application No. 61/618,911, U.S. Provisional Patent Application No. 61/681,667, U.S. Provisional Patent Application No. 61/618,922, U.S. Provisional Patent Application No. 61/681,675, U.S. Provisional Patent Application No. 61/618,935, U.S. Provisional Patent Application No. 61/681,687, U.S. Provisional Patent Application No. 61/618,945, U.S. Provisional Patent Application No. 61/681,696, U.S. Provisional Patent Application No. 61/618,953, and U.S. Provisional Patent Application No. 61/681,704, the polypeptides of each of which are incorporated herein by reference.

Provided herein, in part, are polynucleotides encoding polypeptides of interest which have been chemically modified to improve one or more of the stability and/or clearance in tissues, receptor uptake and/or kinetics, cellular access by the compositions, engagement with translational machinery, mRNA half-life, translation efficiency, immune evasion, protein production capacity, secretion efficiency (when applicable), accessibility to circulation, protein half-life and/or modulation of a cell's status, function and/or activity.

The alternative polynucleotides of the invention, including the combination of alterations taught herein, have superior properties making them more suitable as therapeutic modalities.

In one aspect of the invention, methods of determining the effectiveness of an alternative mRNA as compared to wild-type involves the measure and analysis of one or more cytokines whose expression is triggered by the administration of the exogenous nucleic acid of the invention. These values are compared to administration of an unaltered nucleic acid or to a standard metric such as cytokine response, PolyIC, R-848 or other standard known in the art.

One example of a standard metric herein is the measure of the ratio of the level or amount of encoded polypeptide (protein) produced in the cell, tissue or organism to the level or amount of one or more (or a panel) of cytokines whose expression is triggered in the cell, tissue or organism as a result of administration or contact with the alternative nucleic acid. Such ratios are referred to herein as the Protein:Cytokine Ratio or "PC" Ratio. The higher the PC ratio, the more efficacious the alternative nucleic acid (polynucleotide encoding the protein measured). Preferred PC Ratios, by cytokine, of the present invention may be greater than 1, greater than 10, greater than 100, greater than 1000, greater than 10,000 or more. Alternative nucleic acids having higher PC Ratios than an alternative nucleic acid of a different or unaltered construct are preferred.

The PC ratio may be further qualified by the percent alteration present in the polynucleotide. For example, normalized to a 100% alternative nucleic acid, the protein production as a function of cytokine (or risk) or cytokine profile can be determined.

Preferably, the alternative mRNAs are substantially non toxic and non mutagenic.

The compositions and methods described herein can be used, in vivo and in vitro, both extracellularly and intracellularly, as well as in assays such as cell free assays.

In another aspect, the present disclosure provides chemical alterations located on the sugar moiety of the nucleotide.

In another aspect, the present disclosure provides chemical alterations located on the phosphate backbone of the nucleic acid.

In another aspect, the present disclosure provides nucleotides that contain chemical alterations, wherein the nucleotide reduces the cellular innate immune response, as compared to the cellular innate immune induced by a corresponding unaltered nucleic acid.

In another aspect, the present disclosure provides compositions comprising a compound as described herein. In some embodiments, the composition is a reaction mixture. In some embodiments, the composition is a pharmaceutical composition. In some embodiments, the composition is a cell culture. In some embodiments, the composition further comprises an RNA polymerase and a cDNA template. In some embodiments, the composition further comprises a nucleotide having a nucleobase selected from the group consisting of adenine, cytosine, guanine, 5-methoxy-uracil and/or uracil.

In a further aspect, the present disclosure provides methods of making a pharmaceutical formulation comprising a physiologically active secreted protein, comprising transfecting a first population of human cells with the pharmaceutical nucleic acid made by the methods described herein, wherein the secreted protein is active upon a second population of human cells.

In some embodiments, the secreted protein is capable of interacting with a receptor on the surface of at least one cell present in the second population.

In certain embodiments, provided herein are combination therapeutics containing one or more alternative nucleic acids containing translatable regions that encode for a protein or proteins that boost a mammalian subject's immunity along with a protein that induces antibody-dependent cellular toxicity.

In one embodiment, it is intended that the compounds of the present disclosure are stable. It is further appreciated that certain features of the present disclosure, which are, for clarity, described in the context of separate embodiments, can also be provided in combination in a single embodiment. Conversely, various features of the present disclosure which are, for brevity, described in the context of a single embodiment, can also be provided separately or in any suitable subcombination.

Uracil Content

The present disclosure provides nucleic acids wherein with altered uracil content at least one codon in the wild-type sequence has been replaced with an alternative codon to generate a uracil-altered sequence. Altered uracil sequences can have at least one of the following properties:

(i) an increase or decrease in global uracil content (i.e., the percentage of uracil of the total nucleotide content in the nucleic acid of a section of the nucleic acid, e.g., the open reading frame); or, (ii) an increase or decrease in local uracil content (i.e., changes in uracil content are limited to specific subsequences); or, (iii) a change in uracil distribution without a change in the global uracil content; or, (iv) a change in uracil clustering (e.g., number of clusters, location of clusters, or distance between clusters); or, (v) combinations thereof.

In some aspects, the percentage of uracil nucleobases in the nucleic acid sequence is reduced with respect to the percentage of uracil nucleobases in the wild-type nucleic acid sequence. For example, 30% of nucleobases may be uracils in the wild-type sequence and 10% in the nucleic acid sequence of the invention. The percentage uracil content can be determined by dividing the number of uracils in a sequence by the total number of nucleotides and multiplying by 100.

In other aspects, the percentage of uracil nucleobases in a subsequence of the nucleic acid sequence is reduced with respect to the percentage of uracil nucleobases in the corresponding subsequence of the wild-type sequence. For example, the wild-type sequence may have a 5'-end region (e.g., 30 codons) with a local uracil content of 30%, and the uracil content in that same region could be reduced to 10% in the nucleic acid sequence of the invention.

In specific aspects, codons in the nucleic acid sequence of the invention reduce or modify, for example, the number, size, location, or distribution of uracil clusters that could have deleterious effects on protein translation. Although as a general rule lower uracil content is desirable, in certain aspects, the uracil content, and in particular the local uracil content, of some subsequences of the wild-type sequence can be greater than the wild-type sequence and still maintain beneficial features (e.g., increased expression).

In some aspects, the uracil-modified sequence induces a lower Toll-Like Receptor (TLR) response when compared to the wild-type sequence. Several TLRs recognize and respond to nucleic acids. Double-stranded (ds)RNA, a frequent viral constituent, has been shown to activate TLR3. See Alexopoulou et al. (2001) Nature, 413:732-738 and Wang et al. (2004) Nat. Med., 10:1366-1373. Single-stranded (ss)RNA activates TLR7. See Diebold et al. (2004) Science 303:1529-1531. RNA oligonucleotides, for example RNA with phosphorothioate internucleotide linkages, are ligands of human TLR8. See Heil et al. (2004) Science 303:1526-1529. DNA containing unmethylated CpG motifs, characteristic of bacterial and viral DNA, activate TLR9. See Hemmi et al. (2000) Nature, 408: 740-745. See also, Kariko et al. (2005) Immunity 23:165-175, which is herein incorporated by reference in its entirety.

As used herein, the term "TLR response" is defined as the recognition of single-stranded RNA by a TLR7 receptor, and in some aspects encompasses the degradation of the RNA and/or physiological responses caused by the recognition of the single-stranded RNA by the receptor. Methods to determine and quantify the binding of an RNA to a TLR7 are known in the art. Similarly, methods to determine whether an RNA has triggered a TLR7-mediated physiological response (e.g., cytokine secretion) are well known in the art. In some aspects, a TLR response can be mediated by TLR3, TLR8, or TLR9 instead of TLR7.

Suppression of TLR7-mediated response can be accomplished via nucleoside modification. RNA undergoes over a hundred different nucleoside modifications in nature (see the RNA Modification Database, available at mods.rna.albany.edu). Human rRNA, for example, has ten times more pseudouracil (ψ) and 25 times more 2'-O-methylated nucleosides than bacterial rRNA. Bacterial mRNA contains no nucleoside modifications, whereas mammalian mRNAs have modified nucleosides such as 5-methylcytidine (m5C), N6-methyladenosine (m6A), inosine and many 2'-O-methylated nucleosides in addition to N7-methylguanosine (m7G).

Uracil and ribose, the two defining features of RNA, are both necessary and sufficient for TLR7 stimulation, and short single-stranded RNA (ssRNA) act as TLR7 agonists in a sequence-independent manner as long as they contain several uracils in close proximity. See Diebold et al. (2006) Eur. J. Immunol. 36:3256-3267, which is herein incorporated by reference in its entirety. Accordingly, a nucleic acid sequence of the invention may have reduced uracil content (locally and/or locally) and/or reduced or altered uracil clustering to reduce or to suppress a TLR7-mediated response.

In some aspects, the TLR response (e.g., a response mediated by TLR7) caused by the uracil-modified sequence is at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least 100% lower than the TLR response caused by the wild-type nucleic acid sequence.

In some aspects, the TLR response caused by the wild-type nucleic acid is at least about 1-fold, at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 3-fold, at least about 4-fold, at least about 5-fold, at least about 6-fold, at least about 7-fold, at least about 8-fold, at least about 9-fold, or at least about 10-fold higher than the TLR response caused by the uracil-modified sequence.

In other aspects, the uracil content of the uracil-altered sequence is lower than the uracil content of the wild-type nucleic acid sequence. Accordingly, in some aspects, the sequence of the invention contains at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% less uracil than the wild-type nucleic acid sequence.

In some aspects, the uracil content is less than 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6% 5%, 4%, 3%, 2% or 1% of the total nucleobases in the sequence of the invention. In some aspects, the uracil content of the sequence of the invention is between about 5% and about 25%. In some particular aspects, the uracil content of the sequence of the invention is between about 15% and about 25%.

In some aspects, the uracil content of the wild-type nucleic acid sequence can be measured using a sliding window. In some aspects, the length of the sliding window is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleobases. In some aspects, the sliding window is over 40 nucleobases in length. In a preferred aspect, the sliding window is 20 nucleobases in length. Based on the uracil content measured with a sliding window, it is possible to generate a histogram representing the uracil content throughout the length of the wild-type nucleic acid sequence and nucleic acid sequence of the invention. In some aspects, the nucleic acid sequence of the invention has fewer peaks in the representation that are above a certain percentage value relative to the candidate sequence. In some aspects, the nucleic acid sequence of the invention does not have peaks in the sliding-window representation which are above 65%, 60%, 55%, 50%, 45%, 40%, 35%, or 30% uracil. In a preferred aspect, the nucleic acid sequence of the invention has no peaks over 30% uracil, as measured using a 20 nucleobase sliding window. In some aspects, the nucleic acid sequence of the invention has no more than a predetermined number of peaks, as measured using a 20 nucleobase sliding window, above a certain threshold value. For example, in some aspects, the nucleic acid sequence of the invention has no peaks or no more than 1, 2, 3, 4, 5, 6, 7, 8, 9 or 10 peaks in the above 10%, 15%, 20%, 25% or 30% uracil. In a preferred aspect, the nucleic acid sequence of the invention contains between 0 peaks and 2 peaks with uracil content 30% or higher.

In some aspects, the nucleic acid sequence has reduced consecutive uracils. For example, two consecutive leucines could be encoded by the sequence CUUUUG, which would include a four uracil cluster. Such a subsequence could be substituted with CUGCUC, which would effectively remove the uracil cluster. Accordingly, a nucleic sequence may have reduced or no uracil pairs (UU), uracil triplets (UUU) or uracil quadruplets (UUUU), relative to the wild-type nucleic acid sequence. In some aspects, the nucleic acid sequence does not include uracil pairs (UU) and/or uracil triplets (UUU) and/or uracil quadruplets (UUUU). In other aspects, the nucleic acid sequence does not include uracil pairs (UU) and/or uracil triplets (UUU) and/or uracil quadruplets (UUUU) above a certain threshold, e.g., no more than 1, 2, 3, 4, 5, 6, 7, 8, 9, or 10 occurrences in the nucleic acid sequence. In a particular aspect, the nucleic acid sequence contains fewer than 5, 4, 3, 2, or 1 uracil pairs. In another particular aspect, the nucleic acid sequence contains no uracil pairs.

In some aspects, the wild-type nucleic acid sequence can comprise uracil clusters which due to their number, size, location, distribution or combinations thereof have negative effects on translation. As used herein, the term "uracil cluster" refers to a subsequence in a nucleic acid sequence that contains a uracil content (usually described as a percentage) which is above a certain threshold. Thus, in certain aspects, if a subsequence comprises more than 10%, 15%, 20%, 25%, 30%, 35%, 40%, 45%, 50%, 55%, 60% or 65% uracil content, such subsequence would be considered a uracil cluster.

The negative effects of uracil clusters can be, for example, eliciting a TLR7 response. Thus, in some embodiments, the nucleic acid of the invention has a reduced number of clusters, size of clusters, location of clusters (e.g., close to the 5' and/or 3' end of a nucleic acid sequence), distance between clusters, or distribution of uracil clusters (e.g., a certain pattern of clusters along a nucleic acid sequence, distribution of clusters with respect to secondary structure elements in the expressed product, or distribution of clusters with respect to the secondary structure of an mRNA) relative to wild-type.

In some aspects, the wild-type sequence comprises at least one uracil cluster, wherein said uracil cluster is a subsequence of the wild-type nucleic acid sequence wherein the percentage of total uracil nucleobases in said subsequence is above a predetermined threshold. In some aspects, the length of the subsequence is at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 nucleobases. In some aspects, the subsequence is longer than 100 nucleobases. In some aspects, the threshold is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% uracil content. In some aspects, the threshold is above 25%.

For example, an amino acid sequence such as ADGSR could be encoded by the nucleic acid sequence GCU GAU GGU AGU CGU. Although such a sequence does not contain any uracil pairs, triplets, or quadruplets, one third of the nucleobases would be uracils. Such a uracil cluster could be removed by using alternative codons, for example, by using the coding sequence GCC GAC GGC AGC CGC, which would contain no uracils.

In other aspects, the wild-type sequence comprises at least one uracil cluster, wherein said uracil cluster is a subsequence of the wild-type nucleic acid sequence wherein the percentage of uracil nucleobases of said subsequence as measured using a sliding window is above a predetermined threshold. In some aspects, the length of the sliding window is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleobases. In some aspects, the sliding window is over 40 nucleobases in length. In some aspects, the threshold is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% uracil content. In some aspects, the threshold is above 25%.

In some aspects, the wild-type nucleic acid sequence comprises at least two uracil clusters. In some aspects, the sequence of the invention contains fewer uracil-rich clusters than the wild-type nucleic acid sequence. In some aspects, the sequence of the invention contains more uracil-rich clusters than the wild-type nucleic acid sequence. In some aspects, the sequence of the invention contains uracil-rich clusters which are shorter in length than corresponding uracil-rich clusters in the wilde type nucleic acid sequence. In other aspects, the sequence of the invention contains uracil-rich clusters which are longer in length that corresponding uracil-rich cluster in the wild-type nucleic acid sequence.

Alternative Nucleotides, Nucleosides and Polynucleotides of the Invention

Herein, in a nucleotide, nucleoside or polynucleotide (such as the nucleic acids of the invention, e.g., mRNA molecule), the terms "alteration" or, as appropriate, "alternative" refer to alteration with respect to A, G, U or C ribonucleotides. Generally, herein, these terms are not intended to refer to the ribonucleotide alterations in naturally occurring 5'-terminal mRNA cap moieties. In a polypeptide, the term "alteration" refers to an alteration as compared to the canonical set of 20 amino acids, moiety)

The alterations may be various distinct alterations. In some embodiments, where the nucleic acid is an mRNA, the coding region, the flanking regions and/or the terminal regions may contain one, two, or more (optionally different) nucleoside or nucleotide alterations. In some embodiments, an alternative polynucleotide introduced to a cell may exhibit reduced degradation in the cell, as compared to an unaltered polynucleotide.

The polynucleotides can include any useful alteration, such as to the sugar or the internucleoside linkage (e.g., to a linking phosphate/to a phosphodiester linkage/to the phosphodiester backbone). In certain embodiments, alterations (e.g., one or more alterations) are present in each of the sugar and the internucleoside linkage. Alterations according to the present invention may be alterations of ribonucleic acids (RNAs) to deoxyribonucleic acids (DNAs), e.g., the substitution of the 2'OH of the ribofuranosyl ring to 2'H, threose nucleic acids (TNAs), glycol nucleic acids (GNAs), peptide nucleic acids (PNAs), locked nucleic acids (LNAs) or hybrids thereof). Additional alterations are described herein.

As described herein, the polynucleotides of the invention do not substantially induce an innate immune response of a cell into which the polynucleotide (e.g., mRNA) is introduced. Features of an induced innate immune response include 1) increased expression of pro-inflammatory cytokines, 2) activation of intracellular PRRs (RIG-I, MDAS, etc), and/or 3) termination or reduction in protein translation.

In certain embodiments, it may desirable for an alternative nucleic acid molecule introduced into the cell to be degraded intracellularly. For example, degradation of an alternative nucleic acid molecule may be preferable if precise timing of protein production is desired. Thus, in some embodiments, the invention provides an alternative nucleic acid molecule containing a degradation domain, which is capable of being acted on in a directed manner within a cell.

The polynucleotides can optionally include other agents (e.g., RNAi-inducing agents, RNAi agents, siRNAs, shRNAs, miRNAs, antisense RNAs, ribozymes, catalytic DNA, tRNA, RNAs that induce triple helix formation, aptamers, vectors, etc.). In some embodiments, the polynucleotides may include one or more messenger RNAs (mRNAs) having one or more alternative nucleoside or nucleotides (i.e., alternative mRNA molecules). Details for these polynucleotides follow.

Polynucleotides

The polynucleotides of the invention typically include a first region of linked nucleosides encoding a polypeptide of interest, a first flanking region located at the 5' terminus of the first region, and a second flanking region located at the 3' terminus of the first region.

Alterations on the Sugar

The alternative nucleosides and nucleotides, which may be incorporated into a polynucleotide (e.g., RNA or mRNA, as described herein), can be altered on the sugar of the ribonucleic acid. For example, the 2' hydroxyl group (OH)

can be modified or replaced with a number of different substituents. Exemplary substitutions at the 2'-position include, but are not limited to, H, halo, optionally substituted $C_{1-6}$ alkyl; optionally substituted $C_{1-6}$ alkoxy; optionally substituted $C_{6-10}$ aryloxy; optionally substituted $C_{3-8}$ cycloalkyl; optionally substituted $C_{3-8}$ cycloalkoxy; optionally substituted $C_{6-10}$ aryloxy; optionally substituted $C_{6-10}$ aryl-$C_{1-6}$ alkoxy, optionally substituted $C_{1-12}$ (heterocyclyl) oxy; a sugar (e.g., ribose, pentose, or any described herein); a polyethyleneglycol (PEG), —O(CH$_2$CH$_2$O)$_n$CH$_2$CH$_2$OR, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxyl is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl; aminoalkoxy; amino; and amino acid.

Generally, RNA includes the sugar group ribose, which is a 5-membered ring having an oxygen. Exemplary, non-limiting alternative nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as anhydrohexitol, altritol, mannitol, cyclohexanyl, cyclohexenyl, and morpholino that also has a phosphoramidate backbone); multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar.

Alterations on the Internucleoside Linkage

The alternative nucleotides, which may be incorporated into a polynucleotide molecule, can be altered on the internucleoside linkage (e.g., phosphate backbone). Herein, in the context of the polynucleotide backbone, the phrases "phosphate" and "phosphodiester" are used interchangeably. Backbone phosphate groups can be altered by replacing one or more of the oxygen atoms with a different substituent.

The alternative nucleosides and nucleotides can include the wholesale replacement of an unaltered phosphate moiety with another internucleoside linkage as described herein. Examples of alternative phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be altered by the replacement of a linking oxygen with nitrogen (bridged phosphoramidates), sulfur (bridged phosphorothioates), and carbon (bridged methylene-phosphonates).

The alternative nucleosides and nucleotides can include the replacement of one or more of the non-bridging oxygens with a borane moiety (BH$_3$), sulfur (thio), methyl, ethyl and/or methoxy. As a non-limiting example, two non-bridging oxygens at the same position (e.g., the alpha (α), beta (β) or gamma (γ) position) can be replaced with a sulfur (thio) and a methoxy.

The replacement of one or more of the oxygen atoms at the α position of the phosphate moiety (e.g., α-thio phosphate) is provided to confer stability (such as against exonucleases and endonucleases) to RNA and DNA through the unnatural phosphorothioate backbone linkages. Phosphorothioate DNA and RNA have increased nuclease resistance and subsequently a longer half-life in a cellular environment. While not wishing to be bound by theory, phosphorothioate linked polynucleotide molecules are expected to also reduce the innate immune response through weaker binding/activation of cellular innate immune molecules.

Other internucleoside linkages that may be employed according to the present invention, including internucleoside linkages which do not contain a phosphorous atom, are described herein below.

Synthesis of Polynucleotide Molecules

The polynucleotide molecules for use in accordance with the invention may be prepared according to any useful technique, as described herein. The alternative nucleosides and nucleotides used in the synthesis of polynucleotide molecules disclosed herein can be prepared from readily available starting materials using the following general methods and procedures. Where typical or preferred process conditions (e.g., reaction temperatures, times, mole ratios of reactants, solvents, pressures, etc.) are provided, a skilled artisan would be able to optimize and develop additional process conditions. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Preparation of polynucleotide molecules of the present invention can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 2d. Ed., Wiley & Sons, 1991, which is incorporated herein by reference in its entirety.

The reactions of the processes described herein can be carried out in suitable solvents, which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of alternative polynucleotides or nucleic acids (e.g., polynucleotides or alternative mRNA molecules) can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

Alternative nucleosides and nucleotides (e.g., building block molecules) can be prepared according to the synthetic methods described in Ogata et al., J. Org. Chem. 74:2585-2588 (2009); Purmal et al., Nucl. Acids Res. 22(1): 72-78, (1994); Fukuhara et al., Biochemistry, 1(4): 563-568 (1962); and Xu et al., Tetrahedron, 48(9): 1729-1740 (1992), each of which are incorporated by reference in their entirety.

The polynucleotides of the invention may or may not be uniformly altered along the entire length of the molecule. For example, one or more or all types of nucleotide (e.g., purine or pyrimidine, or any one or more or all of A, G, U, C) may or may not be uniformly altered in a polynucleotide of the invention, or in a given predetermined sequence region thereof. In some embodiments, all nucleotides X in a polynucleotide of the invention (or in a given sequence region thereof) are altered, wherein X may any one of nucleotides A, G, U, C, or any one of the combinations A+G, A+U, A+C, G+U, G+C, U+C, A+G+U, A+G+C, G+U+C or A+G+C.

Different sugar alterations and/or internucleoside linkages (e.g., backbone structures) may exist at various positions in the polynucleotide. One of ordinary skill in the art will appreciate that the nucleotide analogs or other alteration(s) may be located at any position(s) of a polynucleotide such that the function of the polynucleotide is not substantially decreased. An alteration may also be a 5' or 3' terminal alteration. The polynucleotide may contain from about 1% to about 100% alternative nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of A, G, U, or C.

Alternative Nucleic Acids

The present disclosure provides nucleic acids (or polynucleotides), including RNAs such as mRNAs that contain one or more alternative nucleosides (termed "alternative nucleic acids") or nucleotides as described herein, which have useful properties including the lack of a substantial induction of the innate immune response of a cell into which the mRNA is introduced. Because these alternative nucleic acids enhance the efficiency of protein production, intracellular retention of nucleic acids, and viability of contacted cells, as well as possess reduced immunogenicity, these nucleic acids having these properties are also termed "enhanced nucleic acids" herein.

The term "nucleic acid," in its broadest sense, includes any compound and/or substance that is or can be incorporated into an oligonucleotide chain. In this context, the term nucleic acid is used synonymously with polynucleotide. Exemplary nucleic acids for use in accordance with the present disclosure include, but are not limited to, one or more of DNA, RNA including messenger mRNA (mRNA), hybrids thereof, RNAi-inducing agents, RNAi agents, siRNAs, shRNAs, miRNAs, antisense RNAs, ribozymes, catalytic DNA, RNAs that induce triple helix formation, aptamers, and vectors.

Provided are alternative nucleic acids containing a translatable region and one, two, or more than two different nucleoside alterations. In some embodiments, the alternative nucleic acid exhibits reduced degradation in a cell into which the nucleic acid is introduced, relative to a corresponding unaltered nucleic acid. Exemplary nucleic acids include ribonucleic acids (RNAs), deoxyribonucleic acids (DNAs), threose nucleic acids (TNAs), glycol nucleic acids (GNAs), or a hybrid thereof. In preferred embodiments, the alternative nucleic acid includes messenger RNAs (mRNAs). As described herein, the nucleic acids of the present disclosure do not substantially induce an innate immune response of a cell into which the mRNA is introduced.

In certain embodiments, it is desirable to intracellularly degrade an alternative nucleic acid introduced into the cell, for example if precise timing of protein production is desired. Thus, the present disclosure provides an alternative nucleic acid containing a degradation domain, which is capable of being acted on in a directed manner within a cell.

Other components of nucleic acid are optional, and are beneficial in some embodiments. For example, a 5' untranslated region (UTR) and/or a 3'-UTR are provided, wherein either or both may independently contain one or more different nucleoside alterations. In such embodiments, nucleoside alterations may also be present in the translatable region. Also provided are nucleic acids containing a Kozak sequence.

Additionally, provided are nucleic acids containing one or more intronic nucleotide sequences capable of being excised from the nucleic acid.

Further, provided are nucleic acids containing an internal ribosome entry site (IRES). An IRES may act as the sole ribosome binding site, or may serve as one of multiple ribosome binding sites of an mRNA. An mRNA containing more than one functional ribosome binding site may encode several peptides or polypeptides that are translated independently by the ribosomes ("multicistronic mRNA"). When nucleic acids are provided with an IRES, further optionally provided is a second translatable region. Examples of IRES sequences that can be used according to the present disclosure include without limitation, those from picornaviruses (e.g. FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

Major Groove Interacting Partners

As described herein, the phrase "major groove interacting partner" refers to RNA recognition receptors that detect and respond to RNA ligands through interactions, e.g. binding, with the major groove face of a nucleotide or nucleic acid.

As such, RNA ligands comprising alternative nucleotides or nucleic acids as described herein decrease interactions with major groove binding partners, and therefore decrease an innate immune response, or expression and secretion of pro-inflammatory cytokines, or both.

Example major groove interacting, e.g. binding, partners include, but are not limited to the following nucleases and helicases. Within membranes, TLRs (Toll-like Receptors) 3, 7, and 8 can respond to single- and double-stranded RNAs. Within the cytoplasm, members of the superfamily 2 class of DEX(D/H) helicases and ATPases can sense RNAs to initiate antiviral responses. These helicases include the RIG-I (retinoic acid-inducible gene I) and MDAS (melanoma differentiation-associated gene 5). Other examples include laboratory of genetics and physiology 2 (LGP2), HIN-200 domain containing proteins, or Helicase-domain containing proteins.

Prevention or Reduction of Innate Cellular Immune Response

The term "innate immune response" includes a cellular response to exogenous single stranded nucleic acids, generally of viral or bacterial origin, which involves the induction of cytokine expression and release, particularly the interferons, and cell death. Protein synthesis is also reduced during the innate cellular immune response. While it is advantageous to eliminate the innate immune response triggered by introduction of exogenous nucleic acids in a cell, the present disclosure provides alternative nucleic acids such as mRNAs that substantially reduce the immune response, including interferon signaling, without entirely eliminating such a response. In some embodiments, the immune response is reduced by 10%, 20%, 30%, 40%, 50%, 60%, 70%, 80%, 90%, 95%, 99%, 99.9%, or greater than 99.9% as compared to the immune response induced by a corresponding unaltered nucleic acid. Such a reduction can be measured by expression or activity level of Type 1 interferons or the expression of interferon-regulated genes such as the toll-like receptors (e.g., TLR7 and TLR8). Reduction or lack of induction of innate immune response can also be measured by decreased cell death following one or more administrations of alternative RNAs to a cell population; e.g., cell death is 10%, 25%, 50%, 75%, 85%, 90%, 95%, or over 95% less than the cell death frequency observed with a corresponding unaltered nucleic acid. Moreover, cell death may affect fewer than 50%, 40%, 30%, 20%, 10%, 5%, 1%, 0.1%, 0.01% or fewer than 0.01% of cells contacted with the alternative nucleic acids.

In some embodiments, the alternative nucleic acids, including polynucleotides and/or mRNA molecules are alternative in such a way as to not induce, or induce only minimally, an immune response by the recipient cell or organism. Such evasion or avoidance of an immune response trigger or activation is a novel feature of the alternative polynucleotides of the present invention.

The present disclosure provides for the repeated introduction (e.g., transfection) of alternative nucleic acids into a target cell population, e.g., in vitro, ex vivo, or in vivo. The step of contacting the cell population may be repeated one or more times (such as two, three, four, five or more than five times). In some embodiments, the step of contacting the cell population with the alternative nucleic acids is repeated a number of times sufficient such that a predetermined efficiency of protein translation in the cell population is achieved. Given the reduced cytotoxicity of the target cell population provided by the nucleic acid alterations, such repeated transfections are achievable in a diverse array of cell types in vitro and/or in vivo.

Minimization of RNA Impurities to Decrease Innate Immune Response

In some embodiments, RNA impurities (e.g., aberrant transcription products) in a composition including mRNA induce an immune response. The RNA impurities such as, short RNAs as a result of abortive transcription initiation events, double stranded RNA generated by RNA dependent RNA polymerase activity, RNA-primed transcription from RNA templates, and/or RNA comprising a self-complementary 3' extension region, may be removed by purification, including purification by reverse phase chromatography. It may be advantageous to eliminate the need for purification by reverse phase chromatography during production of a composition including RNA; therefore, there is a need for strategies to minimizing RNA impurities without reverse phase purification.

In some embodiments, RNA impurities may be minimized by using 5-methoxy-uridine as the uridine source for in vitro synthesis, e.g., in vitro transcription with an RNA polymerase (e.g., T7 RNA polymerase). In some embodiments, a composition including mRNA including 5-methoxy-uridine has fewer RNA impurities. In some embodiments, RNA impurities may be minimized with reverse phase by performing affinity chromatography, precipitation, membrane purification, or tangential flow filtration (TFF) to remove the aberrant transcription products. In some embodiments, the level of aberrant transcription products in a composition may be determined, and purification of the composition, e.g., by reverse phase chromatography performed if the level of aberrant transcription products is greater than a predetermined value.

Polypeptide Variants

Provided are nucleic acids that encode variant polypeptides, which have a certain identity with a reference polypeptide sequence. The term "identity" as known in the art, refers to a relationship between the sequences of two or more peptides, as determined by comparing the sequences. In the art, "identity" also means the degree of sequence relatedness between peptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

In some embodiments, the polypeptide variant has the same or a similar activity as the reference polypeptide. Alternatively, the variant has an altered activity (e.g., increased or decreased) relative to a reference polypeptide. Generally, variants of a particular polynucleotide or polypeptide of the present disclosure will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular reference polynucleotide or polypeptide as determined by sequence alignment programs and parameters described herein and known to those skilled in the art.

As recognized by those skilled in the art, protein fragments, functional protein domains, and homologous proteins are also considered to be within the scope of this present disclosure. For example, provided herein is any protein fragment of a reference protein (meaning a polypeptide sequence at least one amino acid residue shorter than a reference polypeptide sequence but otherwise identical) 10, 20, 30, 40, 50, 60, 70, 80, 90, 100 or greater than 100 amino acids in length In another example, any protein that includes a stretch of about 20, about 30, about 40, about 50, or about 100 amino acids which are about 40%, about 50%, about 60%, about 70%, about 80%, about 90%, about 95%, or about 100% identical to any of the sequences described herein can be utilized in accordance with the present disclosure. In certain embodiments, a protein sequence to be utilized in accordance with the present disclosure includes 2, 3, 4, 5, 6, 7, 8, 9, 10, or more mutations as shown in any of the sequences provided or referenced herein.

Erythropoietin (EPO) and granulocyte colony-stimulating factor (GCSF) are exemplary polypeptides.

Polypeptide Libraries

Also provided are polynucleotide libraries containing nucleoside alterations, wherein the polynucleotides individually contain a first nucleic acid sequence encoding a polypeptide, such as an antibody, protein binding partner, scaffold protein, and other polypeptides known in the art. Preferably, the polynucleotides are mRNA in a form suitable for direct introduction into a target cell host, which in turn synthesizes the encoded polypeptide.

In certain embodiments, multiple variants of a protein, each with different amino acid alteration(s), are produced and tested to determine the best variant in terms of pharmacokinetics, stability, biocompatibility, and/or biological activity, or a biophysical property such as expression level. Such a library may contain 10, $10^2$, $10^3$, $10^4$, $10^5$, $10^6$, $10^7$, $10^8$, $10^9$, or over $10^9$ possible variants (including substitutions, deletions of one or more residues, and insertion of one or more residues).

Polypeptide-Nucleic Acid Complexes

Proper protein translation involves the physical aggregation of a number of polypeptides and nucleic acids associated with the mRNA. Provided by the present disclosure are protein-nucleic acid complexes, containing a translatable mRNA having one or more nucleoside alterations (e.g., at least two different nucleoside alterations) and one or more polypeptides bound to the mRNA. Generally, the proteins are provided in an amount effective to prevent or reduce an innate immune response of a cell into which the complex is introduced.

Synthesis of Alternative Nucleic Acids

Nucleic acids for use in accordance with the present disclosure may be prepared according to any available technique including, but not limited to chemical synthesis, enzymatic synthesis, which is generally termed in vitro transcription, enzymatic or chemical cleavage of a longer precursor, etc. Methods of synthesizing RNAs are known in the art (see, e.g., Gait, M. J. (ed.) *Oligonucleotide synthesis: a practical approach*, Oxford [Oxfordshire], Washington, D.C.: IRL Press, 1984; and Herdewijn, P. (ed.) *Oligonucleotide synthesis: methods and applications*, Methods in Molecular Biology, v. 288 (Clifton, N.J.) Totowa, N.J.: Humana Press, 2005; both of which are incorporated herein by reference).

In certain embodiments, a method for producing an mRNA encoding a polypeptide of interest comprises contacting a cDNA that encodes the protein of interest with an RNA polymerase in the presence of a nucleotide triphosphate mix, wherein at least 90% (e.g., at least 95% or 100%) of the uracils are 5-methoxy-uracil. The invention also provides mRNA produced by such methods. The methods may include additional steps, such as capping (e.g. the addition of a 5'-cap structure), addition of a poly-A tail and/or formulation into a pharmaceutical composition. The RNA polymerase may be T7 RNA polymerase. The in vitro transcription reaction mixture may include a transcription buffer (such as 400 mM Tris-HCl pH 8.0, or an equivalent) and may include $MgCl_2$, DTT, Spermidine (or equivalents). An RNase inhibitor may be included. The remaining reaction volume is generally made up with $dH_2O$. The reaction may be incubated at approximately 37° C. (such as between 30 and 40° C.) and may be incubated for 3 hr-5 hrs (such as 3½ hr-4½ hr, or about 4 hr). The RNA may then be cleaned using DNase and a purification kit.

Alternative nucleic acids need not be uniformly present along the entire length of the molecule. Different nucleotide alterations and/or backbone structures may exist at various positions in the nucleic acid. One of ordinary skill in the art will appreciate that the nucleotide analogs or other alteration(s) may be located at any position(s) of a nucleic acid such that the function of the nucleic acid is not substantially decreased. An alteration may also be a 5' or 3' terminal alteration. The nucleic acids may contain at a minimum one and at maximum 100% alternative nucleotides, or any intervening percentage, such as at least 5% alternative nucleotides, at least 10% alternative nucleotides, at least 25% alternative nucleotides, at least 50% alternative nucleotides, at least 80% alternative nucleotides, or at least 90% alternative nucleotides. For example, the nucleic acids may contain an alternative pyrimidine such as uracil or cytosine. In some embodiments, at least 5%, at least 10%, at least 25%, at least 50%, at least 80%, at least 90% or 100% of the uracil in the nucleic acid is replaced with an alternative uracil. The alternative uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with an alternative cytosine. The alternative cytosine can be replaced by a compound having a single unique structure, or can be replaced by a plurality of compounds having different structures (e.g., 2, 3, 4 or more unique structures).

Generally, the shortest length of an alternative mRNA of the present disclosure can be the length of an mRNA sequence that is sufficient to encode for a dipeptide. In another embodiment, the length of the mRNA sequence is sufficient to encode for a tripeptide. In another embodiment, the length of an mRNA sequence is sufficient to encode for a tetrapeptide. In another embodiment, the length of an mRNA sequence is sufficient to encode for a pentapeptide. In another embodiment, the length of an mRNA sequence is sufficient to encode for a hexapeptide. In another embodiment, the length of an mRNA sequence is sufficient to encode for a heptapeptide. In another embodiment, the length of an mRNA sequence is sufficient to encode for an octapeptide. In another embodiment, the length of an mRNA sequence is sufficient to encode for a nonapeptide. In another embodiment, the length of an mRNA sequence is sufficient to encode for a decapeptide.

Examples of dipeptides that the alternative nucleic acid sequences can encode for include, but are not limited to, carnosine and anserine.

In a further embodiment, the mRNA is greater than 30 nucleotides in length. In another embodiment, the RNA molecule is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 50 nucleotides. In another embodiment, the length is at least 60 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1800 nucleotides. In another embodiment, the length is at least 2000 nucleotides. In another embodiment, the length is at least 2500 nucleotides. In another embodiment, the length is at least 3000 nucleotides. In another embodiment, the length is at least 4000 nucleotides. In another embodiment, the length is at least 5000 nucleotides, or greater than 5000 nucleotides.

For example, the alternative nucleic acids described herein can be prepared using methods that are known to those skilled in the art of nucleic acid synthesis.

In some embodiments, the present disclosure provides for methods of synthesizing a pharmaceutical nucleic acid, comprising the steps of:

a) providing a complementary deoxyribonucleic acid (cDNA) that encodes a pharmaceutical protein of interest;
b) selecting a nucleotide and
c) contacting the provided cDNA and the selected nucleotide with an RNA polymerase, under conditions such that the pharmaceutical nucleic acid is synthesized.

In further embodiments, the pharmaceutical nucleic acid is a ribonucleic acid (RNA).

In still a further aspect of the present disclosure, the alternative nucleic acids can be prepared using solid phase synthesis methods.

5'-Capping

The 5'-cap structure of an mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns removal during mRNA splicing.

Endogenous mRNA molecules may be 5'-end capped generating a 5'-ppp-5'-triphosphate linkage between a terminal guanosine cap residue and the 5'-terminal transcribed sense nucleotide of the mRNA. This 5'-guanylate cap may then be methylated to generate an N7-methyl-guanylate residue. The ribose sugars of the terminal and/or anteterminal transcribed nucleotides of the 5' end of the mRNA may optionally also be 2'-O-methylated. 5'-decapping through hydrolysis and cleavage of the guanylate cap structure may target a nucleic acid molecule, such as an mRNA molecule, for degradation.

Alterations to the nucleic acids of the present invention may generate a non-hydrolyzable cap structure preventing decapping and thus increasing mRNA half-life. Because cap structure hydrolysis requires cleavage of 5'-ppp-5' phosphorodiester linkages, alternative nucleotides may be used during the capping reaction. For example, a Vaccinia Capping Enzyme from New England Biolabs (Ipswich, Mass.) may be used with α-thio-guanosine nucleotides according to the manufacturer's instructions to create a phosphorothioate linkage in the 5'-ppp-5' cap. Additional alternative guanosine nucleotides may be used such as α-methyl-phosphonate and seleno-phosphate nucleotides.

Additional alterations include, but are not limited to, 2'-O-methylation of the ribose sugars of 5'-terminal and/or 5'-anteterminal nucleotides of the mRNA (as mentioned above) on the 2'-hydroxyl group of the sugar ring. Multiple distinct 5'-cap structures can be used to generate the 5'-cap of a nucleic acid molecule, such as an mRNA molecule.

5'-cap structures include those described in International Patent Publication Nos. WO2008127688, WO 2008016473, and WO 2011015347, each of which is incorporated herein by reference in its entirety.

Cap analogs, which herein are also referred to as synthetic cap analogs, chemical caps, chemical cap analogs, or structural or functional cap analogs, differ from natural (i.e. endogenous, wild-type or physiological) 5'-caps in their chemical structure, while retaining cap function. Cap analogs may be chemically (i.e. non-enzymatically) or enzymatically synthesized and/linked to a nucleic acid molecule.

For example, the Anti-Reverse Cap Analog (ARCA) cap contains two guanosines linked by a 5'-5'-triphosphate group, wherein one guanosine contains an N7 methyl group as well as a 3'-O-methyl group (i.e., N7,3'-O-dimethyl-guanosine-5'-triphosphate-5'-guanosine ($m^7$G-3'mppp-G; which may equivalently be designated 3'-O-Me-m7G(5')ppp(5')G). The 3'-O atom of the other, unaltered, guanosine becomes linked to the 5'-terminal nucleotide of the capped nucleic acid molecule (e.g. an mRNA or mmRNA). The N7- and 3'-O-methlyated guanosine provides the terminal moiety of the capped nucleic acid molecule (e.g. mRNA or mmRNA).

Another exemplary cap is mCAP, which is similar to ARCA but has a 2'-O-methyl group on guanosine (i.e., N7,2'-O-dimethyl-guanosine-5'-triphosphate-5'-guanosine, mtm-ppp-G).

In one embodiment, the cap is a dinucleotide cap analog. As a non-limiting example, the dinucleotide cap analog may be modified at different phosphate positions with a boranophosphate group or a phophoroselenoate group such as the dinucleotide cap analogs described in U.S. Pat. No. 8,519,110, the contents of which are herein incorporated by reference in its entirety.

In another embodiment, the cap analog is a N7-(4-chlorophenoxyethyl) substituted dicnucleotide form of a cap analog known in the art and/or described herein. Non-limiting examples of a N7-(4-chlorophenoxyethyl) substituted dinucleotide form of a cap analog include a N7-(4-chlorophenoxyethyl)-G(5')ppp(5')G and a N7-(4-chlorophenoxyethyl)-m3'-OG(5')ppp(5')G cap analog (See e.g., the various cap analogs and the methods of synthesizing cap analogs described in Kore et al. Bioorganic & Medicinal Chemistry 2013 21:4570-4574; the contents of which are herein incorporated by reference in its entirety). In another embodiment, a cap analog of the present invention is a 4-chloro/bromophenoxyethyl analog.

While cap analogs allow for the concomitant capping of a nucleic acid molecule in an in vitro transcription reaction, up to 20% of transcripts remain uncapped. This, as well as the structural differences of a cap analog from endogenous 5'-cap structures of nucleic acids produced by the endogenous, cellular transcription machinery, may lead to reduced translational competency and reduced cellular stability.

Alternative nucleic acids of the invention may also be capped post-transcriptionally, using enzymes, in order to generate more authentic 5'-cap structures. As used herein, the phrase "more authentic" refers to a feature that closely mirrors or mimics, either structurally or functionally, an endogenous or wild-type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'-cap structures of the present invention are those which, among other things, have enhanced binding of cap binding proteins, increased half life, reduced susceptibility to 5' endonucleases and/or reduced 5' decapping, as compared to synthetic 5'-cap structures known in the art (or to a wild-type, natural or physiological 5'-cap structure). For example, recombinant Vaccinia Virus Capping Enzyme and recombinant 2'-O-methyltransferase enzyme can create a canonical 5'-5'-triphosphate linkage between the 5'-terminal nucleotide of an mRNA and a guanosine cap nucleotide wherein the cap guanosine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include 7mG(5')ppp(5')N,pN2p (cap 0), 7mG(5')ppp(5')NImpNp (cap 1), 7mG(5')-ppp(5') NImpN2mp (cap 2) and m(7)Gpppm(3)(6,6,2')Apm(2')Apm (2')Cpm(2)(3,2')Up (cap 4).

Because the alternative nucleic acids may be capped post-transcriptionally, and because this process is more efficient, nearly 100% of the alternative nucleic acids may be capped. This is in contrast to ~80% when a cap analog is linked to an mRNA in the course of an in vitro transcription reaction.

According to the present invention, 5' terminal caps may include endogenous caps or cap analogs. According to the present invention, a 5' terminal cap may comprise a guanosine analog. Useful guanosine analogs include inosine, N1-methyl-guanosine, 2'fluoro-guanosine, 7-deaza-guanosine, 8-oxo-guanosine, 2-amino-guanosine, LNA-guanosine, and 2-azido-guanosine.

In one embodiment, the nucleic acids described herein may contain a modified 5'-cap. A modification on the 5'-cap may increase the stability of mRNA, increase the half-life of the mRNA, and could increase the mRNA translational efficiency. The modified 5'-cap may include, but is not limited to, one or more of the following modifications: modification at the 2' and/or 3' position of a capped guanosine triphosphate (GTP), a replacement of the sugar ring oxygen (that produced the carbocyclic ring) with a methylene moiety ($CH_2$), a modification at the triphosphate bridge moiety of the cap structure, or a modification at the nucleobase (G) moiety.

The 5'-cap structure that may be modified includes, but is not limited to, the caps described herein such as Cap0 having the substrate structure for cap dependent translation of:

(CAP-001)

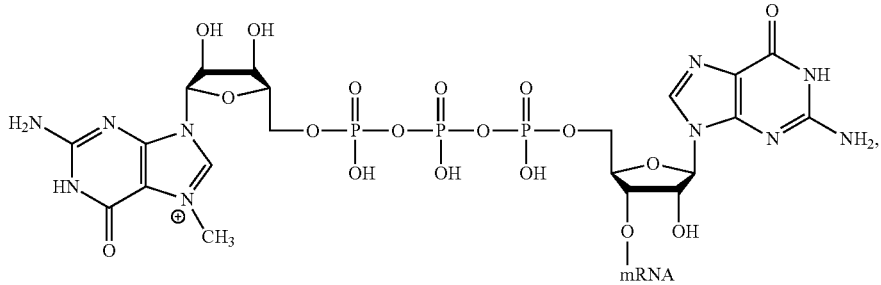

or Cap1 having the substrate structure for cap dependent translation of:

(CAP-002)

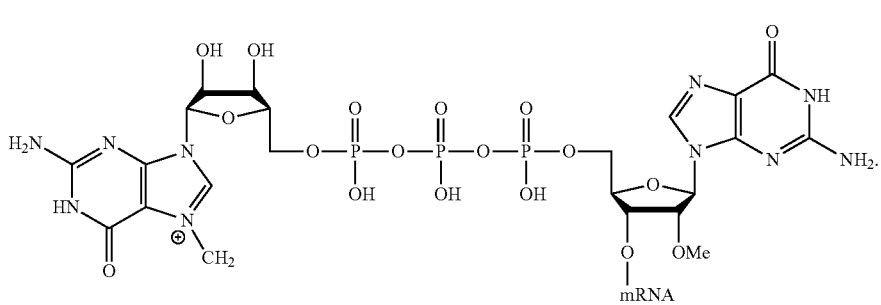

As a non-limiting example, the modified 5'-cap may have the substrate structure for cap dependent translation of:

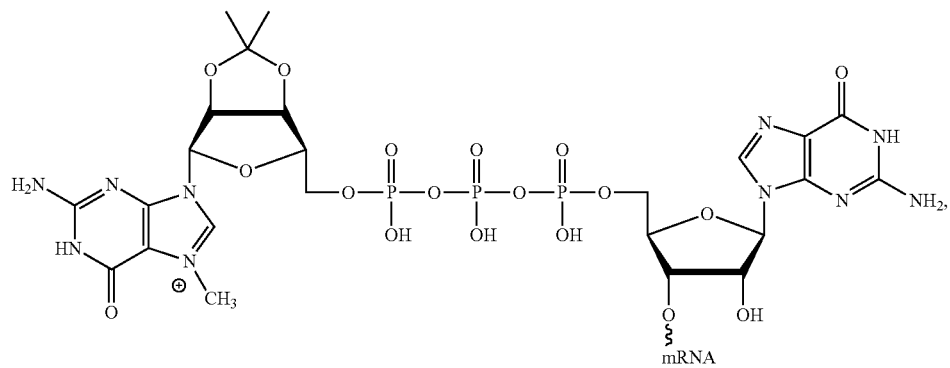
(CAP-003)
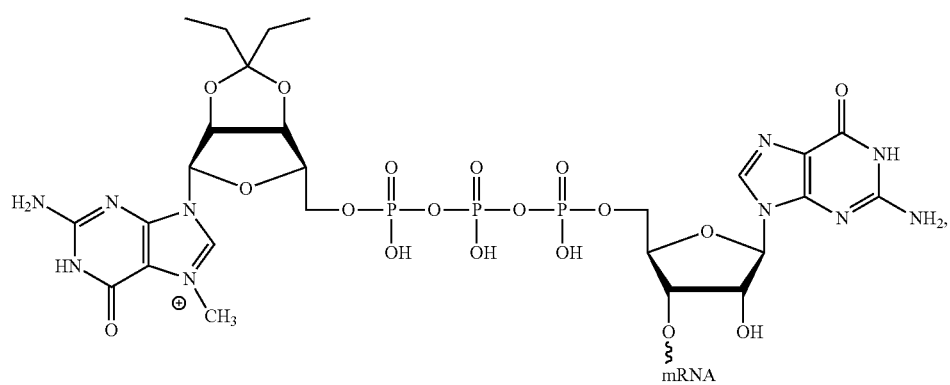
(CAP-004)
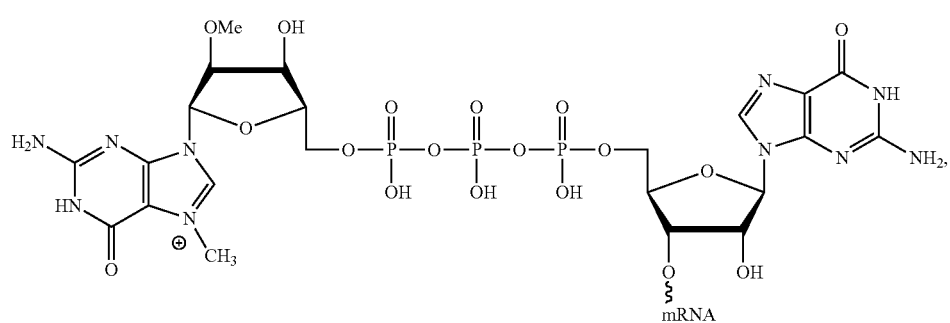
(CAP-005)
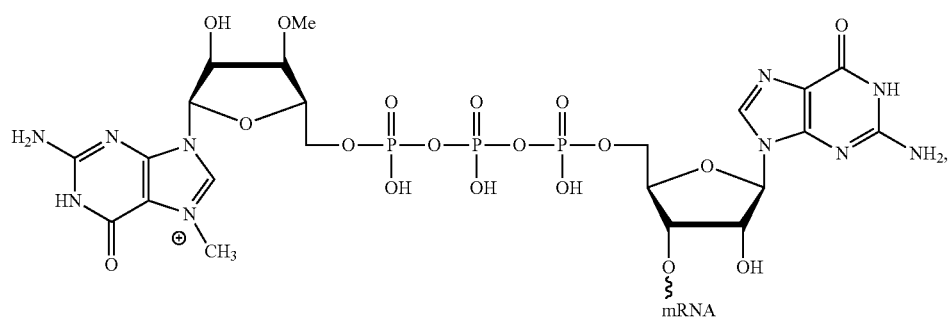
(CAP-006)

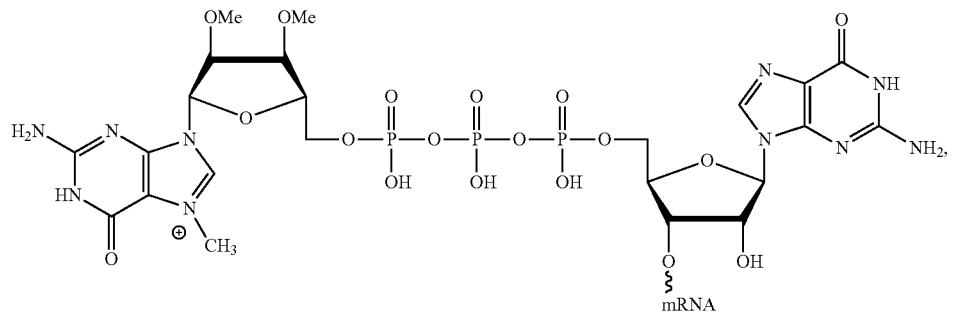
(CAP-007)
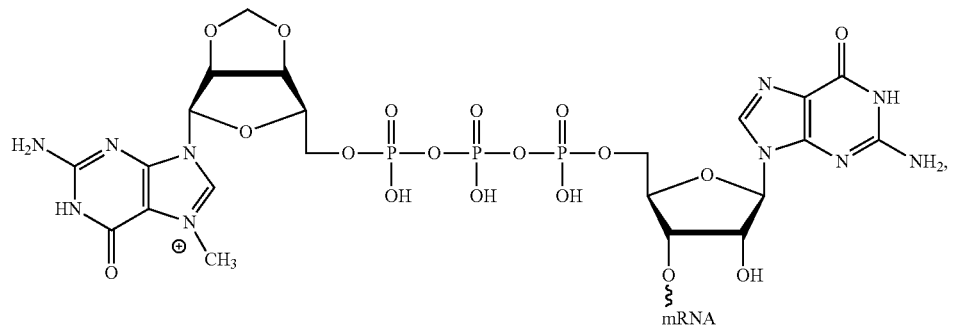
(CAP-008)
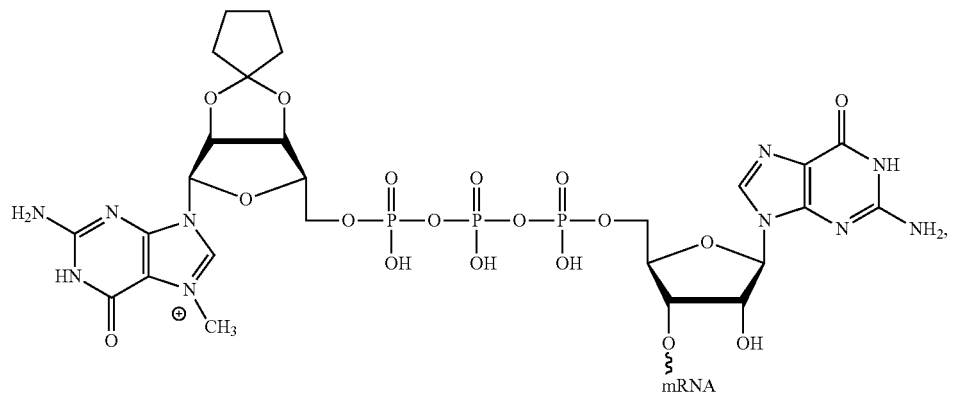
(CAP-009)
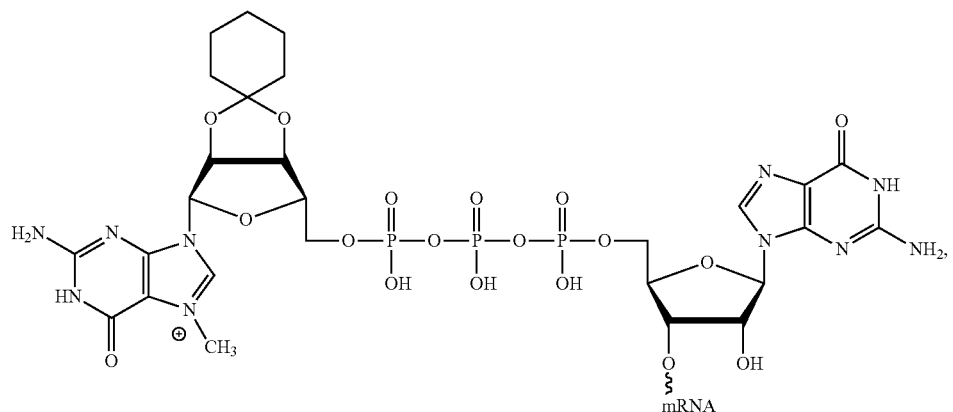
(CAP-010)

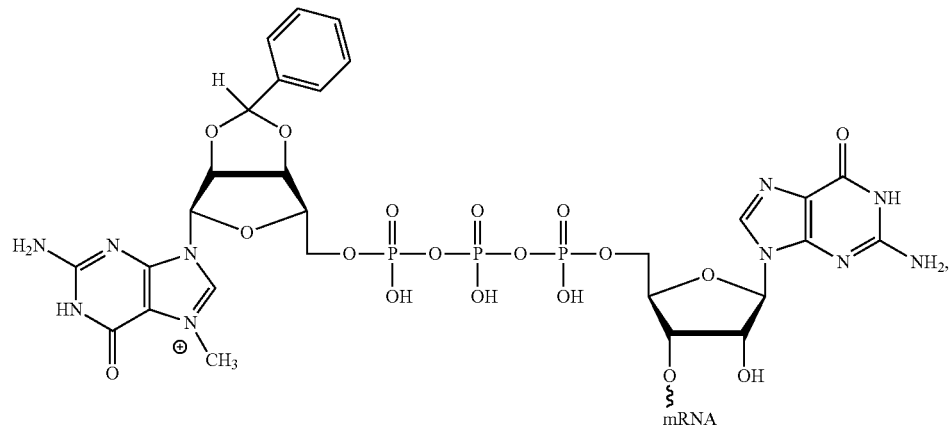
(CAP-011)
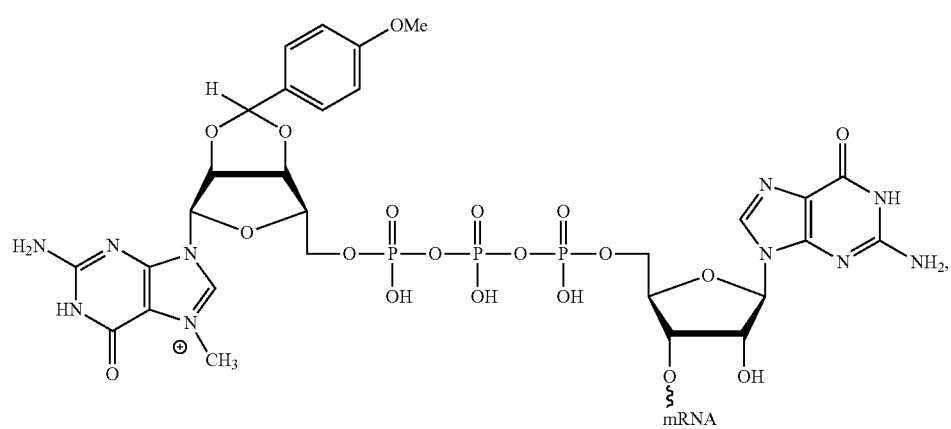
(CAP-012)
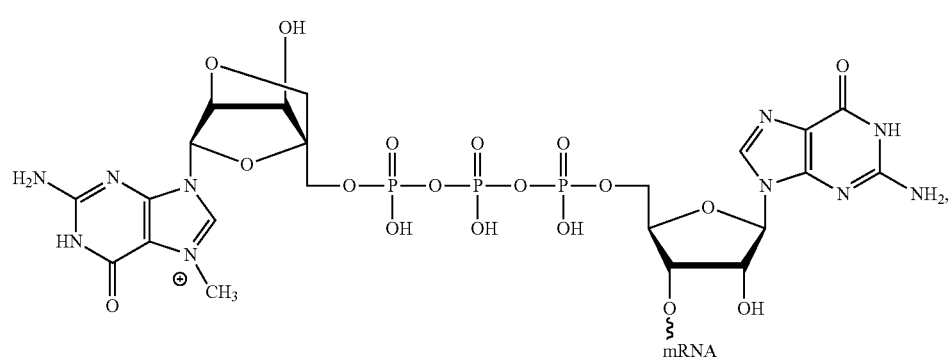
(CAP-013)
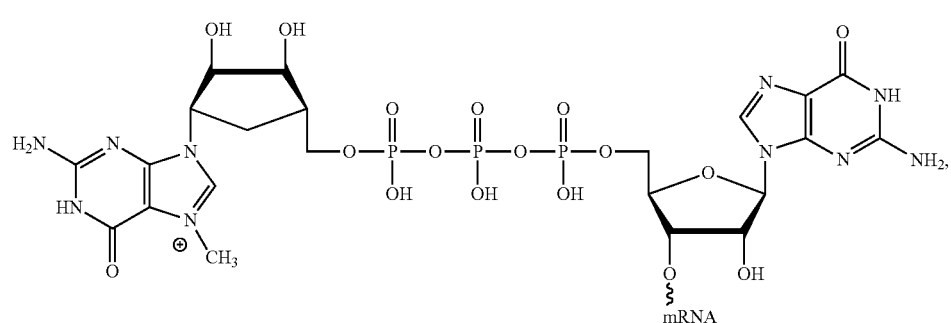
(CAP-014)

(CAP-015)
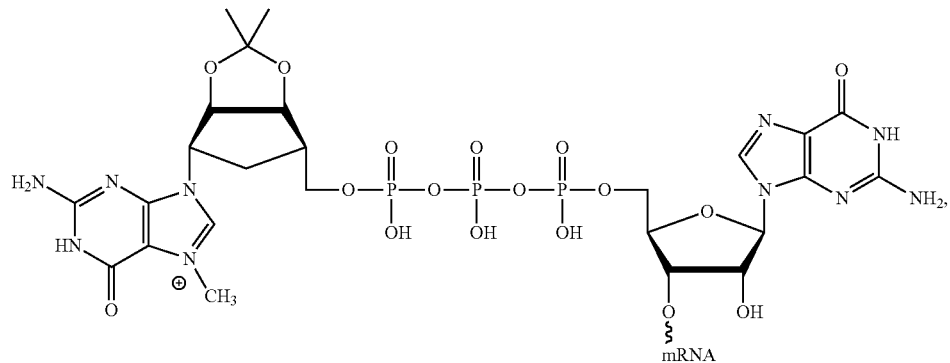
(CAP-016)
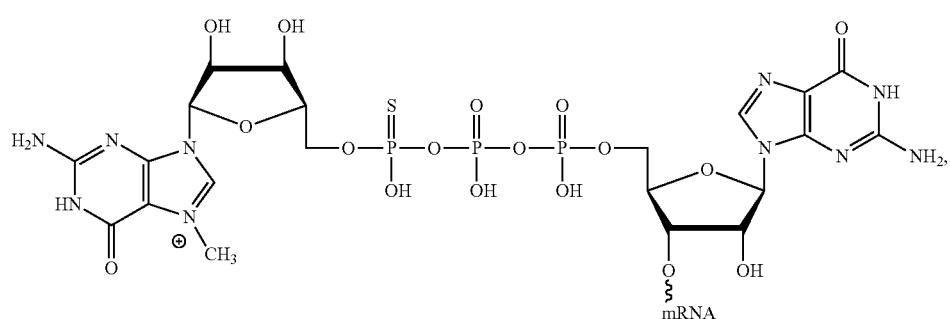
(CAP-017)
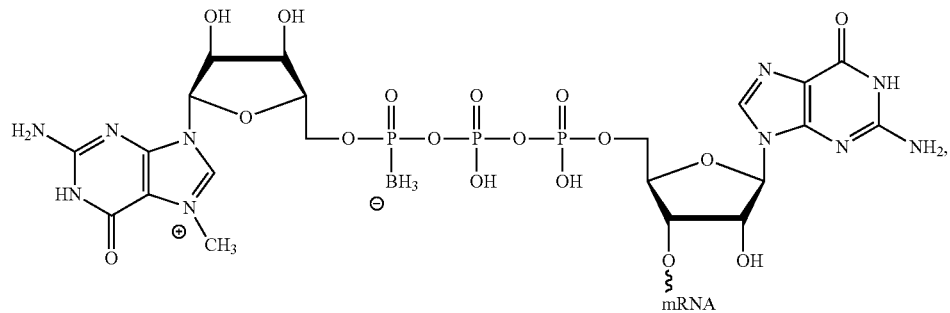
(CAP-018)
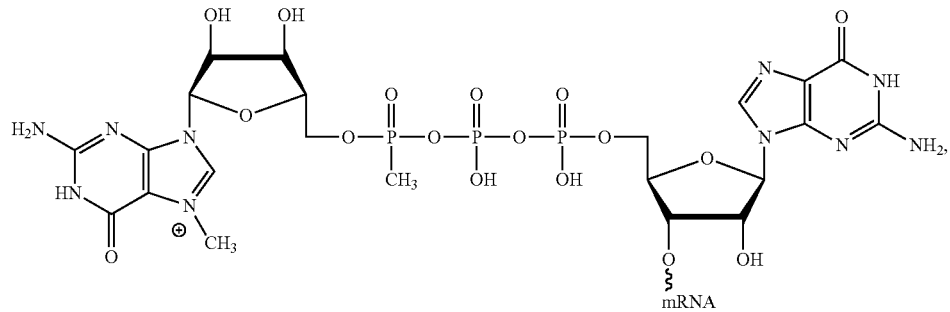
(CAP-019)
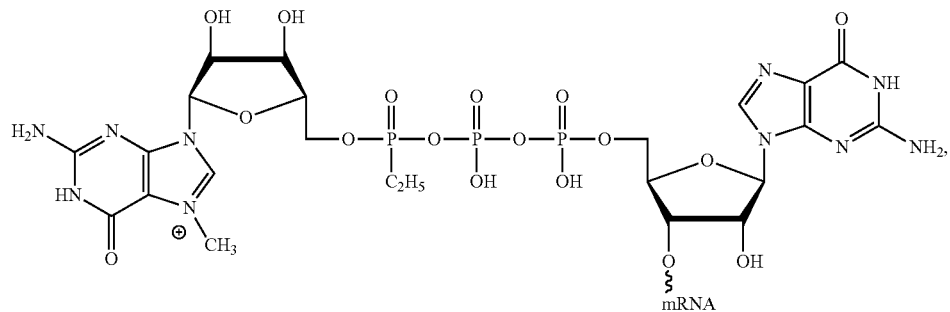

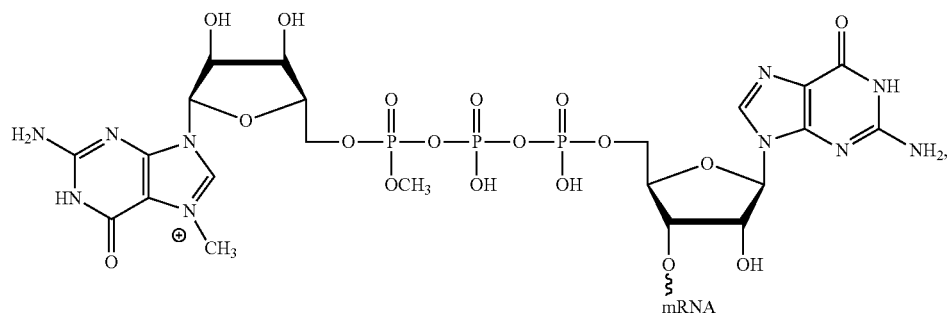
(CAP-020)

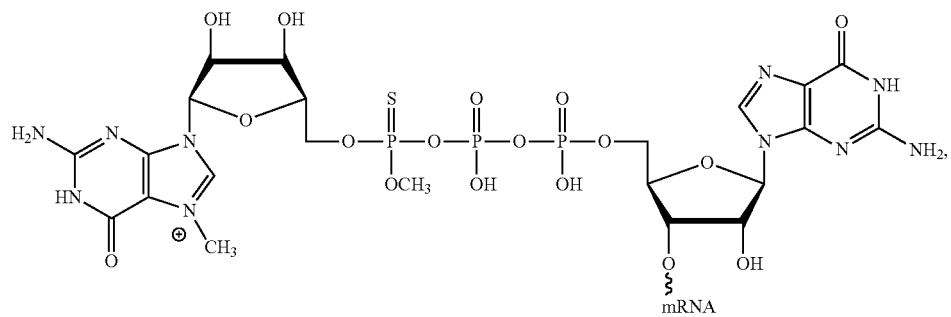
(CAP-021)

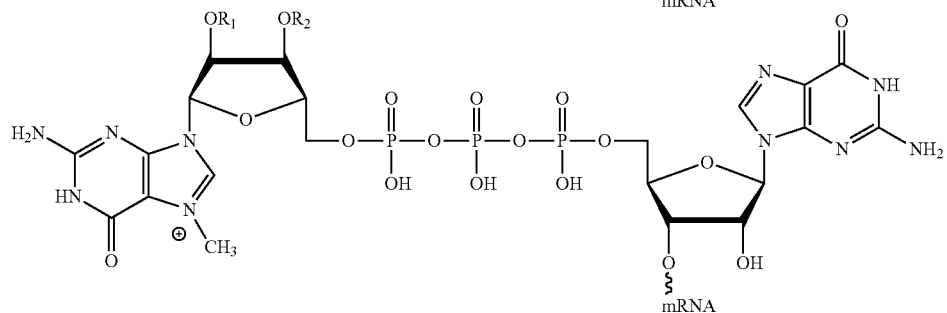

where R₁ and R₂ are defined in Table 5:

TABLE 5

R₁ and R₂ groups for CAP-022 to CAP096.

| Cap Structure Number | R₁ | R₂ |
|---|---|---|
| CAP-022 | C₂H₅ (Ethyl) | H |
| CAP-023 | H | C₂H₅ (Ethyl) |
| CAP-024 | C₂H₅ (Ethyl) | C₂H₅ (Ethyl) |
| CAP-025 | C₃H₇ (Propyl) | H |
| CAP-026 | H | C₃H₇ (Propyl) |
| CAP-027 | C₃H₇ (Propyl) | C₃H₇ (Propyl) |
| CAP-028 | C₄H₉ (Butyl) | H |
| CAP-029 | H | C₄H₉ (Butyl) |
| CAP-030 | C₄H₉ (Butyl) | C₄H₉ (Butyl) |
| CAP-031 | C₅H₁₁ (Pentyl) | H |
| CAP-032 | H | C₅H₁₁ (Pentyl) |
| CAP-033 | C₅H₁₁ (Pentyl) | C₅H₁₁ (Pentyl) |
| CAP-034 | H₂C—C≡CH (Propargyl) | H |
| CAP-035 | H | H₂C—C≡CH (Propargyl) |
| CAP-036 | H₂C—C≡CH (Propargyl) | H₂C—C≡CH (Propargyl) |
| CAP-037 | CH₂CH=CH₂ (Allyl) | H |
| CAP-038 | H | CH₂CH=CH₂ (Allyl) |
| CAP-039 | CH₂CH=CH₂ (Allyl) | CH₂CH=CH₂ (Allyl) |
| CAP-040 | CH₂OCH₃ (MOM) | H |

TABLE 5-continued

R₁ and R₂ groups for CAP-022 to CAP096.

| Cap Structure Number | R₁ | R₂ |
|---|---|---|
| CAP-041 | H | CH₂OCH₃ (MOM) |
| CAP-042 | CH₂OCH₃ (MOM) | CH₂OCH₃ (MOM) |
| CAP-043 | CH₂OCH₂CH₂OCH₃ (MEM) | H |
| CAP-044 | H | CH₂OCH₂CH₂OCH₃ (MEM) |
| CAP-045 | CH₂OCH₂CH₂OCH₃ (MEM) | CH₂OCH₂CH₂OCH₃ (MEM) |
| CAP-046 | CH₂SCH₃ (MTM) | H |
| CAP-047 | H | CH₂SCH₃ (MTM) |
| CAP-048 | CH₂SCH₃ (MTM) | CH₂SCH₃ (MTM) |
| CAP-049 | CH₂C₆H₅ (Benzyl) | H |
| CAP-050 | H | CH₂C₆H₅ (Benzyl) |
| CAP-051 | CH₂C₆H₅ (Benzyl) | CH₂C₆H₅ (Benzyl) |
| CAP-052 | CH₂OCH₂C₆H₅ (BOM) | H |
| CAP-053 | H | CH₂OCH₂C₆H₅ (BOM) |
| CAP-054 | CH₂OCH₂C₆H₅ (BOM) | CH₂OCH₂C₆H₅ (BOM) |
| CAP-055 | CH₂C₆H₄—OMe (p-Methoxybenzyl) | H |
| CAP-056 | H | CH₂C₆H₄—OMe (p-Methoxybenzyl) |
| CAP-057 | CH₂C₆H₄—OMe (p-Methoxybenzyl) | CH₂C₆H₄—OMe (p-Methoxybenzyl) |
| CAP-058 | CH₂C₆H₄—NO₂ (p-Nitrobenzyl) | H |
| CAP-059 | H | CH₂C₆H₄—NO₂ (p-Nitrobenzyl) |

TABLE 5-continued

R₁ and R₂ groups for CAP-022 to CAP096.

| Cap Structure Number | R₁ | R₂ |
|---|---|---|
| CAP-060 | CH₂C₆H₄—NO₂ (p-Nitrobenzyl) | CH₂C₆H₄—NO₂ (p-Nitrobenzyl) |
| CAP-061 | CH₂C₆H₄—X (p-Halobenzyl) where X = F, Cl, Br or I | H |
| CAP-062 | H | CH₂C₆H₄—X (p-Halobenzyl) where X = F, Cl, Br or I |
| CAP-063 | CH₂C₆H₄—X (p-Halobenzyl) where X = F, Cl, Br or I | CH₂C₆H₄—X (p-Halobenzyl) where X = F, Cl, Br or I |
| CAP-064 | CH₂C₆H₄—N₃ (p-Azidobenzyl) | H |
| CAP-065 | H | CH₂C₆H₄—N₃ (p-Azidobenzyl) |
| CAP-066 | CH₂C₆H₄—N₃ (p-Azidobenzyl) | CH₂C₆H₄—N₃ (p-Azidobenzyl) |
| CAP-067 | CH₂C₆H₄—CF₃ (p-Trifluoromethylbenzyl) | H |
| CAP-068 | H | CH₂C₆H₄—CF₃ (p-Trifluoromethylbenzyl) |
| CAP-069 | CH₂C₆H₄—CF₃ (p-Trifluoromethylbenzyl) | CH₂C₆H₄—CF₃ (p-Trifluoromethylbenzyl) |
| CAP-070 | CH₂C₆H₄—OCF₃ (p-Trifluoromethoxylbenzyl) | H |
| CAP-071 | H | CH₂C₆H₄—OCF₃ (p-Trifluoromethoxylbenzyl) |

TABLE 5-continued

R₁ and R₂ groups for CAP-022 to CAP096.

| Cap Structure Number | R₁ | R₂ |
|---|---|---|
| CAP-083 | H | P(O)(OH)₂ (MP) |
| CAP-084 | P(O)(OH)₂ (MP) | P(O)(OH)₂ (MP) |
| CAP-085 | P(S)(OH)₂ (Thio-MP) | H |
| CAP-086 | H | P(S)(OH)₂ (Thio-MP) |
| CAP-087 | P(S)(OH)₂ (Thio-MP) | P(S)(OH)₂ (Thio-MP) |
| CAP-088 | P(O)(CH₃)(OH) (Methylphophonate) | H |
| CAP-089 | H | P(O)(CH₃)(OH) (Methylphophonate) |
| CAP-090 | P(O)(CH₃)(OH) (Methylphophonate) | P(O)(CH₃)(OH) (Methylphophonate) |
| CAP-091 | PN(ⁱPr)₂(OCH₂CH₂CN) (Phosporamidite) | H |
| CAP-092 | H | PN(ⁱPr)₂(OCH₂CH₂CN) (Phosporamidite) |
| CAP-093 | PN(ⁱPr)₂(OCH₂CH₂CN) (Phosporamidite) | PN(ⁱPr)₂(OCH₂CH₂CN) (Phosporamidite) |
| CAP-094 | SO₂CH₃ (Methanesulfonic acid) | H |
| CAP-095 | H | SO₂CH₃ (Methanesulfonic acid) |
| CAP-096 | SO₂CH₃ (Methanesulfonic acid) | SO₂CH₃ (Methanesulfonic acid) |

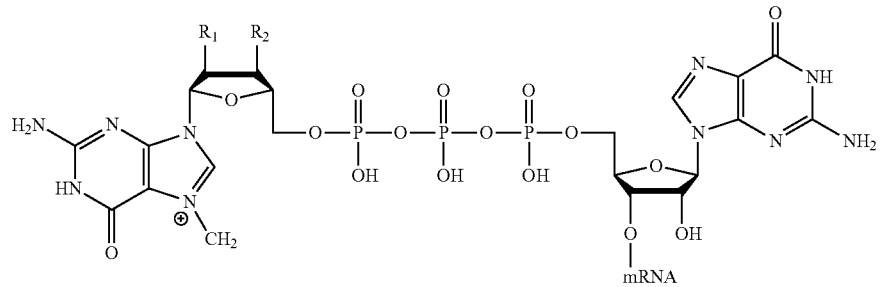

TABLE 5-continued

R₁ and R₂ groups for CAP-022 to CAP096.

| Cap Structure Number | R₁ | R₂ |
|---|---|---|
| CAP-072 | CH₂C₆H₄—OCF₃ (p-Trifluoromethoxylbenzyl) | CH₂C₆H₄—OCF₃ (p-Trifluoromethoxylbenzyl) |
| CAP-073 | CH₂C₆H₃—(CF₃)₂ [2,4-bis(Trifluoromethyl)benzyl] | H |
| CAP-074 | H | CH₂C₆H₃—(CF₃)₂ [2,4-bis(Trifluoromethyl)benzyl] |
| CAP-075 | CH₂C₆H₃—(CF₃)₂ [2,4-bis(Trifluoromethyl)benzyl] | CH₂C₆H₃—(CF₃)₂ [2,4-bis(Trifluoromethyl)benzyl] |
| CAP-076 | Si(C₆H₅)₂C₄H₉ (t-Butyldiphenylsilyl) | H |
| CAP-077 | H | Si(C₆H₅)₂C₄H₉ (t-Butyldiphenylsilyl) |
| CAP-078 | Si(C₆H₅)₂C₄H₉ (t-Butyldiphenylsilyl) | Si(C₆H₅)₂C₄H₉ (t-Butyldiphenylsilyl) |
| CAP-079 | CH₂CH₂CH=CH₂ (Homoallyl) | H |
| CAP-080 | H | CH₂CH₂CH=CH₂ (Homoallyl) |
| CAP-081 | CH₂CH₂CH=CH₂ (Homoallyl) | CH₂CH₂CH=CH₂ (Homoallyl) |
| CAP-082 | P(O)(OH)₂ (MP) | H | or where R₁ and R₂ are defined in Table 6:

TABLE 6

R₁ and R₂ groups for CAP-097 to CAP111.

| Cap Structure Number | R₁ | R₂ |
|---|---|---|
| CAP-097 | NH₂ (amino) | H |
| CAP-098 | H | NH₂ (amino) |
| CAP-099 | NH₂ (amino) | NH₂ (amino) |
| CAP-100 | N₃ (Azido) | H |
| CAP-101 | H | N₃ (Azido) |
| CAP-102 | N₃ (Azido) | N₃ (Azido) |
| CAP-103 | X (Halo: F, Cl, Br, I) | H |
| CAP-104 | H | X (Halo: F, Cl, Br, I) |
| CAP-105 | X (Halo: F, Cl, Br, I) | X (Halo: F, Cl, Br, I) |
| CAP-106 | SH (Thiol) | H |
| CAP-107 | H | SH (Thiol) |
| CAP-108 | SH (Thiol) | SH (Thiol) |
| CAP-109 | SCH₃ (Thiomethyl) | H |
| CAP-110 | H | SCH₃ (Thiomethyl) |
| CAP-111 | SCH₃ (Thiomethyl) | SCH₃ (Thiomethyl) |

In Table 5, "MOM" stands for methoxymethyl, "MEM" stands for methoxyethoxymethyl, "MTM" stands for methylthiomethyl, "BOM" stands for benzyloxymethyl and "MP" stands for monophosphonate.
In a non-limiting example, the modified 5'-cap may have the substrate structure for vaccinia mRNA capping enzyme of:
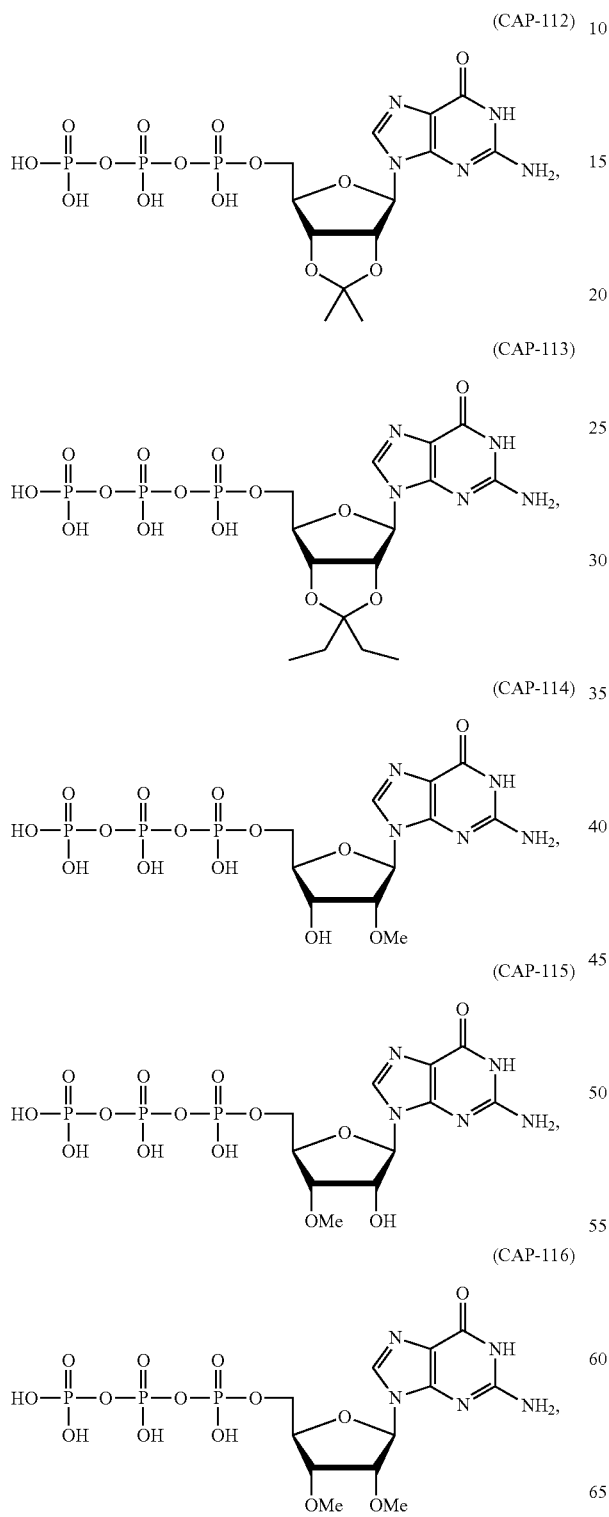
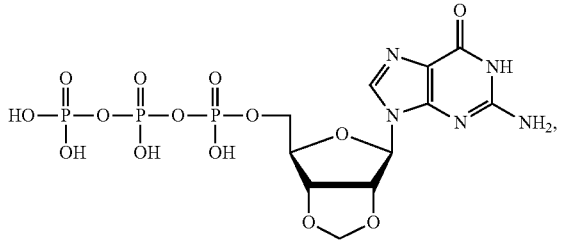
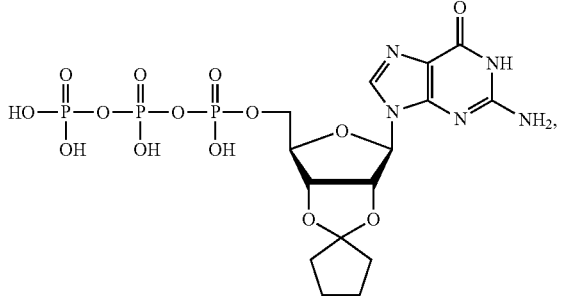
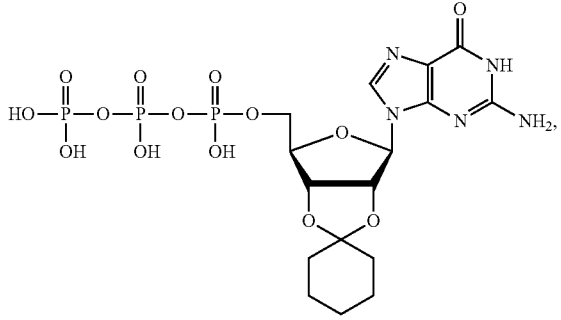
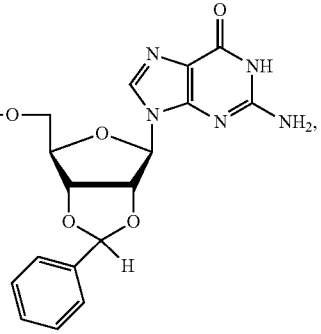

(CAP-121)
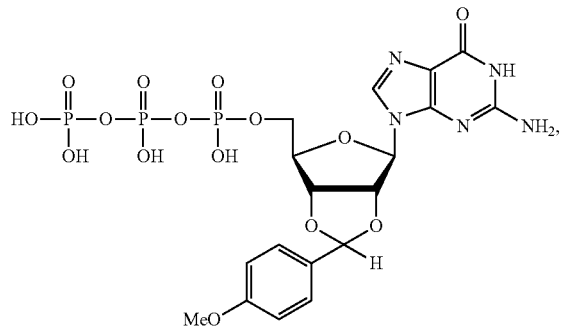
(CAP-126)
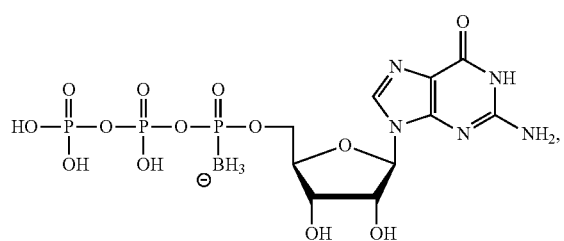
(CAP-122)
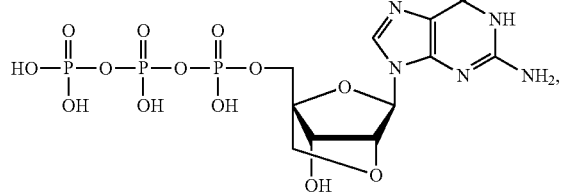
(CAP-127)
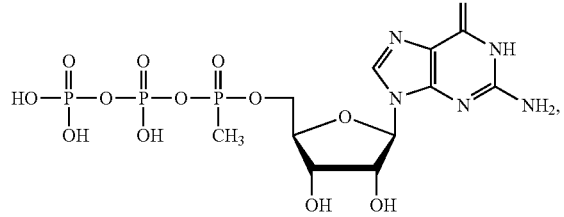
(CAP-128)
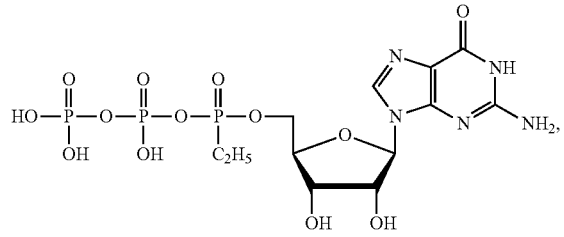
(CAP-123)
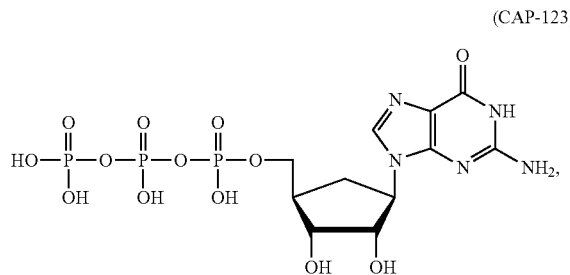
(CAP-129)
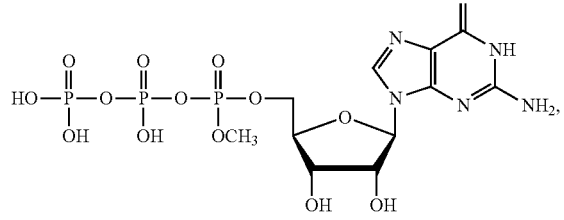
(CAP-124)
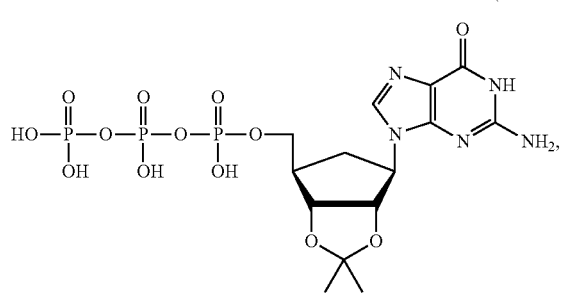
(CAP-130)
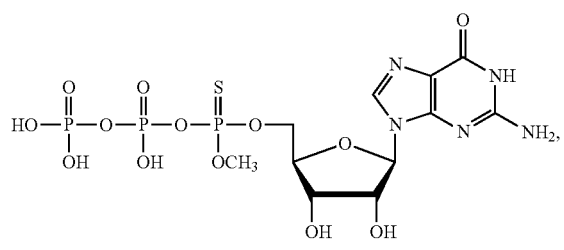
(CAP-125)
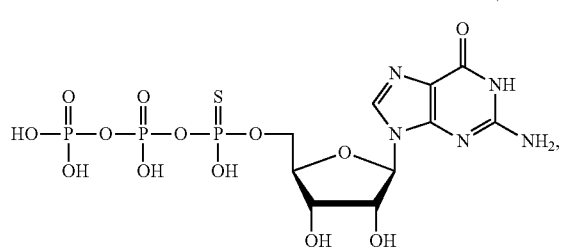
(CAP-131)
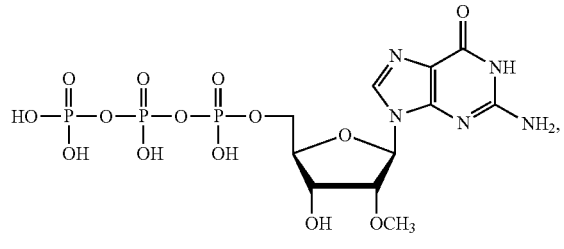

-continued

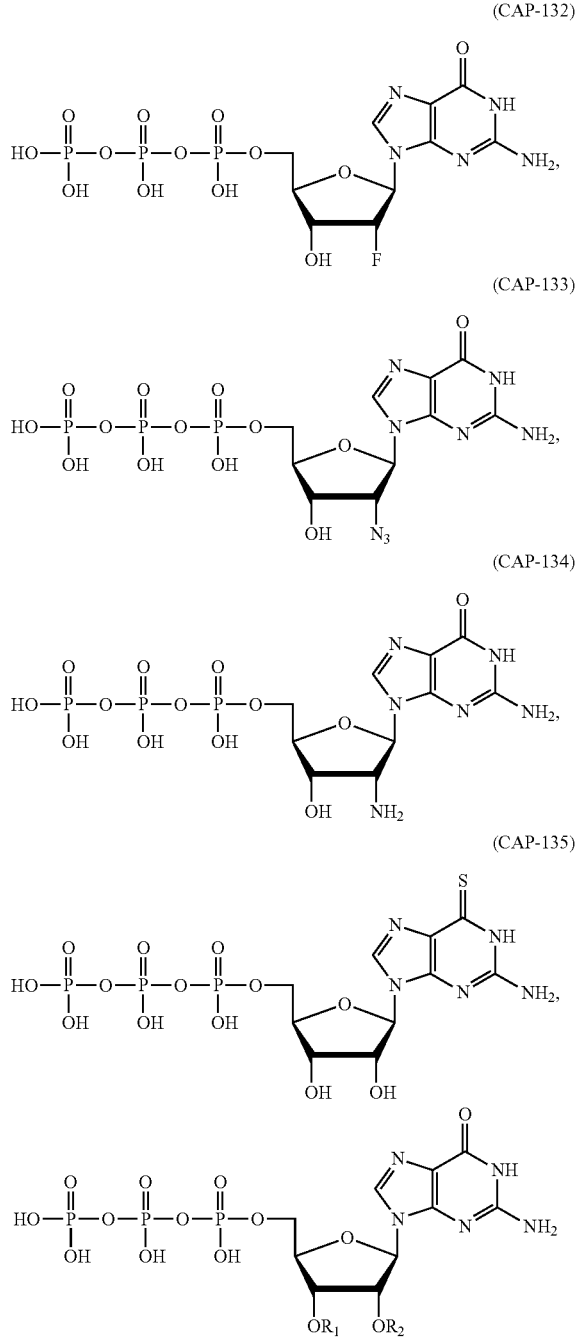

(CAP-132)
(CAP-133)
(CAP-134)
(CAP-135)

where $R_1$ and $R_2$ are defined in Table 7:

TABLE 7

| Cap Structure Number | $R_1$ | $R_2$ |
|---|---|---|
| | \multicolumn{2}{c}{$R_1$ and $R_2$ groups for CAP-136 to CAP-210.} | |
| CAP-136 | $C_2H_5$ (Ethyl) | H |
| CAP-137 | H | $C_2H_5$ (Ethyl) |
| CAP-138 | $C_2H_5$ (Ethyl) | $C_2H_5$ (Ethyl) |
| CAP-139 | $C_3H_7$ (Propyl) | H |
| CAP-140 | H | $C_3H_7$ (Propyl) |
| CAP-141 | $C_3H_7$ (Propyl) | $C_3H_7$ (Propyl) |
| CAP-142 | $C_4H_9$ (Butyl) | H |
| CAP-143 | H | $C_4H_9$ (Butyl) |
| CAP-144 | $C_4H_9$ (Butyl) | $C_4H_9$ (Butyl) |
| CAP-145 | $C_5H_{11}$ (Pentyl) | H |
| CAP-146 | H | $C_5H_{11}$ (Pentyl) |
| CAP-147 | $C_5H_{11}$ (Pentyl) | $C_5H_{11}$ (Pentyl) |
| CAP-148 | $H_2C-C\equiv CH$ (Propargyl) | H |
| CAP-149 | H | $H_2C-C\equiv CH$ (Propargyl) |
| CAP-150 | $H_2C-C\equiv CH$ (Propargyl) | $H_2C-C\equiv CH$ (Propargyl) |
| CAP-151 | $CH_2CH=CH_2$ (Allyl) | H |
| CAP-152 | H | $CH_2CH=CH_2$ (Allyl) |
| CAP-153 | $CH_2CH=CH_2$ (Allyl) | $CH_2CH=CH_2$ (Allyl) |
| CAP-154 | $CH_2OCH_3$ (MOM) | H |
| CAP-155 | H | $CH_2OCH_3$ (MOM) |
| CAP-156 | $CH_2OCH_3$ (MOM) | $CH_2OCH_3$ (MOM) |
| CAP-157 | $CH_2OCH_2CH_2OCH_3$ (MEM) | H |
| CAP-158 | H | $CH_2OCH_2CH_2OCH_3$ (MEM) |
| CAP-159 | $CH_2OCH_2CH_2OCH_3$ (MEM) | $CH_2OCH_2CH_2OCH_3$ (MEM) |
| CAP-160 | $CH_2SCH_3$ (MTM) | H |
| CAP-161 | H | $CH_2SCH_3$ (MTM) |
| CAP-162 | $CH_2SCH_3$ (MTM) | $CH_2SCH_3$ (MTM) |
| CAP-163 | $CH_2C_6H_5$ (Benzyl) | H |
| CAP-164 | H | $CH_2C_6H_5$ (Benzyl) |
| CAP-165 | $CH_2C_6H_5$ (Benzyl) | $CH_2C_6H_5$ (Benzyl) |
| CAP-166 | $CH_2OCH_2C_6H_5$ (BOM) | H |
| CAP-167 | H | $CH_2OCH_2C_6H_5$ (BOM) |
| CAP-168 | $CH_2OCH_2C_6H_5$ (BOM) | $CH_2OCH_2C_6H_5$ (BOM) |
| CAP-169 | $CH_2C_6H_4-OMe$ (p-Methoxybenzyl) | H |
| CAP-170 | H | $CH_2C_6H_4-OMe$ (p-Methoxybenzyl) |
| CAP-171 | $CH_2C_6H_4-OMe$ (p-Methoxybenzyl) | $CH_2C_6H_4-OMe$ (p-Methoxybenzyl) |
| CAP-172 | $CH_2C_6H_4-NO_2$ (p-Nitrobenzyl) | H |
| CAP-173 | H | $CH_2C_6H_4-NO_2$ (p-Nitrobenzyl) |
| CAP-174 | $CH_2C_6H_4-NO_2$ (p-Nitrobenzyl) | $CH_2C_6H_4-NO_2$ (p-Nitrobenzyl) |
| CAP-175 | $CH_2C_6H_4-X$ (p-Halobenzyl) where X = F, Cl, Br or I | H |
| CAP-176 | H | $CH_2C_6H_4-X$ (p-Halobenzyl) where X = F, Cl, Br or I |
| CAP-177 | $CH_2C_6H_4-X$ (p-Halobenzyl) where X = F, Cl, Br or I | $CH_2C_6H_4-X$ (p-Halobenzyl) where X = F, Cl, Br or I |
| CAP-178 | $CH_2C_6H_4-N_3$ (p-Azidobenzyl) | H |
| CAP-179 | H | $CH_2C_6H_4-N_3$ (p-Azidobenzyl) |
| CAP-180 | $CH_2C_6H_4-N_3$ (p-Azidobenzyl) | $CH_2C_6H_4-N_3$ (p-Azidobenzyl) |
| CAP-181 | $CH_2C_6H_4-CF_3$ (p-Trifluoromethylbenzyl) | H |
| CAP-182 | H | $CH_2C_6H_4-CF_3$ (p-Trifluoromethylbenzyl) |
| CAP-183 | $CH_2C_6H_4-CF_3$ (p-Trifluoromethylbenzyl) | $CH_2C_6H_4-CF_3$ (p-Trifluoromethylbenzyl) |
| CAP-184 | $CH_2C_6H_4-OCF_3$ (p-Trifluoromethoxylbenzyl) | H |
| CAP-185 | H | $CH_2C_6H_4-OCF_3$ (p-Trifluoromethoxylbenzyl) |
| CAP-186 | $CH_2C_6H_4-OCF_3$ (p-Trifluoromethoxylbenzyl) | $CH_2C_6H_4-OCF_3$ (p-Trifluoromethoxylbenzyl) |
| CAP-187 | $CH_2C_6H_3-(CF_3)_2$ [2,4-bis(Trifluoromethyl)benzyl] | H |
| CAP-188 | H | $CH_2C_6H_3-(CF_3)_2$ [2,4-bis(Trifluoromethyl)benzyl] |
| CAP-189 | $CH_2C_6H_3-(CF_3)_2$ [2,4- | $CH_2C_6H_3-(CF_3)_2$ [2,4- |

TABLE 7-continued

R₁ and R₂ groups for CAP-136 to CAP-210.

| Cap Structure Number | R₁ | R₂ |
|---|---|---|
| | bis(Trifluoromethyl)benzyl] | bis(Trifluoromethyl)benzyl] |
| CAP-190 | Si(C₆H₅)₂C₄H₉ (t-Butyldiphenylsilyl) | H |
| CAP-191 | H | Si(C₆H₅)₂C₄H₉ (t-Butyldiphenylsilyl) |
| CAP-192 | Si(C₆H₅)₂C₄H₉ (t-Butyldiphenylsilyl) | Si(C₆H₅)₂C₄H₉ (t-Butyldiphenylsilyl) |
| CAP-193 | CH₂CH₂CH=CH₂ (Homoallyl) | H |
| CAP-194 | H | CH₂CH₂CH=CH₂ (Homoallyl) |
| CAP-195 | CH₂CH₂CH=CH₂ (Homoallyl) | CH₂CH₂CH=CH₂ (Homoallyl) |
| CAP-196 | P(O)(OH)₂ (MP) | H |
| CAP-197 | H | P(O)(OH)₂ (MP) |
| CAP-198 | P(O)(OH)₂ (MP) | P(O)(OH)₂ (MP) |
| CAP-199 | P(S)(OH)₂ (Thio-MP) | H |
| CAP-200 | H | P(S)(OH)₂ (Thio-MP) |
| CAP-201 | P(S)(OH)₂ (Thio-MP) | P(S)(OH)₂ (Thio-MP) |
| CAP-202 | P(O)(CH₃)(OH) (Methylphophonate) | H |
| CAP-203 | H | P(O)(CH₃)(OH) (Methylphophonate) |
| CAP-204 | P(O)(CH₃)(OH) (Methylphophonate) | P(O)(CH₃)(OH) (Methylphophonate) |
| CAP-205 | PN(ⁱPr)₂(OCH₂CH₂CN) (Phosporamidite) | H |
| CAP-206 | H | PN(ⁱPr)₂(OCH₂CH₂CN) (Phosporamidite) |
| CAP-207 | PN(ⁱPr)₂(OCH₂CH₂CN) (Phosporamidite) | PN(ⁱPr)₂(OCH₂CH₂CN) (Phosporamidite) |
| CAP-208 | SO₂CH₃ (Methanesulfonic acid) | H |
| CAP-209 | H | SO₂CH₃ (Methanesulfonic acid) |
| CAP-210 | SO₂CH₃ (Methanesulfonic acid) | SO₂CH₃ (Methanesulfonic acid) |

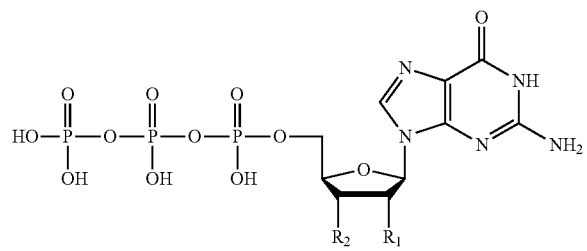

or where R₁ and R₂ are defined in Table 8:

TABLE 8

R₁ and R₂ groups for CAP-211 to 225.

| Cap Structure Number | R₁ | R₂ |
|---|---|---|
| CAP-211 | NH₂ (amino) | H |
| CAP-212 | H | NH₂ (amino) |
| CAP-213 | NH₂ (amino) | NH₂ (amino) |
| CAP-214 | N₃ (Azido) | H |
| CAP-215 | H | N₃ (Azido) |
| CAP-216 | N₃ (Azido) | N₃ (Azido) |
| CAP-217 | X (Halo: F, Cl, Br, I) | H |

TABLE 8-continued

R₁ and R₂ groups for CAP-211 to 225.

| Cap Structure Number | R₁ | R₂ |
|---|---|---|
| CAP-218 | H | X (Halo: F, Cl, Br, I) |
| CAP-219 | X (Halo: F, Cl, Br, I) | X (Halo: F, Cl, Br, I) |
| CAP-220 | SH (Thiol) | H |
| CAP-221 | H | SH (Thiol) |
| CAP-222 | SH (Thiol) | SH (Thiol) |
| CAP-223 | SCH₃ (Thiomethyl) | H |
| CAP-224 | H | SCH₃ (Thiomethyl) |
| CAP-225 | SCH₃ (Thiomethyl) | SCH₃ (Thiomethyl) |

In Table 7, "MOM" stands for methoxymethyl, "MEM" stands for methoxyethoxymethyl, "MTM" stands for methylthiomethyl, "BOM" stands for benzyloxymethyl and "MP" stands for monophosphonate.

In another non-limiting example, of the modified capping structure substrates CAP-112-CAP-225 could be added in the presence of vaccinia capping enzyme with a component to create enzymatic activity such as, but not limited to, S-adenosylmethionine (AdoMet), to form a modified cap for mRNA.

In one embodiment, the replacement of the sugar ring oxygen (that produced the carbocyclic ring) with a methylene moiety (CH₂) could create greater stability to the C—N bond against phosphorylases as the C—N bond is resistant to acid or enzymatic hydrolysis. The methylene moiety may also increase the stability of the triphosphate bridge moiety and thus increasing the stability of the mRNA. As a non-limiting example, the cap substrate structure for cap dependent translation may have the structure such as, but not limited to, CAP-014 and CAP-015 and/or the cap substrate structure for vaccinia mRNA capping enzyme such as, but not limited to, CAP-123 and CAP-124. In another example, CAP-112-CAP-122 and/or CAP-125-CAP-225, can be modified by replacing the sugar ring oxygen (that produced the carbocyclic ring) with a methylene moiety (CH₂).

In another embodiment, the triphophosphate bridge may be modified by the replacement of at least one oxygen with sulfur (thio), a borane (BH₃) moiety, a methyl group, an ethyl group, a methoxy group and/or combinations thereof. This modification could increase the stability of the mRNA towards decapping enzymes. As a non-limiting example, the cap substrate structure for cap dependent translation may have the structure such as, but not limited to, CAP-016-CAP-021 and/or the cap substrate structure for vaccinia mRNA capping enzyme such as, but not limited to, CAP-125-CAP-130. In another example, CAP-003-CAP-015, CAP-022-CAP-124 and/or CAP-131-CAP-225, can be modified on the triphosphate bridge by replacing at least one of the triphosphate bridge oxygens with sulfur (thio), a borane (BH₃) moiety, a methyl group, an ethyl group, a methoxy group and/or combinations thereof.

In one embodiment, CAP-001-134 and/or CAP-136-CAP-225 may be modified to be a thioguanosine analog similar to CAP-135. The thioguanosine analog may comprise additional modifications such as, but not limited to, a modification at the triphosphate moiety (e.g., thio, BH₃, CH₃, C₂H₅, OCH₃, S and S with OCH₃), a modification at the 2' and/or 3' positions of 6-thio guanosine as described herein and/or a replacement of the sugar ring oxygen (that produced the carbocyclic ring) as described herein.

In one embodiment, CAP-001-121 and/or CAP-123-CAP-225 may be modified to be a modified 5'-cap similar to CAP-122. The modified 5'-cap may comprise additional modifications such as, but not limited to, a modification at the triphosphate moiety (e.g., thio, $BH_3$, $CH_3$, $C_2H_5$, $OCH_3$, S and S with $OCH_3$), a modification at the 2' and/or 3' positions of 6-thio guanosine as described herein and/or a replacement of the sugar ring oxygen (that produced the carbocyclic ring) as described herein.

In one embodiment, the 5'-cap modification may be the attachment of biotin or conjugation at the 2' or 3' position of a GTP.

In another embodiment, the 5'-cap modification may include a $CF_2$ modified triphosphate moiety.

In another embodiment, the triphosphate bridge of any of the cap structures described herein may be replaced with a tetraphosphate or pentaphosphate bridge. Examples of tetraphosphate and pentaphosphate containing bridges and other cap modifications are described in Jemielity, J. et al. RNA 2003 9:1108-1122; Grudzien-Nogalska, E. et al. Methods Mol. Biol. 2013 969:55-72; and Grudzien, E. et al. RNA, 2004 10:1479-1487, each of which is incorporated herein by reference in its entirety.

Terminal Architecture Alterations: Stem Loop

In one embodiment, the nucleic acids of the present invention may include a stem loop such as, but not limited to, a histone stem loop. The stem loop may be a nucleotide sequence that is about 25 or about 26 nucleotides in length such as, but not limited to, SEQ ID NOs: 7-17 as described in International Patent Publication No. WO2013103659, incorporated herein by reference in its entirety. The histone stem loop may be located 3' relative to the coding region (e.g., at the 3' terminus of the coding region). As a non-limiting example, the stem loop may be located at the 3' end of a nucleic acid described herein.

In one embodiment, the stem loop may be located in the second terminal region. As a non-limiting example, the stem loop may be located within an untranslated region (e.g., 3'3'-UTR) in the second terminal region.

In one embodiment, the nucleic acid such as, but not limited to mRNA, which comprises the histone stem loop may be stabilized by the addition of at least one chain terminating nucleoside. Not wishing to be bound by theory, the addition of at least one chain terminating nucleoside may slow the degradation of a nucleic acid and thus can increase the half-life of the nucleic acid.

In one embodiment, the chain terminating nucleoside may be, but is not limited to, those described in International Patent Publication No. WO2013103659, incorporated herein by reference in its entirety. In another embodiment, the chain terminating nucleosides which may be used with the present invention includes, but is not limited to, 3'-deoxyadenosine (cordycepin), 3'-deoxyuridine, 3'-deoxycytidine, 3'-deoxyguanosine, 3'-deoxythymidine, 2',3'-dideoxynucleosides, such as 2',3'-dideoxyadenosine, 2',3'-dideoxyuridine, 2',3'-dideoxycytidine, 2',3'-dideoxyguanosine, 2',3'-dideoxythymidine, a 2'-deoxynucleoside, or a 2' or 3'-O-methylnucleoside.

In another embodiment, the nucleic acid such as, but not limited to mRNA, which comprises the histone stem loop may be stabilized by an alteration to the 3'-region of the nucleic acid that can prevent and/or inhibit the addition of oligio(U) (see e.g., International Patent Publication No. WO2013103659, incorporated herein by reference in its entirety).

In yet another embodiment, the nucleic acid such as, but not limited to mRNA, which comprises the histone stem loop may be stabilized by the addition of an oligonucleotide that terminates in a 3'-deoxynucleoside, 2',3'-dideoxynucleoside 3'-O-methyl nucleosides, 3'-O-ethyl nucleosides, 3'-arabinosides, and other alternative nucleosides known in the art and/or described herein.

In one embodiment, the nucleic acids of the present invention may include a histone stem loop, a polyA tail sequence and/or a 5'-cap structure. The histone stem loop may be before and/or after the polyA tail sequence. The nucleic acids comprising the histone stem loop and a polyA tail sequence may include a chain terminating nucleoside described herein.

In another embodiment, the nucleic acids of the present invention may include a histone stem loop and a 5'-cap structure. The 5'-cap structure may include, but is not limited to, those described herein and/or known in the art.

In one embodiment, the conserved stem loop region may comprise a miR sequence described herein. As a non-limiting example, the stem loop region may comprise the seed sequence of a miR sequence described herein. In another non-limiting example, the stem loop region may comprise a miR-122 seed sequence.

In another embodiment, the conserved stem loop region may comprise a miR sequence described herein and may also include a TEE sequence.

In one embodiment, the incorporation of a miR sequence and/or a TEE sequence changes the shape of the stem loop region which may increase and/or decrease translation. (see e.g, Kedde et al. A Pumilio-induced RNA structure switch in p27-3'-UTR controls miR-221 and miR-22 accessibility. Nature Cell Biology. 2010, herein incorporated by reference in its entirety).

In one embodiment, the alternative nucleic acids described herein may comprise at least one histone stem-loop and a polyA sequence or polyadenylation signal. Non-limiting examples of nucleic acid sequences encoding for at least one histone stem-loop and a polyA sequence or a polyadenylation signal are described in International Patent Publication No. WO2013120497, WO2013120629, WO2013120500, WO2013120627, WO2013120498, WO2013120626, WO2013120499 and WO2013120628, the contents of each of which are incorporated herein by reference in their entirety. In one embodiment, the nucleic acid encoding for a histone stem loop and a polyA sequence or a polyadenylation signal may code for a pathogen antigen or fragment thereof such as the nucleic acid sequences described in International Patent Publication No WO2013120499 and WO2013120628, the contents of both of which are incorporated herein by reference in their entirety. In another embodiment, the nucleic acid encoding for a histone stem loop and a polyA sequence or a polyadenylation signal may code for a therapeutic protein such as the nucleic acid sequences described in International Patent Publication No WO2013120497 and WO2013120629, the contents of both of which are incorporated herein by reference in their entirety. In one embodiment, the nucleic acid encoding for a histone stem loop and a polyA sequence or a polyadenylation signal may code for a tumor antigen or fragment thereof such as the nucleic acid sequences described in International Patent Publication No WO2013120500 and WO2013120627, the contents of both of which are incorporated herein by reference in their entirety. In another embodiment, the nucleic acid encoding for a histone stem loop and a polyA sequence or a polyadenylation signal may code for an allergenic antigen or an autoimmune self-antigen such as the nucleic acid sequences described in International Patent Publication No WO2013120498 and WO2013120626, the contents of both of which are incorporated herein by reference in their entirety.

Terminal Architecture Alterations: 3'-UTR and Triple Helices

In one embodiment, nucleic acids of the present invention may include a triple helix on the 3' end of the alternative nucleic acid, enhanced alternative RNA or ribonucleic acid. The 3' end of the nucleic acids of the present invention may include a triple helix alone or in combination with a Poly-A tail.

In one embodiment, the nucleic acid of the present invention may comprise at least a first and a second U-rich region, a conserved stem loop region between the first and second region and an A-rich region. The first and second U-rich region and the A-rich region may associate to form a triple helix on the 3' end of the nucleic acid. This triple helix may stabilize the nucleic acid, enhance the translational efficiency of the nucleic acid and/or protect the 3' end from degradation. Exemplary triple helices include, but are not limited to, the triple helix sequence of metastasis-associated lung adenocarcinoma transcript 1 (MALAT1), MEN-β and polyadenylated nuclear (PAN) RNA (See Wilusz et al., Genes & Development 2012 26:2392-2407; herein incorporated by reference in its entirety). In one embodiment, the 3' end of the alternative nucleic acids, enhanced alternative RNA or ribonucleic acids of the present invention comprises a first U-rich region comprising TTTTTCTTTT (SEQ ID NO: 1), a second U-rich region comprising TTTTGCTTTTT (SEQ ID NO: 2) or TTTTGCTTTT (SEQ ID NO: 3), an A-rich region comprising AAAAAGCAAAA (SEQ ID NO: 4). In another embodiment, the 3' end of the nucleic acids of the present invention comprises a triple helix formation structure comprising a first U-rich region, a conserved region, a second U-rich region and an A-rich region.

In one embodiment, the triple helix may be formed from the cleavage of a MALAT1 sequence prior to the cloverleaf structure. While not meaning to be bound by theory, MALAT1 is a long non-coding RNA which, when cleaved, forms a triple helix and a tRNA-like cloverleaf structure. The MALAT1 transcript then localizes to nuclear speckles and the tRNA-like cloverleaf localizes to the cytoplasm (Wilusz et al. Cell 2008 135(5): 919-932; incorporated herein by reference in its entirety).

As a non-limiting example, the terminal end of the nucleic acid of the present invention comprising the MALAT1 sequence can then form a triple helix structure, after RNaseP cleavage from the cloverleaf structure, which stabilizes the nucleic acid (Peart et al. *Non-mRNA 3' end formation: how the other half lives*; WIREs RNA 2013; incorporated herein by reference in its entirety).

In one embodiment, the nucleic acids or mRNA described herein comprise a MALAT1 sequence. In another embodiment, the nucleic acids or mRNA may be polyadenylated. In yet another embodiment, the nucleic acids or mRNA is not polyadenylated but has an increased resistance to degradation compared to unaltered nucleic acids or mRNA.

In one embodiment, the nucleic acids of the present invention may comprise a MALAT1 sequence in the second flanking region (e.g., the 3'-UTR). As a non-limiting example, the MALAT1 sequence may be human or mouse.

In another embodiment, the cloverleaf structure of the MALAT1 sequence may also undergo processing by RNaseZ and CCA adding enzyme to form a tRNA-like structure called mascRNA (MALAT1-associated small cytoplasmic RNA). As a non-limiting example, the mascRNA may encode a protein or a fragment thereof and/or may comprise a microRNA sequence. The mascRNA may comprise at least one chemical alteration described herein.

Terminal Architecture Alterations: Poly-A Tails

During RNA processing, a long chain of adenosine nucleotides (poly-A tail) is normally added to a messenger RNA (mRNA) molecules to increase the stability of the molecule. Immediately after transcription, the 3' end of the transcript is cleaved to free a 3' hydroxyl. Then poly-A polymerase adds a chain of adenosine nucleotides to the RNA. The process, called polyadenylation, adds a poly-A tail that is between 100 and 250 residues long.

Methods for the stabilization of RNA by incorporation of chain-terminating nucleosides at the 3'-terminus include those described in International Patent Publication No. WO2013103659, incorporated herein in its entirety.

Unique poly-A tail lengths may provide certain advantages to the alternative RNAs of the present invention.

Generally, the length of a poly-A tail of the present invention is greater than 10 nucleotides. In some embodiments, the poly-A tail is greater than 20 nucleotides. In some embodiments, the poly-A tail is greater than 30 nucleotides in length. In another embodiment, the poly-A tail is greater than 35 nucleotides in length. In another embodiment, the length of the poly-A tail is at least 40 nucleotides. In another embodiment, the length of the poly-A tail is at least 45 nucleotides. In another embodiment, the length of the poly-A tail is at least 55 nucleotides. In another embodiment, the length of the poly-A tail is at least 60 nucleotides. In another embodiment, the length of the poly-A tail is at least 70 nucleotides. In another embodiment, the length of the poly-A tail is at least 80 nucleotides. In another embodiment, the length of the poly-A tail is at least 90 nucleotides. In another embodiment, the length of the poly-A tail is at least 100 nucleotides. In another embodiment, the length of the poly-A tail is at least 120 nucleotides. In another embodiment, the length of the poly-A tail is at least 140 nucleotides. In another embodiment, the length of the poly-A tail is at least 160 nucleotides. In another embodiment, the length of the poly-A tail is at least 180 nucleotides. In another embodiment, the length of the poly-A tail is at least 200 nucleotides. In another embodiment, the length of the poly-A tail is at least 250 nucleotides. In another embodiment, the length of the poly-A tail is at least 300 nucleotides.

In another embodiment, the length of the mRNA is at least 350 nucleotides. In another embodiment, the length of the mRNA is at least 400 nucleotides. In another embodiment, the length of the mRNA is at least 450 nucleotides. In another embodiment, the length of the mRNA is at least 500 nucleotides. In another embodiment, the length of the mRNA is at least 600 nucleotides. In another embodiment, the length of the mRNA is at least 700 nucleotides. In another embodiment, the length of the mRNA is at least 800 nucleotides. In another embodiment, the length of the mRNA is at least 900 nucleotides. In another embodiment, the length of the mRNA is at least 1000 nucleotides. In another embodiment, the length of the mRNA is at least 1100 nucleotides. In another embodiment, the length of the mRNA is at least 1200 nucleotides. In another embodiment, the length of the mRNA is at least 1300 nucleotides. In another embodiment, the length of the mRNA is at least 1400 nucleotides. In another embodiment, the length of the mRNA is at least 1500 nucleotides. In another embodiment, the length of the mRNA is at least 1600 nucleotides. In another embodiment, the length of the mRNA is at least 1700 nucleotides. In another embodiment, the length of the mRNA is at least 1800 nucleotides. In another embodiment, the length of the mRNA is at least 1900 nucleotides. In another embodiment, the length of the mRNA is at least 2000 nucleotides. In another embodiment, the length of the mRNA is at least 2500 nucleotides. In another embodiment, the length of the mRNA is at least 3000 nucleotides.

In one embodiment, the poly-A tail may be 80 nucleotides, 120 nucleotides, 160 nucleotides in length on an alternative RNA molecule described herein.

In another embodiment, the poly-A tail may be 20, 40, 80, 100, 120, 140 or 160 nucleotides in length on an alternative RNA molecule described herein.

In one embodiment, the poly-A tail is designed relative to the length of the overall alternative RNA molecule. This design may be based on the length of the coding region of the alternative RNA, the length of a particular feature or region of the alternative RNA (such as the mRNA), or based on the length of the ultimate product expressed from the alternative RNA. When relative to any additional feature of the alternative RNA (e.g., other than the mRNA portion which includes the poly-A tail) the poly-A tail may be 10, 20, 30, 40, 50, 60, 70, 80, 90 or 100% greater in length than the additional feature. The poly-A tail may also be designed as a fraction of the alternative RNA to which it belongs. In this context, the poly-A tail may be 10, 20, 30, 40, 50, 60, 70, 80, or 90% or more of the total length of the construct or the total length of the construct minus the poly-A tail.

In one embodiment, engineered binding sites and/or the conjugation of nucleic acids or mRNA for Poly-A binding protein may be used to enhance expression. The engineered binding sites may be sensor sequences which can operate as binding sites for ligands of the local microenvironment of the nucleic acids and/or mRNA. As a non-limiting example, the nucleic acids and/or mRNA may comprise at least one engineered binding site to alter the binding affinity of Poly-A binding protein (PABP) and analogs thereof. The incorporation of at least one engineered binding site may increase the binding affinity of the PABP and analogs thereof.

Additionally, multiple distinct nucleic acids or mRNA may be linked together to the PABP (Poly-A binding protein) through the 3'-end using alternative nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection. As a non-limiting example, the transfection experiments may be used to evaluate the effect on PABP or analogs thereof binding affinity as a result of the addition of at least one engineered binding site.

In one embodiment, a polyA tail may be used to modulate translation initiation. While not wishing to be bound by theory, the polyA tail recruits PABP which in turn can interact with translation initiation complex and thus may be essential for protein synthesis.

In another embodiment, a polyA tail may also be used in the present invention to protect against 3'-5' exonuclease digestion.

In one embodiment, the nucleic acids or mRNA of the present invention are designed to include a polyA-G Quartet. The G-quartet is a cyclic hydrogen bonded array of four guanosine nucleotides that can be formed by G-rich sequences in both DNA and RNA. In this embodiment, the G-quartet is incorporated at the end of the poly-A tail. The resultant nucleic acid or mRNA may be assayed for stability, protein production and other parameters including half-life at various time points. It has been discovered that the polyA-G quartet results in protein production equivalent to at least 75% of that seen using a poly-A tail of 120 nucleotides alone.

In one embodiment, the nucleic acids or mRNA of the present invention may comprise a polyA tail and may be stabilized by the addition of a chain terminating nucleoside. The nucleic acids and/or mRNA with a polyA tail may further comprise a 5'-cap structure.

In another embodiment, the nucleic acids or mRNA of the present invention may comprise a polyA-G Quartet. The nucleic acids and/or mRNA with a polyA-G Quartet may further comprise a 5'-cap structure.

In one embodiment, the chain terminating nucleoside which may be used to stabilize the nucleic acid or mRNA comprising a polyA tail or polyA-G Quartet may be, but is not limited to, those described in International Patent Publication No. WO2013103659, incorporated herein by reference in its entirety. In another embodiment, the chain terminating nucleosides which may be used with the present invention includes, but is not limited to, 3'-deoxyadenosine (cordycepin), 3'-deoxyuridine, 3'-deoxycytidine, 3'-deoxyguanosine, 3'-deoxythymidine, 2',3'-dideoxynucleosides, such as 2',3'-dideoxyadenosine, 2',3'-dideoxyuridine, 2',3'-dideoxycytidine, 2',3'-dideoxyguanosine, 2',3'-dideoxythymidine, a 2'-deoxynucleoside, or a 2' or 3'-O-methylnucleoside.

In another embodiment, the nucleic acid such as, but not limited to mRNA, which comprise a polyA tail or a polyA-G Quartet may be stabilized by an alteration to the 3'-region of the nucleic acid that can prevent and/or inhibit the addition of oligio(U) (see e.g., International Patent Publication No. WO2013103659, incorporated herein by reference in its entirety).

In yet another embodiment, the nucleic acid such as, but not limited to mRNA, which comprise a polyA tail or a polyA-G Quartet may be stabilized by the addition of an oligonucleotide that terminates in a 3'-deoxynucleoside, 2',3'-dideoxynucleoside 3'-O-methylnucleosides, 3'-O-ethyl nucleosides, 3'-arabinosides, and other alternative nucleosides known in the art and/or described herein.

5'-UTR, 3'-UTR and Translation Enhancer Elements (TEEs)

In one embodiment, the 5'-UTR of the polynucleotides, primary constructs, alternative nucleic acids and/or mmRNA may include at least one translational enhancer polynucleotide, translation enhancer element, translational enhancer elements (collectively referred to as "TEE" s). As a non-limiting example, the TEE may be located between the transcription promoter and the start codon. The polynucleotides, primary constructs, alternative nucleic acids and/or mmRNA with at least one TEE in the 5'-UTR may include a cap at the 5'-UTR. Further, at least one TEE may be located in the 5'-UTR of polynucleotides, primary constructs, alternative nucleic acids and/or mmRNA undergoing cap-dependent or cap-independent translation.

The term "translational enhancer element" or "translation enhancer element" (herein collectively referred to as "TEE") refers to sequences that increase the amount of polypeptide or protein produced from an mRNA.

In one aspect, TEEs are conserved elements in the UTR which can promote translational activity of a nucleic acid such as, but not limited to, cap-dependent or cap-independent translation. The conservation of these sequences has been previously shown by Panek et al (Nucleic Acids Research, 2013, 1-10; incorporated herein by reference in its entirety) across 14 species including humans.

In one non-limiting example, the TEEs known may be in the 5'-leader of the Gtx homeodomain protein (Chappell et al., Proc. Natl. Acad. Sci. USA 101:9590-9594, 2004, incorporated herein by reference in their entirety).

In another non-limiting example, TEEs are disclosed as SEQ ID NOs: 1-35 in US Patent Publication No. US20090226470, SEQ ID NOs: 1-35 in US Patent Publication US20130177581, SEQ ID NOs: 1-35 in International Patent Publication No. WO2009075886, SEQ ID NOs: 1-5, and 7-645 in International Patent Publication No. WO2012009644, SEQ ID NO: 1 in International Patent Publication No. WO1999024595, SEQ ID NO: 1 in U.S. Pat. No. 6,310,197, and SEQ ID NO: 1 in U.S. Pat. No. 6,849,405, each of which is incorporated herein by reference in its entirety.

In yet another non-limiting example, the TEE may be an internal ribosome entry site (IRES), HCV-IRES or an IRES element such as, but not limited to, those described in U.S. Pat. No. 7,468,275, US Patent Publication Nos. US20070048776 and US20110124100 and International Patent Publication Nos. WO2007025008 and WO2001055369, each of which is incorporated herein by reference in its entirety. The IRES elements may include, but are not limited to, the Gtx sequences (e.g., Gtx9-nt, Gtx8-nt, Gtx7-nt) described by Chappell et al. (Proc. Natl. Acad. Sci. USA 101:9590-9594, 2004) and Zhou et al. (PNAS 102: 6273-6278, 2005) and in US Patent Publication Nos. US20070048776 and US20110124100 and International Patent Publication No. WO2007025008, each of which is incorporated herein by reference in its entirety.

"Translational enhancer polynucleotides" or "translation enhancer polynucleotide sequences" are polynucleotides which include one or more of the specific TEE exemplified herein and/or disclosed in the art (see e.g., U.S. Pat. No. 6,310,197, U.S. Pat. No. 6,849,405, U.S. Pat. No. 7,456,273, U.S. Pat. No. 7,183,395, US20090226470, US20070048776, US20110124100, US20090093049, US20130177581, WO2009075886, WO2007025008, WO2012009644, WO2001055371 WO1999024595, and EP2610341A1 and EP2610340A1; each of which is incorporated herein by reference in its entirety) or their variants, homologs or functional derivatives. One or multiple copies of a specific TEE can be present in the polynucleotides, primary constructs, alternative nucleic acids and/or mmRNA. The TEEs in the translational enhancer polynucleotides can be organized in one or more sequence segments. A sequence segment can harbor one or more of the specific TEEs exemplified herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the specific TEEs exemplified herein, identical or different number of copies of each of the specific TEEs, and/or identical or different organization of the TEEs within each sequence segment.

In one embodiment, the polynucleotides, primary constructs, alternative nucleic acids and/or mmRNA may include at least one TEE that is described in International Patent Publication No. WO1999024595, WO2012009644, WO2009075886, WO2007025008, WO1999024595, European Patent Publication No. EP2610341A1 and EP2610340A1, U.S. Pat. No. 6,310,197, U.S. Pat. No. 6,849,405, U.S. Pat. No. 7,456,273, U.S. Pat. No. 7,183,395, US Patent Publication No. US20090226470, US20110124100, US20070048776, US20090093049, and US20130177581 each of which is incorporated herein by reference in its entirety. The TEE may be located in the 5'-UTR of the polynucleotides, primary constructs, alternative nucleic acids and/or mmRNA.

In another embodiment, the polynucleotides, primary constructs, alternative nucleic acids and/or mmRNA may include at least one TEE that has at least 50%, at least 55%, at least 60%, at least 65%, at least 70%, at least 75%, at least 80%, at least 85%, at least 90%, at least 95% or at least 99% identity with the TEEs described in US Patent Publication Nos. US20090226470, US20070048776, US20130177581 and US20110124100, International Patent Publication No. WO1999024595, WO2012009644, WO2009075886 and WO2007025008, European Patent Publication No. EP2610341A1 and EP2610340A1, U.S. Pat. No. 6,310,197, U.S. Pat. No. 6,849,405, U.S. Pat. No. 7,456,273, U.S. Pat. No. 7,183,395, each of which is incorporated herein by reference in its entirety.

In one embodiment, the 5'-UTR of the polynucleotides, primary constructs, alternative nucleic acids and/or mmRNA may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 5'-UTR of the polynucleotides, primary constructs, alternative nucleic acids and/or mmRNA of the present invention may be the same or different TEE sequences. The TEE sequences may be in a pattern such as ABABAB or AAB-BAABBAABB or ABCABCABC or variants thereof repeated once, twice, or more than three times. In these patterns, each letter, A, B, or C represent a different TEE sequence at the nucleotide level.

In one embodiment, the 5'-UTR may include a spacer to separate two TEE sequences. As a non-limiting example, the spacer may be a 15 nucleotide spacer and/or other spacers known in the art. As another non-limiting example, the 5'-UTR may include a TEE sequence-spacer module repeated at least once, at least twice, at least 3 times, at least 4 times, at least 5 times, at least 6 times, at least 7 times, at least 8 times and at least 9 times or more than 9 times in the 5'-UTR.

In another embodiment, the spacer separating two TEE sequences may include other sequences known in the art which may regulate the translation of the polynucleotides, primary constructs, alternative nucleic acids and/or mmRNA of the present invention such as, but not limited to, miR sequences described herein (e.g., miR binding sites and miR seeds). As a non-limiting example, each spacer used to separate two TEE sequences may include a different miR sequence or component of a miR sequence (e.g., miR seed sequence).

In one embodiment, the TEE in the 5'-UTR of the polynucleotides, primary constructs, alternative nucleic acids and/or mmRNA of the present invention may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in US Patent Publication Nos. US20090226470, US20070048776, US20130177581 and US20110124100, International Patent Publication No. WO1999024595, WO2012009644, WO2009075886 and WO2007025008, European Patent Publication No. EP2610341A1 and EP2610340A1, U.S. Pat. No. 6,310,197, U.S. Pat. No. 6,849,405, U.S. Pat. No. 7,456,273, and U.S. Pat. No. 7,183,395 each of which is incorporated herein by reference in its entirety. In another embodiment, the TEE in the 5'-UTR of the polynucleotides, primary constructs, alternative nucleic acids and/or mmRNA of the present invention may include a 5-30 nucleotide fragment, a 5-25 nucleotide fragment, a 5-20 nucleotide fragment, a 5-15 nucleotide fragment, a 5-10 nucleotide fragment of the TEE sequences disclosed in US Patent Publication Nos. US20090226470, US20070048776, US20130177581 and U520110124100, International Patent Publication No. WO1999024595, WO2012009644, WO2009075886 and WO2007025008, European Patent Publication No. EP2610341A1 and EP2610340A1, U.S. Pat. No. 6,310,197, U.S. Pat. No. 6,849,405, U.S. Pat. No. 7,456,273, and U.S. Pat. No. 7,183,395; each of which is incorporated herein by reference in its entirety.

In one embodiment, the TEE in the 5'-UTR of the polynucleotides, primary constructs, alternative nucleic acids and/or mmRNA of the present invention may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in Chappell et al. (Proc. Natl. Acad. Sci. USA 101:9590-9594, 2004) and Zhou et al. (PNAS 102: 6273-6278, 2005), in Supplemental Table 1 and in Supplemental Table 2 disclosed by Wellensiek et al (Genome-wide profiling of human cap-independent translation-enhancing elements, Nature Methods, 2013; DOI:10.1038/NMETH.2522); each of which is herein incorporated by reference in its entirety. In another embodiment, the TEE in the 5'-UTR of the polynucleotides, primary constructs, alternative nucleic acids and/or mmRNA of the present invention may include a 5-30 nucleotide fragment, a 5-25 nucleotide fragment, a 5-20 nucleotide fragment, a 5-15 nucleotide fragment, a 5-10 nucleotide fragment of the TEE sequences disclosed in Chappell et al. (Proc. Natl. Acad. Sci. USA 101:9590-9594, 2004) and Zhou et al. (PNAS 102:6273-6278, 2005), in Supplemental Table 1 and in Supplemental Table 2 disclosed by Wellensiek et al (Genome-wide profiling of human cap-independent translation-enhancing elements, Nature Methods, 2013; DOI:10.1038/NMETH.2522); each of which is incorporated herein by reference in its entirety.

In one embodiment, the TEE used in the 5'-UTR of the polynucleotides, primary constructs, alternative nucleic acids and/or mm RNA of the present invention is an IRES sequence such as, but not limited to, those described in U.S. Pat. No. 7,468,275 and International Patent Publication No. WO2001055369, each of which is incorporated herein by reference in its entirety.

In one embodiment, the TEEs used in the 5'-UTR of the polynucleotides, primary constructs, alternative nucleic acids and/or mm RNA of the present invention may be identified by the methods described in US Patent Publication No. US20070048776 and US20110124100 and International Patent Publication Nos. WO2007025008 and WO2012009644, each of which is incorporated herein by reference in its entirety.

In another embodiment, the TEEs used in the 5'-UTR of the polynucleotides, primary constructs, alternative nucleic acids and/or mm RNA of the present invention may be a transcription regulatory element described in U.S. Pat. No. 7,456,273 and U.S. Pat. No. 7,183,395, US Patent Publication No. US20090093049, and International Publication No. WO2001055371, each of which is incorporated herein by reference in its entirety. The transcription regulatory elements may be identified by methods known in the art, such as, but not limited to, the methods described in U.S. Pat. No. 7,456,273 and U.S. Pat. No. 7,183,395, US Patent Publication No. US20090093049, and International Publication No. WO2001055371, each of which is incorporated herein by reference in its entirety.

In yet another embodiment, the TEE used in the 5'-UTR of the polynucleotides, primary constructs, alternative nucleic acids and/or mm RNA of the present invention is an oligonucleotide or portion thereof as described in U.S. Pat. No. 7,456,273 and U.S. Pat. No. 7,183,395, US Patent Publication No. US20090093049, and International Publication No. WO2001055371, each of which is incorporated herein by reference in its entirety.

The 5' UTR comprising at least one TEE described herein may be incorporated in a monocistronic sequence such as, but not limited to, a vector system or a nucleic acid vector. As a non-limiting example, the vector systems and nucleic acid vectors may include those described in U.S. Pat. No. 7,456,273 and U.S. Pat. No. 7,183,395, US Patent Publication No. US20070048776, US20090093049 and US20110124100 and International Patent Publication Nos. WO2007025008 and WO2001055371, each of which is incorporated herein by reference in its entirety.

In one embodiment, the TEEs described herein may be located in the 5'-UTR and/or the 3'-UTR of the polynucleotides, primary constructs, alternative nucleic acids and/or mmRNA. The TEEs located in the 3'-UTR may be the same and/or different than the TEEs located in and/or described for incorporation in the 5'-UTR.

In one embodiment, the 3'-UTR of the polynucleotides, primary constructs, alternative nucleic acids and/or mmRNA may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 3'-UTR of the polynucleotides, primary constructs, alternative nucleic acids and/or mmRNA of the present invention may be the same or different TEE sequences. The TEE sequences may be in a pattern such as ABABAB or AABBAABBAABB or ABCABCABC or variants thereof repeated once, twice, or more than three times. In these patterns, each letter, A, B, or C represent a different TEE sequence at the nucleotide level.

In one embodiment, the 3'-UTR may include a spacer to separate two TEE sequences. As a non-limiting example, the spacer may be a 15 nucleotide spacer and/or other spacers known in the art. As another non-limiting example, the 3'-UTR may include a TEE sequence-spacer module repeated at least once, at least twice, at least 3 times, at least 4 times, at least 5 times, at least 6 times, at least 7 times, at least 8 times and at least 9 times or more than 9 times in the 3'-UTR.

In another embodiment, the spacer separating two TEE sequences may include other sequences known in the art which may regulate the translation of the polynucleotides, primary constructs, alternative nucleic acids and/or mmRNA of the present invention such as, but not limited to, miR sequences described herein (e.g., miR binding sites and miR seeds). As a non-limiting example, each spacer used to separate two TEE sequences may include a different miR sequence or component of a miR sequence (e.g., miR seed sequence).

In one embodiment, the incorporation of a miR sequence and/or a TEE sequence changes the shape of the stem loop region which may increase and/or decrease translation. (see e.g., Kedde et al. A Pumilio-induced RNA structure switch in p27-3'-UTR controls miR-221 and miR-22 accessibility. Nature Cell Biology. 2010, herein incorporated by reference in its entirety).

Heterologous 5'-UTRs

A 5' UTR may be provided as a flanking region to the alternative nucleic acids (mRNA), enhanced alternative RNA or ribonucleic acids of the invention. 5'-UTR may be homologous or heterologous to the coding region found in the alternative nucleic acids (mRNA), enhanced alternative RNA or ribonucleic acids of the invention. Multiple 5' UTRs may be included in the flanking region and may be the same or of different sequences. Any portion of the flanking regions, including none, may be codon optimized and any may independently contain one or more different structural or chemical alterations, before and/or after codon optimization.

Shown in Lengthy Table 21 in U.S. Provisional Application No. 61/775,509, and in Lengthy Table 21 and in Table 22 in U.S. Provisional Application No. 61/829,372, the contents of each of which are incorporated herein by reference in their entirety, is a listing of the start and stop site of the alternative nucleic acids (mRNA), enhanced alternative RNA or ribonucleic acids of the invention. In Table 21 each 5'-UTR (5'-UTR-005 to 5'-UTR 68511) is identified by its start and stop site relative to its native or wild-type (homologous) transcript (ENST; the identifier used in the ENSEMBL database).

To alter one or more properties of the polynucleotides, primary constructs or mmRNA of the invention, 5'-UTRs which are heterologous to the coding region of the alternative nucleic acids (mRNA), enhanced alternative RNA or ribonucleic acids of the invention are engineered into compounds of the invention. The alternative nucleic acids (mRNA), enhanced alternative RNA or ribonucleic acids are then administered to cells, tissue or organisms and outcomes such as protein level, localization and/or half-life are measured to evaluate the beneficial effects the heterologous 5'-UTR may have on the alternative nucleic acids (mRNA), enhanced alternative RNA or ribonucleic acids of the invention. Variants of the 5' UTRs may be utilized wherein one or more nucleotides are added or removed to the termini, including A, T, C or G. 5'-UTRs may also be codon-optimized or altered in any manner described herein.

Incorporating microRNA Binding Sites

In one embodiment, alternative nucleic acids (mRNA), enhanced alternative RNA or ribonucleic acids of the invention would not only encode a polypeptide but also a sensor sequence. Sensor sequences include, for example, microRNA binding sites, transcription factor binding sites, structured mRNA sequences and/or motifs, artificial binding sites engineered to act as pseudo-receptors for endogenous nucleic acid binding molecules. Non-limiting examples, of polynucleotides comprising at least one sensor sequence are described in co-pending and co-owned U.S. Provisional Patent Application No. 61/753,661, filed Jan. 17, 2013, U.S. Provisional Patent Application No. 61/754,159, filed Jan. 18, 2013, U.S. Provisional Patent Application No. 61/781,097, filed Mar. 14, 2013, U.S. Provisional Patent Application No. 61/829,334, filed May 31, 2013, U.S. Provisional Patent Application No. 61/839,893, filed Jun. 27, 2013, U.S. Provisional Patent Application No. 61/842,733, filed Jul. 3, 2013, and U.S. Provisional Patent Application No. 61/857,304, filed Jul. 23, 2013, the contents of each of which are incorporated herein by reference in their entirety.

In one embodiment, microRNA (miRNA) profiling of the target cells or tissues is conducted to determine the presence or absence of miRNA in the cells or tissues.

microRNAs (or miRNA) are 19-25 nucleotide long non-coding RNAs that bind to the 3'UTR of nucleic acid molecules and down-regulate gene expression either by reducing nucleic acid molecule stability or by inhibiting translation. The alternative nucleic acids (mRNA), enhanced alternative RNA or ribonucleic acids of the invention may comprise one or more microRNA target sequences, microRNA sequences, or microRNA seeds. Such sequences may correspond to any known microRNA such as those taught in US Publication US2005/0261218 and US Publication US2005/0059005, the contents of which are incorporated herein by reference in their entirety.

A microRNA sequence comprises a "seed" region, i.e., a sequence in the region of positions 2-8 of the mature microRNA, which sequence has perfect Watson-Crick complementarity to the miRNA target sequence. A microRNA seed may comprise positions 2-8 or 2-7 of the mature microRNA. In some embodiments, a microRNA seed may comprise 7 nucleotides (e.g., nucleotides 2-8 of the mature microRNA), wherein the seed-complementary site in the corresponding miRNA target is flanked by an adenosine (A) opposed to microRNA position 1. In some embodiments, a microRNA seed may comprise 6 nucleotides (e.g., nucleotides 2-7 of the mature microRNA), wherein the seed-complementary site in the corresponding miRNA target is flanked by an adenosine (A) opposed to microRNA position 1. See for example, Grimson A, Farh K K, Johnston W K, Garrett-Engele P, Lim L P, Bartel D P; Mol Cell. 2007 Jul. 6; 27(1):91-105. The bases of the microRNA seed have complete complementarity with the target sequence. By engineering microRNA target sequences into the 3'UTR of nucleic acids or mRNA of the invention one can target the molecule for degradation or reduced translation, provided the microRNA in question is available. This process will reduce the hazard of off target effects upon nucleic acid molecule delivery. Identification of microRNA, microRNA target regions, and their expression patterns and role in biology have been reported (Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

For example, if the mRNA is not intended to be delivered to the liver but ends up there, then miR-122, a microRNA abundant in liver, can inhibit the expression of the gene of interest if one or multiple target sites of miR-122 are engineered into the 3'UTR of the alternative nucleic acids, enhanced alternative RNA or ribonucleic acids. Introduction of one or multiple binding sites for different microRNA can be engineered to further decrease the longevity, stability, and protein translation of an alternative nucleic acids, enhanced alternative RNA or ribonucleic acids. As used herein, the term "microRNA site" refers to a microRNA target site or a microRNA recognition site, or any nucleotide sequence to which a microRNA binds or associates. It should be understood that "binding" may follow traditional Watson-Crick hybridization rules or may reflect any stable association of the microRNA with the target sequence at or adjacent to the microRNA site.

Conversely, for the purposes of the alternative nucleic acids, enhanced alternative RNA or ribonucleic acids of the present invention, microRNA binding sites can be engineered out of (i.e. removed from) sequences in which they naturally occur in order to increase protein expression in specific tissues. For example, miR-122 binding sites may be removed to improve protein expression in the liver.

In one embodiment, the alternative nucleic acids, enhanced alternative RNA or ribonucleic acids of the present invention may include at least one miRNA-binding site in the 3'-UTR in order to direct cytotoxic or cytoprotective mRNA therapeutics to specific cells such as, but not limited to, normal and/or cancerous cells (e.g., HEP3B or SNU449).

In another embodiment, the alternative nucleic acids, enhanced alternative RNA or ribonucleic acids of the present invention may include three miRNA-binding sites in the 3'-UTR in order to direct cytotoxic or cytoprotective mRNA therapeutics to specific cells such as, but not limited to, normal and/or cancerous cells (e.g., HEP3B or SNU449).

Regulation of expression in multiple tissues can be accomplished through introduction or removal or one or several microRNA binding sites. The decision of removal or insertion of microRNA binding sites, or any combination, is dependent on microRNA expression patterns and their profilings in diseases.

Examples of tissues where microRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Specifically, microRNAs are known to be differentially expressed in immune cells (also called hematopoietic cells), such as antigen presenting cells (APCs) (e.g. dendritic cells and macrophages), macrophages, monocytes, B lymphocytes, T lymphocytes, granuocytes, natural killer cells, etc. Immune cell specific microRNAs are involved in immunogenicity, autoimmunity, the immune-response to infection, inflammation, as well as unwanted immune response after gene therapy and tissue/organ transplantation. Immune cells specific microRNAs also regulate many aspects of development, proliferation, differentiation and apoptosis of hematopoietic cells (immune cells). For example, miR-142 and miR-146 are exclusively expressed in the immune cells, particularly abundant in myeloid dendritic cells. It was demonstrated in the art that the immune response to exogenous nucleic acid molecules was shut-off by adding miR-142 binding sites to the 3'-UTR of the delivered gene construct, enabling more stable gene transfer in tissues and cells. miR-142 efficiently degrades the exogenous mRNA in antigen presenting cells and suppresses cytotoxic elimination of transduced cells (Annoni A et al., blood, 2009, 114, 5152-5161; Brown B D, et al., Nat med. 2006, 12(5), 585-591; Brown B D, et al., blood, 2007, 110(13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing the miR-142 binding site into the 3'-UTR of a polypeptide of the present invention can selectively repress the gene expression in the antigen presenting cells through miR-142 mediated mRNA degradation, limiting antigen presentation in APCs (e.g. dendritic cells) and thereby preventing antigen-mediated immune response after the delivery of the polynucleotides. The polynucleotides are therefore stably expressed in target tissues or cells without triggering cytotoxic elimination.

In one embodiment, microRNAs binding sites that are known to be expressed in immune cells, in particular, the antigen presenting cells, can be engineered into the polynucleotide to suppress the expression of the sensor-signal polynucleotide in APCs through microRNA mediated RNA degradation, subduing the antigen-mediated immune response, while the expression of the polynucleotide is maintained in non-immune cells where the immune cell specific microRNAs are not expressed. For example, to prevent the immunogenic reaction caused by a liver specific protein expression, the miR-122 binding site can be removed and the miR-142 (and/or mirR-146) binding sites can be engineered into the 3-UTR of the polynucleotide.

To further drive the selective degradation and suppression of mRNA in APCs and macrophage, the polynucleotide may include another negative regulatory element in the 3-UTR, either alone or in combination with mir-142 and/or mir-146 binding sites. As a non-limiting example, one regulatory element is the Constitutive Decay Elements (CDEs).

Immune cells specific microRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p, miR-30e-3p, miR-30e-5p, miR-331-5p, miR-339-3p, miR-339-5p, miR-345-3p, miR-345-5p, miR-346, miR-34a-3p, miR-34a-5p, miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p and miR-99b-5p. Furthermore, novel miroRNAs are discovered in the immune cells in the art through micro-array hybridization and microtome analysis (Jima D D et al, Blood, 2010, 116:e118-e127; Vaz C et al., BMC Genomics, 2010, 11, 288, the content of each of which is incorporated herein by reference in its entirety.)

MicroRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, miR-939-5p. MicroRNA binding sites from any liver specific microRNA can be introduced to or removed from the polynucleotides to regulate the expression of the polynucleotides in the liver. Liver specific microRNAs binding sites can be engineered alone or further in combination with immune cells (e.g. APCs) microRNA binding sites in order to prevent immune reaction against protein expression in the liver.

MicroRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, miR-381-5p. MicroRNA binding sites from any lung specific microRNA can be introduced to or removed from the polynucleotide to regulate the expression of the polynucleotide in the lung. Lung specific microRNAs binding sites can be engineered alone or further in combination with immune cells (e.g. APCs) microRNA binding sites in order to prevent an immune reaction against protein expression in the lung.

MicroRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-3p, miR-499b-5p, miR-744-3p, miR-744-5p, miR-92b-3p and miR-92b-5p. MicroRNA binding sites from any heart specific microRNA can be introduced to or removed from the polynucleotides to regulate the expression of the polynucleotides in the heart. Heart specific microRNAs binding sites can be engineered alone or further in combination with immune cells (e.g. APCs) microRNA binding sites to prevent an immune reaction against protein expression in the heart.

MicroRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p and miR-9-5p. MicroRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, miR-657. MicroRNA binding sites from any CNS specific microRNA can be introduced to or removed from the polynucleotides to regulate the expression of the polynucleotide in the nervous system. Nervous system specific microRNAs binding sites can be engineered alone or further in combination with immune cells (e.g. APCs) microRNA binding sites in order to prevent immune reaction against protein expression in the nervous system.

MicroRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p and miR-944. MicroRNA binding sites from any pancreas specific microRNA can be introduced to or removed from the polynucleotide to regulate the expression of the polynucleotide in the pancreas. Pancreas specific microRNAs binding sites can be engineered alone or further in combination with immune cells (e.g. APCs) microRNA binding sites in order to prevent an immune reaction against protein expression in the pancreas.

MicroRNAs that are known to be expressed in the kidney further include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p and miR-562. MicroRNA binding sites from any kidney specific microRNA can be introduced to or removed from the polynucleotide to regulate the expression of the polynucleotide in the kidney. Kidney specific microRNAs binding sites can be engineered alone or further in combination with immune cells (e.g. APCs) microRNA binding sites to prevent an immune reaction against protein expression in the kidney.

MicroRNAs that are known to be expressed in the muscle further include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p and miR-25-5p. MicroRNA binding sites from any muscle specific microRNA can be introduced to or removed from the polynucleotide to regulate the expression of the polynucleotide in the muscle. Muscle specific microRNAs binding sites can be engineered alone or further in combination with immune cells (e.g. APCs) microRNA binding sites to prevent an immune reaction against protein expression in the muscle.

MicroRNAs are differentially expressed in different types of cells, such as endothelial cells, epithelial cells and adipocytes. For example, microRNAs that are expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p and miR-92b-5p. Many novel microRNAs are discovered in endothelial cells from deep-sequencing analysis (Voellenkle C et al., RNA, 2012, 18, 472-484, herein incorporated by reference in its entirety) microRNA binding sites from any endothelial cell specific microRNA can be introduced to or removed from the polynucleotide to modulate the expression of the polynucleotide in the endothelial cells in various conditions.

For further example, microRNAs that are expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells; let-7 family, miR-133a, miR-133b, miR-126 specific in lung epithelial cells; miR-382-3p, miR-382-5p specific in renal epithelial cells and miR-762 specific in corneal epithelial cells. MicroRNA binding sites from any epithelial cell specific MicroRNA can be introduced to or removed from the polynucleotide to modulate the expression of the polynucleotide in the epithelial cells in various conditions.

In addition, a large group of microRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008, 18, 610-621; Yoo J K et al., Stem Cells Dev. 2012, 21(11), 2049-2057, each of which is herein incorporated by reference in its entirety). MicroRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-548l, miR-548m, miR-548n, miR-5480-3p, miR-5480-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel microRNAs are discovered by deep sequencing in human embryonic stem cells (Morin R D et al., Genome Res, 2008, 18, 610-621; Goff L A et al., PLoS One, 2009, 4:e7192; Bar M et al., Stem cells, 2008, 26, 2496-2505, the content of each of which is incorporated herein by references in its entirety).

In one embodiment, the binding sites of embryonic stem cell specific microRNAs can be included in or removed from the 3-UTR of the polynucleotide to modulate the development and/or differentiation of embryonic stem cells, to inhibit the senescence of stem cells in a degenerative condition (e.g. degenerative diseases), or to stimulate the senescence and apoptosis of stem cells in a disease condition (e.g. cancer stem cells).

Many microRNA expression studies are conducted in the art to profile the differential expression of microRNAs in various cancer cells/tissues and other diseases. Some microRNAs are abnormally over-expressed in certain cancer cells and others are under-expressed. For example, microRNAs are differentially expressed in cancer cells (WO2008/154098, US2013/0059015, US2013/0042333, WO2011/157294); cancer stem cells (US2012/0053224); pancreatic cancers and diseases (US2009/0131348, US2011/0171646, US2010/0286232, U.S. Pat. No. 8,389,210); asthma and inflammation (U.S. Pat. No. 8,415,096); prostate cancer (US2013/0053264); hepatocellular carcinoma (WO2012/151212, US2012/0329672, WO2008/054828, U.S. Pat. No. 8,252,538); lung cancer cells (WO2011/076143, WO2013/033640, WO2009/070653, US2010/0323357); cutaneous T cell lymphoma (WO2013/011378); colorectal cancer cells (WO2011/0281756, WO2011/076142); cancer positive lymph nodes (WO2009/100430, US2009/0263803); nasopharyngeal carcinoma (EP2112235); chronic obstructive pulmonary disease (US2012/0264626, US2013/0053263); thyroid cancer (WO2013/066678); ovarian cancer cells US2012/0309645, WO2011/095623); breast cancer cells (WO2008/154098, WO2007/081740, US2012/0214699), leukemia and lymphoma (WO2008/073915, US2009/0092974, US2012/0316081, US2012/0283310, WO2010/018563, the content of each of which is incorporated herein by reference in its entirety.)

As a non-limiting example, microRNA sites that are over-expressed in certain cancer and/or tumor cells can be removed from the 3-UTR of the polynucleotide encoding the polypeptide of interest, restoring the expression suppressed by the over-expressed microRNAs in cancer cells, thus ameliorating the corresponsive biological function, for instance, transcription stimulation and/or repression, cell cycle arrest, apoptosis and cell death. Normal cells and tissues, wherein microRNAs expression is not up-regulated, will remain unaffected.

MicroRNA can also regulate complex biological processes such as angiogenesis (miR-132) (Anand and Cheresh Curr Opin Hematol 2011 18:171-176). In the alternative nucleic acids, enhanced alternative RNA or ribonucleic acids of the invention, binding sites for microRNAs that are involved in such processes may be removed or introduced, in order to tailor the expression of the alternative nucleic acids, enhanced alternative RNA or ribonucleic acids expression to biologically relevant cell types or to the context of relevant biological processes. In this context, the mRNA are defined as auxotrophic mRNA.

MicroRNA gene regulation may be influenced by the sequence surrounding the microRNA such as, but not limited to, the species of the surrounding sequence, the type of sequence (e.g., heterologous, homologous and artificial), regulatory elements in the surrounding sequence and/or structural elements in the surrounding sequence. The microRNA may be influenced by the 5'-UTR and/or the 3'-UTR. As a non-limiting example, a non-human 3'-UTR may increase the regulatory effect of the microRNA sequence on the expression of a polypeptide of interest compared to a human 3'-UTR of the same sequence type.

In one embodiment, other regulatory elements and/or structural elements of the 5'-UTR can influence microRNA mediated gene regulation. One example of a regulatory element and/or structural element is a structured IRES (Internal Ribosome Entry Site) in the 5'-UTR, which is necessary for the binding of translational elongation factors to initiate protein translation. EIF4A2 binding to this secondarily structured element in the 5'-UTR is necessary for microRNA mediated gene expression (Meijer H A et al., Science, 2013, 340, 82-85, herein incorporated by reference in its entirety). The alternative nucleic acids, enhanced alternative RNA or ribonucleic acids of the invention can further be alternative to include this structured 5'-UTR in order to enhance microRNA mediated gene regulation.

At least one microRNA site can be engineered into the 3' UTR of the alternative nucleic acids, enhanced alternative RNA or ribonucleic acids of the present invention. In this context, at least two, at least three, at least four, at least five, at least six, at least seven, at least eight, at least nine, at least ten or more microRNA sites may be engineered into the 3' UTR of the ribonucleic acids of the present invention. In one embodiment, the microRNA sites incorporated into the alternative nucleic acids, enhanced alternative RNA or ribonucleic acids may be the same or may be different microRNA sites. In another embodiment, the microRNA sites incorporated into the alternative nucleic acids, enhanced alternative RNA or ribonucleic acids may target the same or different tissues in the body. As a non-limiting example, through the introduction of tissue-, cell-type-, or disease-specific microRNA binding sites in the 3' UTR of an alternative nucleic acid mRNA, the degree of expression in specific cell types (e.g. hepatocytes, myeloid cells, endothelial cells, cancer cells, etc.) can be reduced.

In one embodiment, a microRNA site can be engineered near the 5' terminus of the 3'-UTR, about halfway between the 5' terminus and 3'terminus of the 3'-UTR and/or near the 3'terminus of the 3'-UTR. As a non-limiting example, a microRNA site may be engineered near the 5' terminus of the 3'-UTR and about halfway between the 5' terminus and 3'terminus of the 3'-UTR. As another non-limiting example, a microRNA site may be engineered near the 3'terminus of the 3'-UTR and about halfway between the 5' terminus and 3'terminus of the 3'-UTR. As yet another non-limiting example, a microRNA site may be engineered near the 5' terminus of the 3'-UTR and near the 3' terminus of the 3'-UTR.

In another embodiment, a 3'-UTR can comprise 4 microRNA sites. The microRNA sites may be complete microRNA binding sites, microRNA seed sequences and/or microRNA binding site sequences without the seed sequence.

In one embodiment, a nucleic acid of the invention may be engineered to include at least one microRNA in order to dampen the antigen presentation by antigen presenting cells. The microRNA may be the complete microRNA sequence, the microRNA seed sequence, the microRNA sequence without the seed or a combination thereof. As a non-limiting example, the microRNA incorporated into the nucleic acid may be specific to the hematopoietic system. As another non-limiting example, the microRNA incorporated into the nucleic acid of the invention to dampen antigen presentation is miR-142-3p.

In one embodiment, a nucleic acid may be engineered to include microRNA sites which are expressed in different tissues of a subject. As a non-limiting example, an alternative nucleic acid, enhanced alternative RNA or ribonucleic acid of the present invention may be engineered to include miR-192 and miR-122 to regulate expression of the alternative nucleic acid, enhanced alternative RNA or ribonucleic acid in the liver and kidneys of a subject. In another embodiment, an alternative nucleic acid, enhanced alternative RNA or ribonucleic acid may be engineered to include more than one microRNA sites for the same tissue. For example, an alternative nucleic acid, enhanced alternative RNA or ribonucleic acid of the present invention may be engineered to include miR-17-92 and miR-126 to regulate expression of the alternative nucleic acid, enhanced alternative RNA or ribonucleic acid in endothelial cells of a subject.

In one embodiment, the therapeutic window and or differential expression associated with the target polypeptide encoded by the alternative nucleic acid, enhanced alternative RNA or ribonucleic acid encoding a signal (also referred to herein as a polynucleotide) of the invention may be altered. For example, polynucleotides may be designed whereby a death signal is more highly expressed in cancer cells (or a survival signal in a normal cell) by virtue of the miRNA signature of those cells. Where a cancer cell expresses a lower level of a particular miRNA, the polynucleotide encoding the binding site for that miRNA (or miRNAs) would be more highly expressed. Hence, the target polypeptide encoded by the polynucleotide is selected as a protein which triggers or induces cell death. Neighboring noncancer cells, harboring a higher expression of the same miRNA would be less affected by the encoded death signal as the polynucleotide would be expressed at a lower level due to the effects of the miRNA binding to the binding site or "sensor" encoded in the 3'-UTR. Conversely, cell survival or cytoprotective signals may be delivered to tissues containing cancer and non-cancerous cells where a miRNA has a higher expression in the cancer cells—the result being a lower survival signal to the cancer cell and a larger survival signature to the normal cell. Multiple polynucleotides may be designed and administered having different signals according to the previous paradigm.

In one embodiment, the expression of a nucleic acid may be controlled by incorporating at least one sensor sequence in the nucleic acid and formulating the nucleic acid. As a non-limiting example, a nucleic acid may be targeted to an orthotopic tumor by having a nucleic acid incorporating a miR-122 binding site and formulated in a lipid nanoparticle comprising a cationic lipid such as DLin-MC3-DMA.

According to the present invention, the polynucleotides may be altered as to avoid the deficiencies of other polypeptide-encoding molecules of the art. Hence, in this embodiment the polynucleotides are referred to as alternative polynucleotides.

Through an understanding of the expression patterns of microRNA in different cell types, alternative nucleic acids, enhanced alternative RNA or ribonucleic acids such as polynucleotides can be engineered for more targeted expression in specific cell types or only under specific biological conditions. Through introduction of tissue-specific microRNA binding sites, alternative nucleic acids, enhanced alternative RNA or ribonucleic acids, could be designed that would be optimal for protein expression in a tissue or in the context of a biological condition.

Transfection experiments can be conducted in relevant cell lines, using engineered alternative nucleic acids, enhanced alternative RNA or ribonucleic acids and protein production can be assayed at various time points post-transfection. For example, cells can be transfected with different microRNA binding site-engineering nucleic acids or mRNA and by using an ELISA kit to the relevant protein and assaying protein produced at 6 hr, 12 hr, 24 hr, 48 hr, 72 hr and 7 days post-transfection. In vivo experiments can also be conducted using microRNA-binding site-engineered molecules to examine changes in tissue-specific expression of formulated alternative nucleic acids, enhanced alternative RNA or ribonucleic acids.

Non-limiting examples of cell lines which may be useful in these investigations include those from ATCC (Manassas, Va.) including MRC-5, A549, T84, NCI-H2126 [H2126], NCI-H1688 [H1688], WI-38, WI-38 VA-13 subline 2RA, WI-26 VA4, C3A [HepG2/C3A, derivative of Hep G2 (ATCC HB-8065)], THLE-3, H69AR, NCI-H292 [H292], CFPAC-1, NTERA-2 cl.D1 [NT2/D1], DMS 79, DMS 53, DMS 153, DMS 114, MSTO-211H, SW 1573 [SW-1573, SW1573], SW 1271 [SW-1271, SW1271], SHP-77, SNU-398, SNU-449, SNU-182, SNU-475, SNU-387, SNU-423, NL20, NL20-TA [NL20T-A], THLE-2, HBE135-E6E7, HCC827, HCC4006, NCI-H23 [H23], NCI-H1299, NCI-H187 [H187], NCI-H358 [H-358, H358], NCI-H378

[H378], NCI-H522 [H522], NCI-H526 [H526], NCI-H727 [H727], NCI-H810 [H810], NCI-H889 [H889], NCI-H1155 [H1155], NCI-H1404 [H1404], NCI-N87 [N87], NCI-H196 [H196], NCI-H211 [H211], NCI-H220 [H220], NCI-H250 [H250], NCI-H524 [H524], NCI-H647 [H647], NCI-H650 [H650], NCI-H711 [H711], NCI-H719 [H719], NCI-H740 [H740], NCI-H748 [H748], NCI-H774 [H774], NCI-H838 [H838], NCI-H841 [H841], NCI-H847 [H847], NCI-H865 [H865], NCI-H920 [H920], NCI-H1048 [H1048], NCI-H1092 [H1092], NCI-H1105 [H1105], NCI-H1184 [H1184], NCI-H1238 [H1238], NCI-H1341 [H1341], NCI-H1385 [H1385], NCI-H1417 [H1417], NCI-H1435 [H1435], NCI-H1436 [H1436], NCI-H1437 [H1437], NCI-H1522 [H1522], NCI-H1563 [H1563], NCI-H1568 [H1568], NCI-H1573 [H1573], NCI-H1581 [H1581], NCI-H1618 [H1618], NCI-H1623 [H1623], NCI-H1650 [H-1650, H1650], NCI-H1651 [H1651], NCI-H1666 [H-1666, H1666], NCI-H1672 [H1672], NCI-H1693 [H1693], NCI-H1694 [H1694], NCI-H1703 [H1703], NCI-H1734 [H-1734, H1734], NCI-H1755 [H1755], NCI-H1755 [H1755], NCI-H1770 [H1770], NCI-H1793 [H1793], NCI-H1836 [H1836], NCI-H1838 [H1838], NCI-H1869 [H1869], NCI-H1876 [H1876], NCI-H1882 [H1882], NCI-H1915 [H1915], NCI-H1930 [H1930], NCI-H1944 [H1944], NCI-H1975 [H-1975, H1975], NCI-H1993 [H1993], NCI-H2023 [H2023], NCI-H2029 [H2029], NCI-H2030 [H2030], NCI-H2066 [H2066], NCI-H2073 [H2073], NCI-H2081 [H2081], NCI-H2085 [H2085], NCI-H2087 [H2087], NCI-H2106 [H2106], NCI-H2110 [H2110], NCI-H2135 [H2135], NCI-H2141 [H2141], NCI-H2171 [H2171], NCI-H2172 [H2172], NCI-H2195 [H2195], NCI-H2196 [H2196], NCI-H2198 [H2198], NCI-H2227 [H2227], NCI-H2228 [H2228], NCI-H2286 [H2286], NCI-H2291 [H2291], NCI-H2330 [H2330], NCI-H2342 [H2342], NCI-H2347 [H2347], NCI-H2405 [H2405], NCI-H2444 [H2444], UMC-11, NCI-H64 [H64], NCI-H735 [H735], NCI-H735 [H735], NCI-H1963 [H1963], NCI-H2107 [H2107], NCI-H2108 [H2108], NCI-H2122 [H2122], Hs 573.T, Hs 573.Lu, PLC/PRF/5, BEAS-2B, Hep G2, Tera-1, Tera-2, NCI-H69 [H69], NCI-H128 [H128], ChaGo-K-1, NCI-H446 [H446], NCI-H209 [H209], NCI-H146 [H146], NCI-H441 [H441], NCI-H82 [H82], NCI-H460 [H460], NCI-H596 [H596], NCI-H676B [H67613], NCI-H345 [H345], NCI-H820 [H820], NCI-H520 [H520], NCI-H661 [H661], NCI-H510A [H510A, NCI-H510], SK-HEP-1, A-427, Calu-1, Calu-3, Calu-6, SK-LU-1, SK-MES-1, SW 900 [SW-900, SW900], Malme-3M, and Capan-1.

In some embodiments, alternative messenger RNA can be designed to incorporate microRNA binding region sites that either have 100% identity to known seed sequences or have less than 100% identity to seed sequences. The seed sequence can be partially mutated to decrease microRNA binding affinity and as such result in reduced downmodulation of that mRNA transcript. In essence, the degree of match or mis-match between the target mRNA and the microRNA seed can act as a rheostat to more finely tune the ability of the microRNA to modulate protein expression. In addition, mutation in the non-seed region of a microRNA binding site may also impact the ability of a microRNA to modulate protein expression.

In one embodiment, a miR sequence may be incorporated into the loop of a stem loop.

In another embodiment, a miR seed sequence may be incorporated in the loop of a stem loop and a miR binding site may be incorporated into the 5' or 3' stem of the stem loop.

In one embodiment, a TEE may be incorporated on the 5'end of the stem of a stem loop and a miR seed may be incorporated into the stem of the stem loop. In another embodiment, a TEE may be incorporated on the 5'end of the stem of a stem loop, a miR seed may be incorporated into the stem of the stem loop and a miR binding site may be incorporated into the 3'end of the stem or the sequence after the stem loop. The miR seed and the miR binding site may be for the same and/or different miR sequences.

In one embodiment, the incorporation of a miR sequence and/or a TEE sequence changes the shape of the stem loop region which may increase and/or decrease translation. (see e.g, Kedde et al. A Pumilio-induced RNA structure switch in p27-3'-UTR controls miR-221 and miR-22 accessibility. Nature Cell Biology. 2010, incorporated herein by reference in its entirety).

In one embodiment, the incorporation of a miR sequence and/or a TEE sequence changes the shape of the stem loop region which may increase and/or decrease translation. (see e.g, Kedde et al. A Pumilio-induced RNA structure switch in p27-3'-UTR controls miR-221 and miR-22 accessibility. Nature Cell Biology. 2010, incorporated herein by reference in its entirety).

In one embodiment, the 5'-UTR may comprise at least one microRNA sequence. The microRNA sequence may be, but is not limited to, a 19 or 22 nucleotide sequence and/or a microRNA sequence without the seed.

In one embodiment the microRNA sequence in the 5'-UTR may be used to stabilize the nucleic acid and/or mRNA described herein.

In another embodiment, a microRNA sequence in the 5'-UTR may be used to decrease the accessibility of the site of translation initiation such as, but not limited to a start codon. Matsuda et al (PLoS One. 2010 11(5):e15057; incorporated herein by reference in its entirety) used antisense locked nucleic acid (LNA) oligonucleotides and exon-junction complexes (EJCs) around a start codon (−4 to +37 where the A of the AUG codons is +1) in order to decrease the accessibility to the first start codon (AUG). Matsuda showed that altering the sequence around the start codon with an LNA or EJC the efficiency, length and structural stability of the nucleic acid or mRNA is affected. The nucleic acids or mRNA of the present invention may comprise a microRNA sequence, instead of the LNA or EJC sequence described by Matsuda et al, near the site of translation initiation in order to decrease the accessibility to the site of translation initiation. The site of translation initiation may be prior to, after or within the microRNA sequence. As a non-limiting example, the site of translation initiation may be located within a microRNA sequence such as a seed sequence or binding site. As another non-limiting example, the site of translation initiation may be located within a miR-122 sequence such as the seed sequence or the mir-122 binding site.

In one embodiment, the nucleic acids or mRNA of the present invention may include at least one microRNA in order to dampen the antigen presentation by antigen presenting cells. The microRNA may be the complete microRNA sequence, the microRNA seed sequence, the microRNA sequence without the seed or a combination thereof. As a non-limiting example, the microRNA incorporated into the nucleic acids or mRNA of the present invention may be specific to the hematopoietic system. As another non-limiting example, the microRNA incorporated into the nucleic acids or mRNA of the present invention to dampen antigen presentation is miR-142-3p.

In one embodiment, the nucleic acids or mRNA of the present invention may include at least one microRNA in order to dampen expression of the encoded polypeptide in a cell of interest. As a non-limiting example, the nucleic acids or mRNA of the present invention may include at least one miR-122 binding site in order to dampen expression of an encoded polypeptide of interest in the liver. As another non-limiting example, the nucleic acids or mRNA of the present invention may include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In one embodiment, the nucleic acids or mRNA of the present invention may comprise at least one microRNA binding site in the 3'-UTR in order to selectively degrade mRNA therapeutics in the immune cells to subdue unwanted immunogenic reactions caused by therapeutic delivery. As a non-limiting example, the microRNA binding site may be the alternative nucleic acids more unstable in antigen presenting cells. Non-limiting examples of these microRNA include mir-142-5p, mir-142-3p, mir-146a-5p and mir-146-3p.

In one embodiment, the nucleic acids or mRNA of the present invention comprises at least one microRNA sequence in a region of the nucleic acid or mRNA which may interact with a RNA binding protein.

RNA Motifs for RNA Binding Proteins (RBPs)

RNA binding proteins (RBPs) can regulate numerous aspects of co- and post-transcription gene expression such as, but not limited to, RNA splicing, localization, translation, turnover, polyadenylation, capping, alteration, export and localization. RNA-binding domains (RBDs), such as, but not limited to, RNA recognition motif (RR) and hnRNP K-homology (KH) domains, typically regulate the sequence association between RBPs and their RNA targets (Ray et al. Nature 2013. 499:172-177; incorporated herein by reference in its entirety). In one embodiment, the canonical RBDs can bind short RNA sequences. In another embodiment, the canonical RBDs can recognize structure RNAs.

In one embodiment, to increase the stability of the mRNA of interest, an mRNA encoding HuR can be co-transfected or co-injected along with the mRNA of interest into the cells or into the tissue. These proteins can also be tethered to the mRNA of interest in vitro and then administered to the cells together. Poly A tail binding protein, PABP interacts with eukaryotic translation initiation factor eIF4G to stimulate translational initiation. Co-administration of mRNAs encoding these RBPs along with the mRNA drug and/or tethering these proteins to the mRNA drug in vitro and administering the protein-bound mRNA into the cells can increase the translational efficiency of the mRNA. The same concept can be extended to co-administration of mRNA along with mRNAs encoding various translation factors and facilitators as well as with the proteins themselves to influence RNA stability and/or translational efficiency.

In one embodiment, the nucleic acids and/or mRNA may comprise at least one RNA-binding motif such as, but not limited to a RNA-binding domain (RBD).

In one embodiment, the RBD may be any of the RBDs, fragments or variants thereof descried by Ray et al. (Nature 2013. 499:172-177; incorporated herein by reference in its entirety).

In one embodiment, the nucleic acids or mRNA of the present invention may comprise a sequence for at least one RNA-binding domain (RBDs). When the nucleic acids or mRNA of the present invention comprise more than one RBD, the RBDs do not need to be from the same species or even the same structural class.

In one embodiment, at least one flanking region (e.g., the 5'-UTR and/or the 3'-UTR) may comprise at least one RBD. In another embodiment, the first flanking region and the second flanking region may both comprise at least one RBD. The RBD may be the same or each of the RBDs may have at least 60% sequence identity to the other RBD. As a non-limiting example, at least on RBD may be located before, after and/or within the 3'-UTR of the nucleic acid or mRNA of the present invention. As another non-limiting example, at least one RBD may be located before or within the first 300 nucleosides of the 3'-UTR.

In another embodiment, the nucleic acids and/or mRNA of the present invention may comprise at least one RBD in the first region of linked nucleosides. The RBD may be located before, after or within a coding region (e.g., the ORF).

In yet another embodiment, the first region of linked nucleosides and/or at least one flanking region may comprise at least on RBD. As a non-limiting example, the first region of linked nucleosides may comprise a RBD related to splicing factors and at least one flanking region may comprise a RBD for stability and/or translation factors.

In one embodiment, the nucleic acids and/or mRNA of the present invention may comprise at least one RBD located in a coding and/or non-coding region of the nucleic acids and/or mRNA.

In one embodiment, at least one RBD may be incorporated into at least one flanking region to increase the stability of the nucleic acid and/or mRNA of the present invention.

In one embodiment, a microRNA sequence in a RNA binding protein motif may be used to decrease the accessibility of the site of translation initiation such as, but not limited to a start codon. The nucleic acids or mRNA of the present invention may comprise a microRNA sequence, instead of the LNA or EJC sequence described by Matsuda et al, near the site of translation initiation in order to decrease the accessibility to the site of translation initiation. The site of translation initiation may be prior to, after or within the microRNA sequence. As a non-limiting example, the site of translation initiation may be located within a microRNA sequence such as a seed sequence or binding site. As another non-limiting example, the site of translation initiation may be located within a miR-122 sequence such as the seed sequence or the mir-122 binding site.

In another embodiment, an antisense locked nucleic acid (LNA) oligonucleotides and exon-junction complexes (EJCs) may be used in the RNA binding protein motif. The LNA and EJCs may be used around a start codon (−4 to +37 where the A of the AUG codons is +1) in order to decrease the accessibility to the first start codon (AUG).

Codon Optimization

The polynucleotides of the invention, their regions or parts or subregions may be codon optimized. Codon optimization methods are known in the art and may be useful in efforts to achieve one or more of several goals. These goals include to match codon frequencies in target and host organisms to ensure proper folding, bias GC content to increase mRNA stability or reduce secondary structures, minimize tandem repeat codons or base runs that may impair gene construction or expression, customize transcriptional and translational control regions, insert or remove protein trafficking sequences, remove/add post translation modification sites in encoded protein (e.g., glycosylation sites), add, remove or shuffle protein domains, insert or delete restriction sites, modify ribosome binding sites and mRNA degradation sites, to adjust translational rates to allow the various domains of the protein to fold properly, or to reduce or eliminate problem secondary structures within the polynucleotide. Codon optimization tools, algorithms and services are known in the art, non-limiting examples include services from GeneArt (Life Technologies), DNA2.0 (Menlo Park Calif.) and/or proprietary methods. In one embodiment, the ORF sequence is optimized using optimization algorithms. Codon options for each amino acid are given in Table 9.

TABLE 9

Codon Options.

| Amino Acid | Single Letter Code | Codon Options |
|---|---|---|
| Isoleucine | I | AUU, AUC, AUA |
| Leucine | L | CUU, CUC, CUA, CUG, UUA, UUG |
| Valine | V | GUU, GUC, GUA, GUG |
| Phenylalanine | F | UUU, UUC |
| Methionine | M | AUG |
| Cysteine | C | UGU, UGC |
| Alanine | A | GCU, GCC, GCA, GCG |
| Glycine | G | GGU, GGC, GGA, GGG |
| Proline | P | CCU, CCC, CCA, CCG |
| Threonine | T | ACU, ACC, ACA, ACG |
| Serine | S | UCU, UCC, UCA, UCG, AGU, AGC |
| Tyrosine | Y | UAU, UAC |
| Tryptophan | W | UGG |
| Glutamine | Q | CAA, CAG |
| Asparagine | N | AAU, AAC |
| Histidine | H | CAU, CAC |
| Glutamic acid | E | GAA, GAG |
| Aspartic acid | D | GAU, GAC |
| Lysine | K | AAA, AAG |
| Arginine | R | CGU, CGC, CGA, CGG, AGA, AGG |
| Selenocysteine | Sec | UGA in mRNA in presence of Selenocystein insertion element (SECIS) |
| Stop codons | Stop | UAA, UAG, UGA |

"Codon optimized" refers to the modification of a starting nucleotide sequence by replacing at least one codon of the starting nucleotide sequence with another codon encoding the same amino acid (e.g., to increase in vivo expression). Table 10 contains the codon usage frequency for humans (Codon usage database: [[www.]]kazusa.or.jp/codon/cgi-bin/showcodon.cgi?species=9606&aa=1&style=N).

TABLE 10

Codon usage frequency table for humans.

| Codon | Amino Acid | % | Codon | Amino Acid | % | Codon | Amino Acid | % | Codon | Amino Acid | % |
|---|---|---|---|---|---|---|---|---|---|---|---|
| UUU | F (2) | 46 | UCU | S (3) | 19 | UAU | Y (2) | 44 | UGU | C (2) | 46 |
| UUC | F (1) | 54 | UCC | S (2) | 22 | UAC | Y (1) | 56 | UGC | C (1) | 54 |
| UUA | L (5) | 8 | UCA | S (4) | 15 | UAA | * | 30 | UGA | * | 47 |
| UUG | L (4) | 13 | UCG | S (6) | 5 | UAG | * | 24 | UGG | W (1) | 100 |
| CUU | L (3) | 13 | CCU | P (2) | 29 | CAU | H (2) | 42 | CGU | R (6) | 8 |
| CUC | L(2) | 20 | CCC | P (1) | 32 | CAC | H (1) | 58 | CGC | R (4) | 18 |
| CUA | L (6) | 7 | CCA | P (3) | 28 | CAA | Q (2) | 27 | CGA | R (5) | 11 |
| CUG | L (1) | 40 | CCG | P (4) | 11 | CAG | Q (1) | 73 | CGG | R (3) | 20 |
| AUU | I (2) | 36 | ACU | T (3) | 25 | AAU | N (2) | 47 | AGU | S (5) | 15 |
| AUC | I (1) | 47 | ACC | T (1) | 36 | AAC | N (1) | 53 | AGC | S (1) | 24 |
| AUA | I (3) | 17 | ACA | T (2) | 28 | AAA | K (2) | 43 | AGA | R (2) | 21 |
| AUG | M (1) | 100 | ACG | T (4) | 11 | AAG | K (1) | 57 | AGG | R (1) | 21 |
| GUU | V (3) | 18 | GCU | A (2) | 27 | GAU | D (2) | 46 | GGU | G (4) | 16 |
| GUC | V (2) | 24 | GCC | A (1) | 40 | GAC | D (1) | 54 | GGC | G (1) | 34 |
| GUA | V (4) | 12 | GCA | A (3) | 23 | GAA | E (2) | 42 | GGA | G (2) | 25 |
| GUG | V (1) | 46 | GCG | A (4) | 11 | GAG | E (1) | 58 | GGG | G (3) | 25 |

In Table 10, the number in parentheses after the one letter amino acid code indicates the frequency of that codon relative to other codons encoding the same amino acid, where "1" is the highest frequency and higher integers indicate less frequent codons.

A guanine maximized codon is a codon having the highest number of guanines possible for a specified amino acid. A cytosine maximized codon is a codon having the highest number of cytosines possible for a specified amino acid. A guanine/cytosine maximized codon refers to a codon having the highest number of guanines, cytosines, or combination of guanines and cytosines for a specified amino acid. When two or more codons have the same number of guanines, cytosines, or combination thereof for a specified amino acid, a low frequency maximized codon is a codon that is not the highest frequency codon.

In one embodiment, after a nucleotide sequence has been codon optimized it may be further evaluated for regions containing restriction sites. At least one nucleotide within the restriction site regions may be replaced with another nucleotide in order to remove the restriction site from the sequence, but the replacement of nucleotides does not alter the amino acid sequence which is encoded by the codon optimized nucleotide sequence.

Features, which may be considered beneficial in some embodiments of the present invention, may be encoded by regions of the polynucleotide and such regions may be upstream (5') or downstream (3') to a region which encodes a polypeptide. These regions may be incorporated into the polynucleotide before and/or after codon optimization of the protein encoding region or open reading frame (ORF). It is not required that a polynucleotide contain both a 5' and 3' flanking region. Examples of such features include, but are not limited to, untranslated regions (UTRs), Kozak sequences, an oligo(dT) sequence, and detectable tags and may include multiple cloning sites which may have XbaI recognition.

In some embodiments, a 5' UTR and/or a 3' UTR region may be provided as flanking regions. Multiple 5' or 3' UTRs may be included in the flanking regions and may be the same or of different sequences. Any portion of the flanking regions, including none, may be codon optimized and any may independently contain one or more different structural or chemical alterations, before and/or after codon optimization.

After optimization (if desired), the polynucleotides components are reconstituted and transformed into a vector such as, but not limited to, plasmids, viruses, cosmids, and artificial chromosomes. For example, the optimized polynucleotide may be reconstituted and transformed into chemically competent *E. coli*, yeast, *neurospora*, maize, *drosophila*, etc. where high copy plasmid-like or chromosome structures occur by methods described herein.

Uses of Alternative Nucleic Acids

Therapeutic Agents

The alternative nucleic acids described herein can be used as therapeutic agents. For example, an alternative nucleic acid described herein can be administered to an animal or subject, wherein the alternative nucleic acid is translated in vivo to produce a therapeutic peptide in the animal or subject. Accordingly, provided herein are mRNA, compositions (such as pharmaceutical compositions), methods, kits, and reagents for treatment or prevention of disease or conditions in humans and other mammals. The active therapeutic agents of the present disclosure include alternative nucleic acids, cells containing alternative nucleic acids or polypeptides translated from the alternative nucleic acids, polypeptides translated from alternative nucleic acids, cells contacted with cells containing alternative nucleic acids or polypeptides translated from the alternative nucleic acids, tissues containing cells containing alternative nucleic acids and organs containing tissues containing cells containing alternative nucleic acids.

Provided are methods of inducing translation of a synthetic or recombinant polynucleotide to produce a polypeptide in a cell population using the alternative nucleic acids described herein. Such translation can be in vivo, ex vivo, in culture, or in vitro. The cell population is contacted with an effective amount of a composition containing a nucleic acid that has at least one nucleoside alteration, and a translatable region encoding the polypeptide. The population is contacted under conditions such that the nucleic acid is localized into one or more cells of the cell population and the recombinant polypeptide is translated in the cell from the nucleic acid.

An effective amount of the composition is provided based, at least in part, on the target tissue, target cell type, means of administration, physical characteristics of the nucleic acid (e.g., size, and extent of alternative nucleosides), and other determinants. In general, an effective amount of the composition provides efficient protein production in the cell, preferably more efficient than a composition containing a corresponding unaltered nucleic acid. Increased efficiency may be demonstrated by increased cell transfection (i.e., the percentage of cells transfected with the nucleic acid), increased protein translation from the nucleic acid, decreased nucleic acid degradation (as demonstrated, e.g., by increased duration of protein translation from a modified nucleic acid), or reduced innate immune response of the host cell or improve therapeutic utility.

Aspects of the present disclosure are directed to methods of inducing in vivo translation of a recombinant polypeptide in a mammalian subject in need thereof. Therein, an effective amount of a composition containing a nucleic acid that has at least one nucleoside alteration and a translatable region encoding the polypeptide is administered to the subject using the delivery methods described herein. The nucleic acid is provided in an amount and under other conditions such that the nucleic acid is localized into a cell or cells of the subject and the recombinant polypeptide is translated in the cell from the nucleic acid. The cell in which the nucleic acid is localized, or the tissue in which the cell is present, may be targeted with one or more than one rounds of nucleic acid administration.

Other aspects of the present disclosure relate to transplantation of cells containing alternative nucleic acids to a mammalian subject. Administration of cells to mammalian subjects is known to those of ordinary skill in the art, such as local implantation (e.g., topical or subcutaneous administration), organ delivery or systemic injection (e.g., intravenous injection or inhalation), as is the formulation of cells in pharmaceutically acceptable carrier. Compositions containing alternative nucleic acids are formulated for administration intramuscularly, transarterially, intraperitoneally, intravenously, intranasally, subcutaneously, endoscopically, transdermally, or intrathecally. In some embodiments, the composition is formulated for extended release.

The subject to whom the therapeutic agent is administered suffers from or is at risk of developing a disease, disorder, or deleterious condition. Provided are methods of identifying, diagnosing, and classifying subjects on these bases, which may include clinical diagnosis, biomarker levels, genome-wide association studies (GWAS), and other methods known in the art.

In certain embodiments, the administered alternative nucleic acid directs production of one or more recombinant polypeptides that provide a functional activity which is substantially absent in the cell in which the recombinant polypeptide is translated. For example, the missing functional activity may be enzymatic, structural, or gene regulatory in nature.

In other embodiments, the administered alternative nucleic acid directs production of one or more recombinant polypeptides that replace a polypeptide (or multiple polypeptides) that is substantially absent in the cell in which the recombinant polypeptide is translated. Such absence may be due to genetic mutation of the encoding gene or regulatory pathway thereof. In other embodiments, the administered alternative nucleic acid directs production of one or more recombinant polypeptides to supplement the amount of polypeptide (or multiple polypeptides) that is present in the cell in which the recombinant polypeptide is translated. Alternatively, the recombinant polypeptide functions to antagonize the activity of an endogenous protein present in, on the surface of, or secreted from the cell. Usually, the activity of the endogenous protein is deleterious to the subject, for example, due to mutation of the endogenous protein resulting in altered activity or localization. Additionally, the recombinant polypeptide antagonizes, directly or indirectly, the activity of a biological moiety present in, on the surface of, or secreted from the cell. Examples of antagonized biological moieties include lipids (e.g., cholesterol), a lipoprotein (e.g., low density lipoprotein), a nucleic acid, a carbohydrate, or a small molecule toxin.

The recombinant proteins described herein are engineered for localization within the cell, potentially within a specific compartment such as the nucleus, or are engineered for secretion from the cell or translocation to the plasma membrane of the cell.

As described herein, a useful feature of the alternative nucleic acids of the present disclosure is the capacity to reduce, evade, avoid or eliminate the innate immune response of a cell to an exogenous nucleic acid. Provided are methods for performing the titration, reduction or elimination of the immune response in a cell or a population of cells.

In some embodiments, the cell is contacted with a first composition that contains a first dose of a first exogenous nucleic acid including a translatable region and at least one nucleoside alteration, and the level of the innate immune response of the cell to the first exogenous nucleic acid is determined. Subsequently, the cell is contacted with a second composition, which includes a second dose of the first exogenous nucleic acid, the second dose containing a lesser amount of the first exogenous nucleic acid as compared to the first dose. Alternatively, the cell is contacted with a first dose of a second exogenous nucleic acid. The second exogenous nucleic acid may contain one or more alternative nucleosides, which may be the same or different from the first exogenous nucleic acid or, alternatively, the second exogenous nucleic acid may not contain alternative nucleosides. The steps of contacting the cell with the first composition and/or the second composition may be repeated one or more times. Additionally, efficiency of protein production (e.g., protein translation) in the cell is optionally determined, and the cell may be re-transfected with the first and/or second composition repeatedly until a target protein production efficiency is achieved.

Therapeutics for Diseases and Conditions

Provided are methods for treating or preventing a symptom of diseases characterized by missing or aberrant protein activity, by replacing the missing protein activity or overcoming the aberrant protein activity. Because of the rapid initiation of protein production following introduction of alternative mRNAs, as compared to viral DNA vectors, the compounds of the present disclosure are particularly advantageous in treating acute diseases such as sepsis, stroke, and myocardial infarction. Moreover, the lack of transcriptional regulation of the alternative mRNAs of the present disclosure is advantageous in that accurate titration of protein production is achievable. Multiple diseases are characterized by missing (or substantially diminished such that proper protein function does not occur) protein activity. Such proteins may not be present, are present in very low quantities or are essentially non-functional. The present disclosure provides a method for treating such conditions or diseases in a subject by introducing nucleic acid or cell-based therapeutics containing the alternative nucleic acids provided herein, wherein the alternative nucleic acids encode for a protein that replaces the protein activity missing from the target cells of the subject.

Diseases characterized by dysfunctional or aberrant protein activity include, but not limited to, cancer and proliferative diseases, genetic diseases (e.g., cystic fibrosis), autoimmune diseases, diabetes, neurodegenerative diseases, cardiovascular diseases, and metabolic diseases. The present disclosure provides a method for treating such conditions or diseases in a subject by introducing nucleic acid or cell-based therapeutics containing the alternative nucleic acids provided herein, wherein the alternative nucleic acids encode for a protein that antagonizes or otherwise overcomes the aberrant protein activity present in the cell of the subject.

Specific examples of a dysfunctional protein are the missense or nonsense mutation variants of the cystic fibrosis transmembrane conductance regulator (CFTR) gene, which produce a dysfunctional or nonfunctional, respectively, protein variant of CFTR protein, which causes cystic fibrosis.

Thus, provided are methods of treating cystic fibrosis in a mammalian subject by contacting a cell of the subject with an alternative nucleic acid having a translatable region that encodes a functional CFTR polypeptide, under conditions such that an effective amount of the CTFR polypeptide is present in the cell. Preferred target cells are epithelial cells, such as the lung, and methods of administration are determined in view of the target tissue; i.e., for lung delivery, the RNA molecules are formulated for administration by inhalation. Therefore, in certain embodiments, the polypeptide of interest encoded by the mRNA of the invention is the CTFR polypeptide and the mRNA or pharmaceutical composition of the invention is for use in treating cystic fibrosis.

In another embodiment, the present disclosure provides a method for treating hyperlipidemia in a subject, by introducing into a cell population of the subject with an alternative mRNA molecule encoding Sortilin, a protein recently characterized by genomic studies, thereby ameliorating the hyperlipidemia in a subject. The SORT1 gene encodes a trans-Golgi network (TGN) transmembrane protein called Sortilin. Genetic studies have shown that one of five individuals has a single nucleotide polymorphism, rs12740374, in the 1p13 locus of the SORT1 gene that predisposes them to having low levels of low-density lipoprotein (LDL) and very-low-density lipoprotein (VLDL). Each copy of the minor allele, present in about 30% of people, alters LDL cholesterol by 8 mg/dL, while two copies of the minor allele, present in about 5% of the population, lowers LDL cholesterol 16 mg/dL. Carriers of the minor allele have also been shown to have a 40% decreased risk of myocardial infarction. Functional in vivo studies in mice describes that overexpression of SORT1 in mouse liver tissue led to significantly lower LDL-cholesterol levels, as much as 80% lower, and that silencing SORT1 increased LDL cholesterol approximately 200% (Musunuru K et al. From noncoding variant to phenotype via SORT1 at the 1p13 cholesterol locus. Nature 2010; 466: 714-721). Therefore, in certain embodiments, the polypeptide of interest encoded by the mRNA of the invention is Sortilin and the mRNA or pharmaceutical composition of the invention is for use in treating hyperlipidemia.

In certain embodiments, the polypeptide of interest encoded by the mRNA of the invention is granulocyte colony-stimulating factor (GCSF), and the mRNA or pharmaceutical composition of the invention is for use in treating a neurological disease such as cerebral ischemia, or treating neutropenia, or for use in increasing the number of hematopoietic stem cells in the blood (e.g. before collection by leukapheresis for use in hematopoietic stem cell transplantation).

In certain embodiments, the polypeptide of interest encoded by the mRNA of the invention is erythropoietin (EPO), and the mRNA or pharmaceutical composition of the invention is for use in treating anemia, inflammatory bowel disease (such as Crohn's disease and/or ulcer colitis) or myelodysplasia.

Methods of Cellular Nucleic Acid Delivery

Methods of the present disclosure enhance nucleic acid delivery into a cell population, in vivo, ex vivo, or in culture. For example, a cell culture containing a plurality of host cells (e.g., eukaryotic cells such as yeast or mammalian cells) is contacted with a composition that contains an enhanced nucleic acid having at least one nucleoside alteration and, optionally, a translatable region. The composition also generally contains a transfection reagent or other compound that increases the efficiency of enhanced nucleic acid uptake into the host cells. The enhanced nucleic acid exhibits enhanced retention in the cell population, relative to a corresponding unaltered nucleic acid. The retention of the enhanced nucleic acid is greater than the retention of the unaltered nucleic acid. In some embodiments, it is at least about 50%, 75%, 90%, 95%, 100%, 150%, 200% or more than 200% greater than the retention of the unaltered nucleic acid. Such retention advantage may be achieved by one round of transfection with the enhanced nucleic acid, or may be obtained following repeated rounds of transfection.

In some embodiments, the enhanced nucleic acid is delivered to a target cell population with one or more additional nucleic acids. Such delivery may be at the same time, or the enhanced nucleic acid is delivered prior to delivery of the one or more additional nucleic acids. The additional one or more nucleic acids may be alternative nucleic acids or unaltered nucleic acids. It is understood that the initial presence of the enhanced nucleic acids does not substantially induce an innate immune response of the cell population and, moreover, that the innate immune response will not be activated by the later presence of the unaltered nucleic acids. In this regard, the enhanced nucleic acid may not itself contain a translatable region, if the protein desired to be present in the target cell population is translated from the unaltered nucleic acids.

Targeting Moieties

In embodiments of the present disclosure, alternative nucleic acids are provided to express a protein-binding partner or a receptor on the surface of the cell, which functions to target the cell to a specific tissue space or to interact with a specific moiety, either in vivo or in vitro. Suitable protein-binding partners include antibodies and functional fragments thereof, scaffold proteins, or peptides. Additionally, alternative nucleic acids can be employed to direct the synthesis and extracellular localization of lipids, carbohydrates, or other biological moieties.

Permanent Gene Expression Silencing

A method for epigenetically silencing gene expression in a mammalian subject, comprising a nucleic acid where the translatable region encodes a polypeptide or polypeptides capable of directing sequence-specific histone H3 methylation to initiate heterochromatin formation and reduce gene transcription around specific genes for the purpose of silencing the gene. For example, a gain-of-function mutation in the Janus Kinase 2 gene is responsible for the family of Myeloproliferative Diseases.

Pharmaceutical Compositions

Pharmaceutical compositions may optionally comprise one or more additional therapeutically active substances. In accordance with some embodiments, a method of administering pharmaceutical compositions comprising an alternative nucleic acid encoding one or more proteins to be delivered to a subject in need thereof is provided. In some embodiments, compositions are administered to humans Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this present disclosure.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween®20], polyoxyethylene sorbitan [Tween®60], polyoxyethylene sorbitan monooleate [Tween®80], sorbitan monopalmitate [Span®40], sorbitan monostearate [Span®60], sorbitan tristearate [Span®65], glyceryl monooleate, sorbitan monooleate [Span® 80]), polyoxyethylene esters (e.g. polyoxyethylene monostearate [Myrj®45], polyoxyethylene hydrogenated castor oil, polyethoxylated castor oil, polyoxymethylene stearate, and Solutol®), sucrose fatty acid esters, polyethylene glycol fatty acid esters (e.g. Cremophor®), polyoxyethylene ethers, (e.g. polyoxyethylene lauryl ether [Brij®30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic®F 68, Poloxamer®188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, and mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus®, Phenonip®, methylparaben, Germall®115, Germaben®II, Neolone™, Kathon™ and/or Euxyl®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as Cremophor®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato or tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required. Additionally, the present disclosure contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for pulmonary administration via the buccal cavity. Such a formulation may comprise dry particles which comprise the active ingredient and which have a diameter in the range from about 0.5 nm to about 7 nm or from about 1 nm to about 6 nm. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and active ingredient may constitute 0.1% to 20% (w/w) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner in which snuff is taken, i.e., by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

A pharmaceutical composition may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of any additional ingredients described herein. Other opthalmically-administrable formulations which are useful include those which comprise the active ingredient in microcrystalline form and/or in a liposomal preparation. Ear drops and/or eye drops are contemplated as being within the scope of this present disclosure.

General considerations in the formulation and/or manufacture of pharmaceutical agents may be found, for example, in Remington's *The Science and Practice of Pharmacy, 21$^{st}$ Edition*, A. R. Gennaro (Lippincott, Williams & Wilkins, Baltimore, Md., 2006; incorporated herein by reference).

Administration

The present disclosure provides methods comprising administering mRNA in accordance with the present disclosure to a subject in need thereof. mRNA, or pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like. Compositions in accordance with the present disclosure are typically formulated in dosage unit form for ease of administration and uniformity of dosage. It will be understood, however, that the total daily usage of the compositions of the present disclosure will be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

mRNAs to be delivered and/or pharmaceutical, prophylactic, diagnostic, or imaging compositions thereof may be administered to animals, such as mammals (e.g., humans, domesticated animals, cats, dogs, mice, rats, etc.). In some embodiments, pharmaceutical, prophylactic, diagnostic, or imaging compositions thereof are administered to humans.

mRNAs to be delivered and/or pharmaceutical, prophylactic, diagnostic, or imaging compositions thereof in accordance with the present disclosure may be administered by any route. In some embodiments, mRNAs and/or pharmaceutical, prophylactic, diagnostic, or imaging compositions thereof, are administered by one or more of a variety of routes, including oral, intravenous, intramuscular, intraarterial, intramedullary, intrathecal, subcutaneous, intraventricular, transdermal, interdermal, rectal, intravaginal, intraperitoneal, topical (e.g., by powders, ointments, creams, gels, lotions, and/or drops), mucosal, nasal, buccal, enteral, vitreal, intratumoral, sublingual; by intratracheal instillation, bronchial instillation, and/or inhalation; as an oral spray, nasal spray, and/or aerosol, and/or through a portal vein catheter. In some embodiments, mRNAs, and/or pharmaceutical, prophylactic, diagnostic, or imaging compositions thereof, are administered by systemic intravenous injection. In specific embodiments, mRNAs and/or pharmaceutical, prophylactic, diagnostic, or imaging compositions thereof may be administered intravenously and/or orally. In specific embodiments, mRNAs, and/or pharmaceutical, prophylactic, diagnostic, or imaging compositions thereof, may be administered in a way which allows the mRNA to cross the blood-brain barrier, vascular barrier, or other epithelial barrier.

However, the present disclosure encompasses the delivery of mRNAs, and/or pharmaceutical, prophylactic, diagnostic, or imaging compositions thereof, by any appropriate route taking into consideration likely advances in the sciences of drug delivery.

In general the most appropriate route of administration will depend upon a variety of factors including the nature of the mRNA associated with at least one agent to be delivered (e.g., its stability in the environment of the gastrointestinal tract, bloodstream, etc.), the condition of the patient (e.g., whether the patient is able to tolerate particular routes of administration), etc. The present disclosure encompasses the delivery of the pharmaceutical, prophylactic, diagnostic, or imaging compositions by any appropriate route taking into consideration likely advances in the sciences of drug delivery.

In certain embodiments, compositions in accordance with the present disclosure may be administered at dosage levels sufficient to deliver from about 0.0001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

mRNAs may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that improve their bioavailability, reduce and/or modify their metabolism, inhibit their excretion, and/or modify their distribution within the body.

It will further be appreciated that therapeutically, prophylactically, diagnostically, or imaging active agents utilized in combination may be administered together in a single composition or administered separately in different compositions. In general, it is expected that agents utilized in combination with be utilized at levels that do not exceed the levels at which they are utilized individually. In some embodiments, the levels utilized in combination will be lower than those utilized individually.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer in accordance with the present disclosure may be administered concurrently with a chemotherapeutic agent), or they may achieve different effects (e.g., control of any adverse effects).

Kits

The present disclosure provides a variety of kits for conveniently and/or effectively carrying out methods of the present disclosure. Typically kits will comprise sufficient amounts and/or numbers of components to allow a user to perform multiple treatments of a subject(s) and/or to perform multiple experiments.

In one aspect, the disclosure provides kits for protein production, comprising a first isolated nucleic acid comprising a translatable region and a nucleic acid alteration, wherein the nucleic acid is capable of evading or avoiding induction of an innate immune response of a cell into which the first isolated nucleic acid is introduced, and packaging and instructions.

In one aspect, the disclosure provides kits for protein production, comprising: a first isolated alternative nucleic acid comprising a translatable region, provided in an amount effective to produce a desired amount of a protein encoded by the translatable region when introduced into a target cell; a second nucleic acid comprising an inhibitory nucleic acid, provided in an amount effective to substantially inhibit the innate immune response of the cell; and packaging and instructions.

In one aspect, the disclosure provides kits for protein production, comprising a first isolated nucleic acid comprising a translatable region and a nucleoside alteration, wherein the nucleic acid exhibits reduced degradation by a cellular nuclease, and packaging and instructions.

In one aspect, the disclosure provides kits for protein production, comprising a first isolated nucleic acid comprising a translatable region and at least two different nucleoside alterations, wherein the nucleic acid exhibits reduced degradation by a cellular nuclease, and packaging and instructions.

In one aspect, the disclosure provides kits for protein production, comprising a first isolated nucleic acid comprising a translatable region and at least one nucleoside alteration, wherein the nucleic acid exhibits reduced degradation by a cellular nuclease; a second nucleic acid comprising an inhibitory nucleic acid; and packaging and instructions.

In another aspect, the disclosure provides compositions for protein production, comprising a first isolated nucleic acid comprising a translatable region and a nucleoside alteration, wherein the nucleic acid exhibits reduced degradation by a cellular nuclease, and a mammalian cell suitable for translation of the translatable region of the first nucleic acid.

Definitions

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

Aberrant transcription product: As used herein, the term "aberrant transcription product" refers to any contaminating transcription product or impurity that differs from the intended high fidelity RNA transcript that is encoded by a given DNA template. Such aberrant transcription products can include short RNAs as a result of abortive transcription initiation events (Milligan et al., 1987, Nucleic Acids Res 15:8783-8798) and double stranded (ds)RNAs generated by RNA dependent RNA polymerase activity (Arnaud-Barbe et al, 1998, Nucleic Acids Res 26:3550-3554), RNA-primed transcription from RNA templates (Nacheva and Berzal-Herranz, 2003, Eur J Biochem 270: 1458-1465), and self-complementary 3' extension (Triana-Alonso et al., 1995, J Biol Chem 270:6298-6307), i.e. a "3'-transcript extension region".

About: As used herein, the term "about" when used in the context of the amount of an alternative nucleobase or nucleoside in a polynucleic acid means +/−10% of the recited value. For example, a polynucleotide containing about 25% of an alternative uracil includes between 22.5-27.5% of the alternative uracil.

Administered in combination: As used herein, the term "administered in combination" or "combined administration" means that two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Altered: As used herein "altered" refers to a changed state or structure of a molecule of the invention. Molecules may be altered in many ways including chemically, structurally, and functionally. In one embodiment, the mRNA molecules of the present invention are altered by the introduction of non-natural nucleosides and/or nucleotides, e.g., as it relates to the natural ribonucleotides A, U, G, and C. Noncanonical nucleotides such as the cap structures are not considered "altered" although they differ from the chemical structure of the A, C, G, U ribonucleotides.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Antigens of interest or desired antigens: As used herein, the terms "antigens of interest" or "desired antigens" include those proteins and other biomolecules provided herein that are immunospecifically bound by the antibodies and fragments, mutants, variants, and alterations thereof described herein. Examples of antigens of interest include, but are not limited to, insulin, insulin-like growth factor, hGH, tPA, cytokines, such as interleukins (IL), e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosis factor (TNF), such as TNF alpha and TNF beta, TNF gamma, TRAIL; G-CSF, GM-CSF, M-CSF, MCP-1 and VEGF.

Approximately: As used herein, the term "approximately" or "about," as applied to one or more values of interest other than the amount of an alternative nucleobase or nucleoside in a polynucleic acid, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a polynucleotide of the present invention may be considered biologically active if even a portion of the polynucleotide is biologically active or mimics an activity considered biologically relevant.

Compound: As used herein, the term "compound," is meant to include all stereoisomers, geometric isomers, tautomers, and isotopes of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an oligonucleotide or polypeptide or may apply to a portion, region or feature thereof.

Cyclic or Cyclized: As used herein, the term "cyclic" refers to the presence of a continuous loop. Cyclic molecules need not be circular, only joined to form an unbroken chain of subunits. Cyclic molecules such as the mRNA of the present invention may be single units or multimers or comprise one or more components of a complex or higher order structure.

Cytostatic: As used herein, "cytostatic" refers to inhibiting, reducing, suppressing the growth, division, or multiplication of a cell (e.g., a mammalian cell (e.g., a human cell)), bacterium, virus, fungus, protozoan, parasite, prion, or a combination thereof.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivery: As used herein, "delivery" refers to the act or manner of delivering a compound, substance, entity, moiety, cargo or payload.

Delivery Agent: As used herein, "delivery agent" refers to any substance which facilitates, at least in part, the in vivo delivery of a polynucleotide to targeted cells.

Destabilized: As used herein, the term "destable," "destabilize," or "destabilizing region" means a region or molecule that is less stable than a starting, wild-type or native form of the same region or molecule.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the peptides or proteins disclosed herein. They may be within the amino acids, the peptides, or proteins, or located at the N- or C-termini.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Encoded protein cleavage signal: As used herein, "encoded protein cleavage signal" refers to the nucleotide sequence which encodes a protein cleavage signal.

Engineered: As used herein, embodiments of the invention are "engineered" when they are designed to have a feature or property, whether structural or chemical, that varies from a starting point, wild-type or native molecule.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Feature: As used herein, a "feature" refers to a characteristic, a property, or a distinctive element.

Formulation: As used herein, a "formulation" includes at least a polynucleotide and a delivery agent.

Fragment: A "fragment," as used herein, refers to a portion. For example, fragments of proteins may comprise polypeptides obtained by digesting full-length protein isolated from cultured cells.

Functional: As used herein, a "functional" biological molecule is a biological molecule in a form in which it exhibits a property and/or activity by which it is characterized.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the invention, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the invention, two protein sequences are considered to be homologous if the proteins are at least about 50%, 60%, 70%, 80%, or 90% identical for at least one stretch of at least about 20 amino acids.

Identity: As used herein, the term "identity" refers to the overall relatedness between polymeric molecules, e.g., between oligonucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research*, 12(1), 387 (1984)), BLASTP, BLASTN, and FASTAn altschul, S. F. et al., *J. Molec. Biol.*, 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vitro synthesis: As used herein, the term "in vitro synthesis" refers to an extracellular method of synthesis of mRNA.

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Linker: As used herein, a linker refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to an alternative nucleoside or nucleotide on the nucleobase or sugar moiety at a first end, and to a payload, e.g., a detectable or therapeutic agent, at a second end. The linker may be of sufficient length as to not interfere with incorporation into a nucleic acid sequence. The linker can be used for any useful purpose, such as to form multimers (e.g., through linkage of two or more polynucleotides) or conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers, Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Maximized codons: As used herein the term "maximized codon" refers to a codon with the highest number of a nucleotide. For example, a "guanine maximized codon" is the codon for a particular amino acid that has the highest number of guanines.

Naturally occurring: As used herein, "naturally occurring" means existing in nature without artificial aid.

Non-human vertebrate: As used herein, a "non human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Paratope: As used herein, a "paratope" refers to the antigen-binding site of an antibody.

Patient: As used herein, "patient" refers to a subject who may seek or be in need of treatment, requires treatment, is receiving treatment, will receive treatment, or a subject who is under care by a trained professional for a particular disease or condition.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is altered by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's *The Science and Practice of Pharmacy*, 21$^{st}$ Edition, A. R. Gennaro (Lippincott, Williams & Wilkins, Baltimore, Md., 2006); *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-rdimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Physicochemical: As used herein, "physicochemical" means of or relating to a physical and/or chemical property.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Prodrugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Purified: As used herein, "purify," "purified," "purification" means to make substantially pure or clear from unwanted components, material defilement, admixture or imperfection.

Sample: As used herein, the term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Signal Sequences: As used herein, the phrase "signal sequences" refers to a sequence which can direct the transport or localization of a protein.

Significant or Significantly: As used herein, the terms "significant" or "significantly" are used synonymously with the term "substantially."

Single unit dose: As used herein, a "single unit dose" is a dose of any therapeutic administered in one dose/at one time/single route/single point of contact, i.e., single administration event.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Split dose: As used herein, a "split dose" is the division of single unit dose or total daily dose into two or more doses.

Stable: As used herein "stable" refers to a compound that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term means within 2 seconds.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Synthetic: The term "synthetic" means produced, prepared, and/or manufactured by the hand of man. Synthesis of polynucleotides or polypeptides or other molecules of the present invention may be chemical or enzymatic.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Theoretical Minimum: The term "theoretical minimum" refers to a nucleotide sequence with all of the codons in the open reading frame replaced to minimize the number of uracils in the sequence.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr period. It may be administered as a single unit dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unaltered: As used herein, "unaltered" refers to any substance, compound or molecule prior to being changed in any way. Unaltered may, but does not always, refer to the wild-type or native form of a biomolecule. Molecules may undergo a series of alterations whereby each alternative molecule may serve as the "unaltered" starting molecule for a subsequent alteration.

Uracil Content: As used herein, "uracil content" refers to the number and/or distribution of uracils in a particular sequence, e.g., an open reading frame.

Wild-type Sequence: As used herein, a "wild-type sequence" is the sequence of the naturally occurring mRNA that encodes the polypeptide of interest.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

EXAMPLES

The present disclosure is further described in the following examples, which do not limit the scope of the disclosure described in the claims.

Example 1: PCR for cDNA Production

PCR procedures for the preparation of cDNA are performed using 2×KAPA HIFI™ HotStart ReadyMix by Kapa Biosystems (Woburn, Mass.). This system includes 2×KAPA ReadyMix 12.5 µl; Forward Primer (10 uM) 0.75 µl; Reverse Primer (10 uM) 0.75 µl; Template cDNA 100 ng; and dH$_2$O diluted to 25.0 µl. The reaction conditions are at 95° C. for 5 min. and 25 cycles of 98° C. for 20 sec, then 58° C. for 15 sec, then 72° C. for 45 sec, then 72° C. for 5 min. then 4° C. to termination.

The reverse primer of the instant invention incorporates a poly-T$_{120}$ for a poly-A$_{120}$ in the mRNA. Other reverse primers with longer or shorter poly-T tracts can be used to adjust the length of the poly-A tail in the mRNA.

The reaction is cleaned up using Invitrogen's PURELINK™ PCR Micro Kit (Carlsbad, Calif.) per manufacturer's instructions (up to 5 µg). Larger reactions will require a cleanup using a product with a larger capacity. Following the cleanup, the cDNA is quantified using the NanoDrop and analyzed by agarose gel electrophoresis to confirm the cDNA is the expected size. The cDNA is then submitted for sequencing analysis before proceeding to the in vitro transcription reaction.

Example 2. In Vitro Transcription (IVT)

A. Materials and Methods

Alternative mRNAs according to the invention are made using standard laboratory methods and materials for in vitro transcription with the exception that the nucleotide mix contains alternative nucleotides. The open reading frame (ORF) of the gene of interest may be flanked by a 5' untranslated region (UTR) containing a strong Kozak translational initiation signal and an alpha-globin 3' UTR terminating with an oligo(dT) sequence for templated addition of a polyA tail for mRNAs not incorporating adenosine analogs. Adenosine-containing mRNAs are synthesized without an oligo (dT) sequence to allow for post-transcription poly (A) polymerase poly-(A) tailing.

The ORF may also include various upstream or downstream additions (such as, but not limited to, β-globin, tags, etc.) may be ordered from an optimization service such as, but limited to, DNA2.0 (Menlo Park, Calif.) and may contain multiple cloning sites which may have XbaI recognition. Upon receipt of the construct, it may be reconstituted and transformed into chemically competent E. coli.

For the present invention, NEB DH5-alpha Competent E. coli may be used. Transformations are performed according to NEB instructions using 100 ng of plasmid. The protocol is as follows:

Thaw a tube of NEB 5-alpha Competent E. coli cells on ice for 10 minutes.

Add 1-5 µl containing 1 pg-100 ng of plasmid DNA to the cell mixture. Carefully flick the tube 4-5 times to mix cells and DNA. Do not vortex.

Place the mixture on ice for 30 minutes. Do not mix.

Heat shock at 42° C. for exactly 30 seconds. Do not mix. Place on ice for 5 minutes. Do not mix.

Pipette 950 µl of room temperature SOC into the mixture. Place at 37° C. for 60 minutes. Shake vigorously (250 rpm) or rotate.

Warm selection plates to 37° C.

Mix the cells thoroughly by flicking the tube and inverting.

Spread 50-100 µl of each dilution onto a selection plate and incubate overnight at 37° C. Alternatively, incubate at 30° C. for 24-36 hours or 25° C. for 48 hours.

A single colony is then used to inoculate 5 ml of LB growth media using the appropriate antibiotic and then allowed to grow (250 RPM, 37° C.) for 5 hours. This is then used to inoculate a 200 ml culture medium and allowed to grow overnight under the same conditions.

To isolate the plasmid (up to 850 µg), a maxi prep is performed using the Invitrogen PURELINK™ HiPure Maxiprep Kit (Carlsbad, Calif.), following the manufacturer's instructions.

In order to generate cDNA for In Vitro Transcription (IVT), the plasmid is first linearized using a restriction enzyme such as XbaI. A typical restriction digest with XbaI will comprise the following: Plasmid 1.0 µg; 10× Buffer 1.0 µl; XbaI 1.5 µl; dH$_2$O up to 10 µl; incubated at 37° C. for 1 hr. If performing at lab scale (<5 µg), the reaction is cleaned up using Invitrogen's PURELINK™ PCR Micro Kit (Carlsbad, Calif.) per manufacturer's instructions. Larger scale purifications may need to be done with a product that has a larger load capacity such as Invitrogen's standard PURELINK™ PCR Kit (Carlsbad, Calif.). Following the cleanup, the linearized vector is quantified using the NanoDrop and analyzed to confirm linearization using agarose gel electrophoresis.

IVT Reaction

The in vitro transcription reaction generates mRNA containing alternative nucleotides or alternative RNA. The input nucleotide triphosphate (NTP) mix is made in-house using natural and unnatural NTPs.

A typical in vitro transcription reaction includes the following:

| | |
|---|---|
| Template cDNA | 1.0 µg |
| 10x transcription buffer (400 mM Tris-HCl pH 8.0, 190 mM MgCl$_2$, 50 mM DTT, 10 mM Spermidine) | 2.0 µl |
| Custom NTPs (25 mM each) | 7.2 µl |
| RNase Inhibitor | 20 U |
| T7 RNA polymerase | 3000 U |
| dH$_2$O | up to 20.0 µl |
| Incubation at 37° C for 3 hr-5 hrs. | |

The crude IVT mix may be stored at 4° C. overnight for cleanup the next day. 1 U of RNase-free DNase is then used to digest the original template. After 15 minutes of incubation at 37° C., the mRNA is purified using Ambion's MEGACLEAR™ Kit (Austin, Tex.) following the manufacturer's instructions. This kit can purify up to 500 µg of RNA. Following the cleanup, the RNA is quantified using the NanoDrop and analyzed by agarose gel electrophoresis to confirm the RNA is the proper size and that no degradation of the RNA has occurred.

The T7 RNA polymerase may be selected from, T7 RNA polymerase, T3 RNA polymerase and mutant polymerases such as, but not limited to, the novel polymerases able to incorporate alternative NTPs as well as those polymerases described by Liu (Esvelt et al. (Nature (2011) 472(7344): 499-503 and U.S. Publication No. 20110177495) which recognize alternate promoters, Ellington (Chelliserrykattil and Ellington, Nature Biotechnology (2004) 22(9):1155-1160) describing a T7 RNA polymerase variant to transcribe 2'-O-methyl RNA and Sousa (Padilla and Sousa, Nucleic Acids Research (2002) 30(24): e128) describing a T7 RNA polymerase double mutant; herein incorporated by reference in their entireties.

B. Agarose Gel Electrophoresis of Alternative mRNA

Individual alternative mRNAs (200-400 ng in a 20 µl volume) are loaded into a well on a non-denaturing 1.2% Agarose E-Gel (Invitrogen, Carlsbad, Calif.) and run for 12-15 minutes according to the manufacturer protocol.

C. Agarose Gel Electrophoresis of RT-PCR Products

Individual reverse transcribed-PCR products (200-400 ng) are loaded into a well of a non-denaturing 1.2% Agarose E-Gel (Invitrogen, Carlsbad, Calif.) and run for 12-15 minutes according to the manufacturer protocol.

D. Nanodrop Alternative mRNA Quantification and UV Spectral Data

Alternative mRNAs in TE buffer (1 µl) are used for Nanodrop UV absorbance readings to quantitate the yield of each alternative mRNA from an in vitro transcription reaction (UV absorbance traces are not shown).

Example 3. Enzymatic Capping of mRNA

Capping of the mRNA is performed as follows where the mixture includes: IVT RNA 60 µg-180 µg and dH$_2$O up to 72 µl. The mixture is incubated at 65° C. for 5 minutes to denature RNA, and then is transferred immediately to ice.

The protocol then involves the mixing of 10× Capping Buffer (0.5 M Tris-HCl (pH 8.0), 60 mM KCl, 12.5 mM MgCl$_2$) (10.0 µl); 20 mM GTP (5.0 µl); 20 mM S-Adenosyl Methionine (2.5 µl); RNase Inhibitor (100 U); 2'-O-Methyltransferase (400 U); Vaccinia capping enzyme (Guanylyl transferase) (40 U); dH$_2$O (Up to 28 µl); and incubation at 37° C. for 30 minutes for 60 µg RNA or up to 2 hours for 180 µg of RNA.

The mRNA is then purified using Ambion's MEGACLEAR™ Kit (Austin, Tex.) following the manufacturer's instructions. Following the cleanup, the RNA is quantified using the NANODROP™ (ThermoFisher, Waltham, Mass.) and analyzed by agarose gel electrophoresis to confirm the RNA is the proper size and that no degradation of the RNA has occurred. The RNA product may also be sequenced by running a reverse-transcription-PCR to generate the cDNA for sequencing.

Example 4. 5'-Guanosine Capping

A. Materials and Methods

The cloning, gene synthesis and vector sequencing may be performed by DNA2.0 Inc. (Menlo Park, Calif.). The ORF is restriction digested using XbaI and used for cDNA synthesis using tailed- or tail-less-PCR. The tailed-PCR cDNA product is used as the template for the alternative mRNA synthesis reaction using 25 mM each alternative nucleotide mix (all alternative nucleotides may be custom synthesized or purchased from TriLink Biotech, San Diego, Calif. except pyrrolo-C triphosphate which may be purchased from Glen Research, Sterling Va.; unmodifed nucleotides are purchased from Epicenter Biotechnologies, Madison, Wis.) and CellScript MEGASCRIPT™ (Epicenter Biotechnologies, Madison, Wis.) complete mRNA synthesis kit.

The in vitro transcription reaction is run for 4 hours at 37° C. Alternative mRNAs incorporating adenosine analogs are poly (A) tailed using yeast Poly (A) Polymerase (Affymetrix, Santa Clara, Calif.). The PCR reaction uses HiFi PCR 2× MASTER MIX™ (Kapa Biosystems, Woburn, Mass.). Alternative mRNAs are post-transcriptionally capped using recombinant Vaccinia Virus Capping Enzyme (New England BioLabs, Ipswich, Mass.) and a recombinant 2'-O-methyl-transferase (Epicenter Biotechnologies, Madison, Wis.) to generate the 5'-guanosine Cap1 structure. Cap 2 structure and Cap 2 structures may be generated using additional 2'-O-methyltransferases. The In vitro transcribed mRNA product is run on an agarose gel and visualized. Alternative mRNA may be purified with Ambion/Applied Biosystems (Austin, Tex.) MEGAClear RNA™ purification kit. The PCR uses PURELINK™ PCR purification kit (Invitrogen, Carlsbad, Calif.). The product is quantified on NANO-DROP™ UV Absorbance (ThermoFisher, Waltham, Mass.). Quality, UV absorbance quality and visualization of the product was performed on an 1.2% agarose gel. The product is resuspended in TE buffer.

B. 5'-capping Alternative Nucleic Acid (mRNA) Structure

5'-capping of alternative mRNA may be completed concomitantly during the in vitro-transcription reaction using the following chemical RNA cap analogs to generate the 5'-guanosine cap structure according to manufacturer protocols: 3'-O-Me-m$^7$G(5')ppp(5')G (the ARCA cap); G(5')ppp(5')A; G(5')ppp(5')G; m$^7$G(5')ppp(5')A; m$^7$G(5')ppp(5')G (New England BioLabs, Ipswich, Mass.). 5'-capping of alternative mRNA may be completed post-transcriptionally using a Vaccinia Virus Capping Enzyme to generate the "Cap 0" structure: m$^7$G(5')ppp(5')G (New England BioLabs, Ipswich, Mass.). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes are preferably derived from a recombinant source.

When transfected into mammalian cells, the alternative mRNAs have a stability of 12-18 hours or more than 18 hours, e.g., 24, 36, 48, 60, 72 or greater than 72 hours.

Example 5. PolyA Tailing Reaction

Without a poly-T in the cDNA, a poly-A tailing reaction must be performed before cleaning the final product. This is done by mixing Capped IVT RNA (100 µl); RNase Inhibitor (20 U); 10× Tailing Buffer (0.5 M Tris-HCl (pH 8.0), 2.5 M NaCl, 100 mM MgCl$_2$)(12.0 µl); 20 mM ATP (6.0 µl); Poly-A Polymerase (20 U); dH$_2$O up to 123.5 µl and incubation at 37° C. for 30 min. If the poly-A tail is already in the transcript, then the tailing reaction may be skipped and proceed directly to cleanup with Ambion's MEGA-CLEAR™ kit (Austin, Tex.) (up to 500 µg). Poly-A Polymerase is preferably a recombinant enzyme expressed in yeast.

For studies performed and described herein, the poly-A tail is encoded in the IVT template to comprise 160 nucleotides in length. However, it should be understood that the processivity or integrity of the poly-A tailing reaction may not always result in exactly 160 nucleotides. Hence poly-A tails of approximately 160 nucleotides, acid about 150-165, 155, 156, 157, 158, 159, 160, 161, 162, 163, 164 or 165 are within the scope of the invention.

Example 6. In Vivo Expression of Selected Sequences

Figure 2:
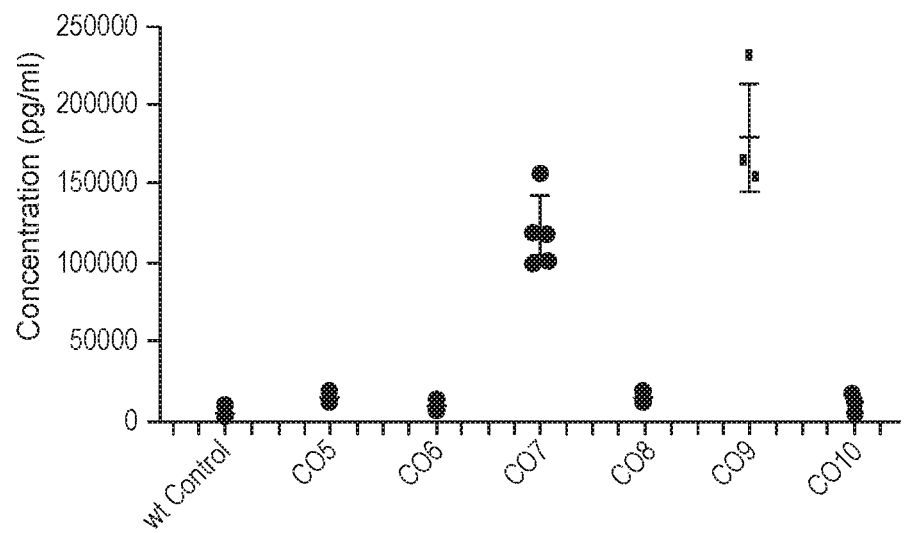
FIG. 2 is a graph of protein expression by uridine-minimized mRNA relative to the corresponding wild-type mRNA.

FIG. 1 shows in vivo expression data corresponding to control expression of Target Protein 2 compared to the expression data for constructs generated using 4 novel codon sets (CO1, CO2, CO3 and CO4), after intravenous administration of 0.05 mg/kg of each construct in MC3-LNP to mice. Similarly, FIG. 2 shows in vivo expression data corresponding to control expression of Target Protein 2 compared to the expression data for constructs generated using 6 novel codon sets (CO5, CO6, CO7, CO8, CO9 and CO10).

TABLE 11

Uracil Content of Selected Sequences

| Sequence | Uracil Content |
|---|---|
| CO1 | 23% uracil |
| CO2 | 27% uracil |
| CO3 | 13% uracil + only 4 uracil pairs |
| CO4 | 17% uracil |
| CO7 | 13% uracil + only 4 uracil pairs |
| CO9 | 14.7% uracil + only 4 uracil pairs |

Example 7. Method of Screening for Protein Expression

A. Electrospray Ionization

A biological sample which may contain proteins encoded by alternative RNA administered to the subject is prepared and analyzed according to the manufacturer protocol for electrospray ionization (ESI) using 1, 2, 3 or 4 mass analyzers. A biologic sample may also be analyzed using a tandem ESI mass spectrometry system.

Patterns of protein fragments, or whole proteins, are compared to known controls for a given protein and identity is determined by comparison.

B. Matrix-Assisted Laser Desorption/Ionization

A biological sample which may contain proteins encoded by alternative RNA administered to the subject is prepared and analyzed according to the manufacturer protocol for matrix-assisted laser desorption/ionization (MALDI).

Patterns of protein fragments, or whole proteins, are compared to known controls for a given protein and identity is determined by comparison.

C. Liquid Chromatography-Mass Spectrometry-Mass Spectrometry

A biological sample, which may contain proteins encoded by alternative RNA, may be treated with a trypsin enzyme to digest the proteins contained within. The resulting peptides are analyzed by liquid chromatography-mass spectrometry-mass spectrometry (LC/MS/MS). The peptides are fragmented in the mass spectrometer to yield diagnostic patterns that can be matched to protein sequence databases via computer algorithms. The digested sample may be diluted to achieve 1 ng or less starting material for a given protein. Biological samples containing a simple buffer background (e.g., water or volatile salts) are amenable to direct in-solution digest; more complex backgrounds (e.g., detergent, non-volatile salts, glycerol) require an additional clean-up step to facilitate the sample analysis.

Patterns of protein fragments, or whole proteins, are compared to known controls for a given protein and identity is determined by comparison.

Example 8. Transfection

A. Reverse Transfection

For experiments performed in a 24-well collagen-coated tissue culture plate, Keratinocytes or other cells are seeded at a cell density of 1×10$^5$. For experiments performed in a 96-well collagen-coated tissue culture plate, Keratinocytes are seeded at a cell density of 0.5×10$^5$. For each alternative mRNA to be transfected, alternative mRNA: RNAIMAX™ are prepared as described and mixed with the cells in the multi-well plate within 6 hours of cell seeding before cells had adhered to the tissue culture plate.

B. Forward Transfection

In a 24-well collagen-coated tissue culture plate, cells are seeded at a cell density of 0.7×10$^5$. For experiments performed in a 96-well collagen-coated tissue culture plate, keratinocytes, if used, are seeded at a cell density of 0.3×10$^5$. Cells are then grown to a confluency of >70% for over 24 hours. For each alternative mRNA to be transfected, alternative mRNA: RNAIMAX™ are prepared as described and transfected onto the cells in the multi-well plate over 24 hours after cell seeding and adherence to the tissue culture plate.

C. Translation Screen: ELISA

Cells are grown in EpiLife medium with Supplement S7 from Invitrogen at a confluence of >70%. Cells are reverse transfected with 300 ng of the indicated chemically alternative mRNA complexed with RNAIMAX™ from Invitrogen. Alternatively, cells are forward transfected with 300 ng alternative mRNA complexed with RNAIMAX™ from Invitrogen. The RNA: RNAIMAX™ complex is formed by first incubating the RNA with Supplement-free EPILIFE® media in a 5× volumetric dilution for 10 minutes at room temperature.

In a second vial, RNAIMAX™ reagent is incubated with Supplement-free EPILIFE® Media in a 10× volumetric dilution for 10 minutes at room temperature. The RNA vial is then mixed with the RNAIMAX™ vial and incubated for 20-30 at room temperature before being added to the cells in a drop-wise fashion. Secreted polypeptide concentration in the culture medium is measured at 18 hours post-transfection for each of the chemically alternative mRNAs in triplicate. Secretion of the polypeptide of interest from transfected human cells is quantified using an ELISA kit from Invitrogen or R&D Systems (Minneapolis, Minn.) following the manufacturer's recommended instructions.

D. Dose and Duration: ELISA

Cells are grown in EPILIFE® medium with Supplement S7 from Invitrogen at a confluence of >70%. Cells are reverse transfected with 0 ng, 46.875 ng, 93.75 ng, 187.5 ng, 375 ng, 750 ng, or 1500 ng alternative mRNA complexed with RNAIMAX™ from Invitrogen. The alternative mRNA: RNAIMAX™ complex is formed as described. Secreted polypeptide concentration in the culture medium is measured at 0, 6, 12, 24, and 48 hours post-transfection for each concentration of each alternative mRNA in triplicate. Secretion of the polypeptide of interest from transfected human cells is quantified using an ELISA kit from Invitrogen or R&D Systems following the manufacturers recommended instructions.

Example 9. Cellular Innate Immune Response: IFN-Beta ELISA and TNF-Alpha ELISA

An enzyme-linked immunosorbent assay (ELISA) for Human Tumor Necrosis Factor-α (TNF-α), Human Interferon-β (IFN-β) and Human Granulocyte-Colony Stimulating Factor (G-CSF) secreted from in vitro-transfected Human Keratinocyte cells is tested for the detection of a cellular innate immune response.

Cells are grown in EPILIFE® medium with Human Growth Supplement in the absence of hydrocortisone from Invitrogen at a confluence of >70%. Cells are reverse transfected with 0 ng, 93.75 ng, 187.5 ng, 375 ng, 750 ng, 1500 ng or 3000 ng of the indicated chemically alternative mRNA complexed with RNAIMAX™ from Invitrogen as described in triplicate. Secreted TNF-α in the culture medium is measured 24 hours post-transfection for each of the chemically alternative mRNAs using an ELISA kit from Invitrogen according to the manufacturer protocols.

Secreted IFN-β is measured 24 hours post-transfection for each of the alternative mRNAs using an ELISA kit from Invitrogen according to the manufacturer protocols. Secreted hu-G-CSF concentration is measured at 24 hours post-transfection for each of the alternative mRNAs. Secretion of the polypeptide of interest from transfected human cells is quantified using an ELISA kit from Invitrogen or R&D Systems (Minneapolis, Minn.) following the manufacturers recommended instructions. These data indicate which alternative mRNA are capable eliciting a reduced cellular innate immune response in comparison to natural and other alternative polynucleotides or reference compounds by measuring exemplary type 1 cytokines such as TNF-alpha and IFN-beta.

Example 10. Cytotoxicity and Apoptosis

This experiment demonstrates cellular viability, cytotoxity and apoptosis for distinct alternative mRNA-in vitro transfected Human Keratinocyte cells. Keratinocytes are grown in EPILIFE® medium with Human Keratinocyte Growth Supplement in the absence of hydrocortisone from Invitrogen at a confluence of >70%. Keratinocytes are reverse transfected with 0 ng, 46.875 ng, 93.75 ng, 187.5 ng, 375 ng, 750 ng, 1500 ng, 3000 ng, or 6000 ng of alternative mRNA complexed with RNAIMAX™ from Invitrogen. The alternative mRNA: RNAIMAX™ complex is formed. Secreted huG-CSF concentration in the culture medium is measured at 0, 6, 12, 24, and 48 hours post-transfection for each concentration of each alternative mRNA in triplicate. Secretion of the polypeptide of interest from transfected human keratinocytes is quantified using an ELISA kit from Invitrogen or R&D Systems following the manufacturers recommended instructions. Cellular viability, cytotoxicity and apoptosis is measured at 0, 12, 48, 96, and 192 hours post-transfection using the APOTOX-GLO™ kit from Promega (Madison, Wis.) according to manufacturer instructions.

Example 11. In Vivo Assays with Human EPO Containing Alternative Nucleotides

Formulation

Alternative hEPO mRNAs were formulated in lipid nanoparticles (LNPs) comprising DLin-KC2-DMA, DSPC, Cholesterol, and PEG-DMG at 50:10:38.5:1.5 mol % respectively (Table 12). The LNPs were made by direct injection utilizing nanoprecipitation of ethanol solubilized lipids into a pH 4.0 50 mM citrate mRNA solution. The EPO LNP particle size distributions were characterized by DLS. Encapsulation efficiency (EE) was determined using a Ribogreen™ fluorescence-based assay for detection and quantification of nucleic acids.

TABLE 12

| Formulation Conditions | | | |
| --- | --- | --- | --- |
| Ionizable Lipid 2-(2,2-di((9Z,12Z)-octadeca-9,12-dien-1yl)-1,3-diocolan-4-yl)-N,N-dimethylethanamine (Lipid/Mol %) | Phospholipid 1,2-distearoyl-sn-glycero-3-phosphocholine (Lipid/Mol %) | Cholesterol cholest-5-en-3β-ol (Lipid/Mol %) | PEG Lipid 1,2-Dimyristoyl-sn-glycerol, methoxypolyethylene Glycol (Lipid/Mol %) |
| DLin-KC2-DMA 50 | DSPC 10 | Cholesterol 38.5 | PEG-DMG 1.5 |

Methods and Data

Female Balb/c mice (n=5) were administered 0.05 mg/kg IM (50 μl in the quadriceps) or IV (100 μl in the tail vein) of human EPO mRNA. At time 8 hours after the injection mice were euthanized and blood was collected in serum separator tubes. The samples were spun, and serum samples were then run on an EPO ELISA following the kit protocol (Stem Cell Technologies Catalog #01630).

Example 12. mRNA Sequences for Constructs Used to Screen Compounds of the Invention

```
hEPO DNA2.0 sequence (SEQ ID NO: 5):
TCAAGCTTTTGGACCCTCGTACAGAAGCTAATACGACTCACTATAGGGAAATAAGAGAGAAAAGAAG

AGTAAGAAGAAATATAAGAGCCACCATGGGAGTGCACGAGTGTCCCGCGTGGTTGTGGTTGCTGCT

GTCGCTCTTGAGCCTCCCACTGGGACTGCCTGTGCTGGGGGCACCACCCAGATTGATCTGCGACTC

ACGGGTACTTGAGAGGTACCTTCTTGAAGCCAAAGAAGCCGAAAACATCACAACCGGATGCGCCGA

GCACTGCTCCCTCAATGAGAACATTACTGTACCGGATACAAAGGTCAATTTCTATGCATGGAAGAGA

ATGGAAGTAGGACAGCAGGCCGTCGAAGTGTGGCAGGGGCTCGCGCTTTTGTCGGAGGCGGTGTT

GCGGGGTCAGGCCCTCCTCGTCAACTCATCACAGCCGTGGGAGCCCCTCCAACTTCATGTCGATAA

AGCGGTGTCGGGGCTCCGCAGCTTGACGACGTTGCTTCGGGCTCTGGGCGCACAAAAGGAGGCTA

TTTCGCCGCCTGACGCGGCCTCCGCGGCACCCCTCCGAACGATCACCGCGGACACGTTTAGGAAG

CTTTTTAGAGTGTACAGCAATTTCCTCCGCGGAAAGCTGAAATTGTATACTGGTGAAGCGTGTAGGA

CAGGGGATCGCTGATAATAGGCTGGAGCCTCGGTGGCCATGCTTCTTGCCCCTTGGGCCTCCCCCC

AGCCCCTCCTCCCCTTCCTGCACCCGTACCCCCGTGGTCTTTGAATAAAGTCTGAGTGGGCGGCTC

TAGA hEPO C09 sequence (SEQ ID NO: 6):
TCAAGCTTTTGGACCCTCGTACAGAAGCTAATACGACTCACTATAGGGAAATAAGAGAGAAAAGAAG

AGTAAGAAGAAATATAAGAGCCACCATGGGCGTGCACGAGTGCCCCGCCTGGCTGTGGCTGCTGCT

GAGCCTGCTGAGCCTGCCCCTGGGCCTGCCCGTGCTGGGCGCCCCCCCCGCCTCATCTGCGACT

CCCGCGTCCTCGAGCGCTACCTCCTCGAGGCCAAGGAGGCCGAGAACATCACCACCGGCTGCGCC

GAGCACTGCTCCCTCAACGAGAACATCACCGTCCCCGACACCAAGGTCAACTTCTACGCCTGGAAG

CGCATGGAGGTCGGCCAGCAGGCCGTCGAGGTCTGGCAGGGCCTCGCCCTCCTCTCCGAGGCCGT

CCTCCGCGGCCAGGCCCTCCTCGTCAACTCCTCCCAGCCCTGGGAGCCCCTCCAGCTCCACGTCG

ACAAGGCCGTCTCCGGCCTCCGCTCCCTCACCACCCTCCTCCGCGCCCTCGGCGCCCAGAAGGAG

GCCATCTCCCCCCCCGACGCCGCCTCCGCCGCCCCCCTCCGCACCATCACCGCCGACACCTTCCG

CAAGCTCTTCCGCGTCTACTCCAACTTCCTCCGCGGCAAGCTCAAGCTCTACACCGGCGAGGCCTG

CCGCACCGGCGACCGCTGATAATAGGCTGGAGCCTCGGTGGCCATGCTTCTTGCCCCTTGGGCCTC

CCCCCAGCCCCTCCTCCCCTTCCTGCACCCGTACCCCCGTGGTCTTTGAATAAAGTCTGAGTGGGC

GGC
```

GCSF DNA2.0 sequence (SEQ ID NO: 7):
TCAAGCTTTTGGACCCTCGTACAGAAGCTAATACGACTCACTATAGGGAAATAAGAGAGAAAAGAAG

AGTAAGAAGAAATATAAGAGCCACCATGGCCGGCCCCGCCACCCAGAGCCCCATGAAGCTGATGGC

CCTGCAGCTGCTGCTGTGGCACAGCGCCCTGTGGACCGTGCAGGAGGCCACACCTTTAGGACCTG

CTTCTTCTTTACCTCAATCTTTTTTATTAAAATGTTTAGAACAAGTTAGAAAAATTCAAGGAGATGGAG

CTGCTTTACAAGAAAAATTATGTGCTACATATAAATTATGTCATCCTGAAGAATTAGTTTTATTAGGAC

ATTCTTTAGGAATTCCTTGGGCTCCTTTATCTTCTTGTCCTTCTCAAGCTTTACAATTAGCTGGATGTT

TATCTCAATTACATTCTGGATTATTTTTATATCAAGGATTATTACAAGCTTTAGAAGGAATTTCTCCTGA

ATTAGGACCTACATTAGATACATTACAATTAGATGTTGCTGATTTTGCTACAACAATTTGGCAACAAAT

GGAAGAATTAGGAATGGCTCCTGCTTTACAACCTACACAAGGAGCTATGCCTGCTTTTGCTTCTGCTT

TTCAAAGAAGAGCTGGAGGAGTTTTAGTTGCTTCTCATTTACAATCTTTTTTAGAAGTTTCTTATAGAG

TTTTAAGACATTTAGCTCAACCTTGATAATAGGCTGGAGCCTCGGTGGCCATGCTTCTTGCCCCTTG

GGCCTCCCCCAGCCCCTCCTCCCCTTCCTGCACCCGTACCCCCGTGGTCTTTGAATAAAGTCTGA

GTGGGCGGC

GCSF C03 sequence (SEQ ID NO: 8):
TCAAGCTTTTGGACCCTCGTACAGAAGCTAATACGACTCACTATAGGGAAATAAGAGAGAAAAGAAG

AGTAAGAAGAAATATAAGAGCCACCATGGCCGGCCCCGCCACCCAGAGCCCCATGAAGCTGATGGC

CCTGCAGCTGCTGCTGTGGCACAGCGCCCTGTGGACCGTGCAGGAGGCCACCCCCTGGGCCCCG

CCAGCAGCCTGCCCCAGAGCTTCCTGCTGAAGTGCCTGGAGCAGGTGCGGAAGATCCAGGGCGAC

GGCGCCGCCCTGCAGGAGAAGCTGTGCGCCACCTACAAGCTGTGCCACCCCGAGGAGCTGGTGCT

GCTGGGCCACAGCCTGGGCATCCCCTGGGCCCCCCTGAGCAGCTGCCCCAGCCAGGCCCTGCAG

CTGGCCGGCTGCCTGAGCCAGCTGCACAGCGGCCTGTTCCTGTACCAGGGCCTGCTGCAGGCCCT

GGAGGGCATCAGCCCCGAGCTGGGCCCCACCCTGGACACCCTGCAGCTGGACGTGGCCGACTTCG

CCACCACCATCTGGCAGCAGATGGAGGAGCTGGGCATGGCCCCCGCCCTGCAGCCCACCCAGGGC

GCCATGCCCGCCTTCGCCAGCGCCTTCCAGCGGCGGGCCGGCGGCGTGCTGGTGGCCAGCCACC

TGCAGAGCTTCCTGGAGGTGAGCTACCGGGTGCTGCGGCACCTGGCCCAGCCCTGATAATAGGCT

GGAGCCTCGGTGGCCATGCTTCTTGCCCCTTGGGCCTCCCCCAGCCCCTCCTCCCCTTCCTGCAC

CCGTACCCCCGTGGTCTTTGAATAAAGTCTGAGTGGGCGGC

GCSF C07 sequence (SEQ ID NO: 9):
TCAAGCTTTTGGACCCTCGTACAGAAGCTAATACGACTCACTATAGGGAAATAAGAGAGAAAAGAAG

AGTAAGAAGAAATATAAGAGCCACCATGGCCGGCCCCGCCACCCAGAGCCCCATGAAGCTGATGGC

CCTGCAGCTGCTGCTGTGGCACAGCGCCCTGTGGACCGTGCAGGAGGCCACGCCGCTGGGGCCG

GCGAGCAGCCTGCCGCAGAGCTTCCTGCTGAAGTGCCTGGAGCAGGTGAGGAAGATCCAGGGGGA

CGGGGCGGCGCTGCAGGAGAAGCTGTGCGCGACGTACAAGCTGTGCCACCCGGAGGAGCTGGTG

CTGCTGGGGCACAGCCTGGGGATCCCGTGGGCGCCGCTGAGCAGCTGCCCGAGCCAGGCGCTGC

AGCTGGCGGGGTGCCTGAGCCAGCTGCACAGCGGGCTGTTCCTGTACCAGGGGCTGCTGCAGGCG

CTGGAGGGGATCAGCCCGGAGCTGGGGCCGACGCTGGACACGCTGCAGCTGGACGTGGCGGACT

TCGCGACGACGATCTGGCAGCAGATGGAGGAGCTGGGGATGGCGCCGGCGCTGCAGCCGACGCA

GGGGGCGATGCCGGCGTTCGCGAGCGCGTTCCAGAGGAGGGCGGGGGGGTGCTGGTGGCGAG

CCACCTGCAGAGCTTCCTGGAGGTGAGCTACAGGGTGCTGAGGCACCTGGCGCAGCCGTGATAATA

GGCTGGAGCCTCGGTGGCCATGCTTCTTGCCCCTTGGGCCTCCCCCAGCCCCTCCTCCCCTTCCT

GCACCCGTACCCCCGTGGTCTTTGAATAAAGTCTGAGTGGGCGGC

GCSF C09 sequence (SEQ ID NO: 10):
TCAAGCTTTTGGACCCTCGTACAGAAGCTAATACGACTCACTATAGGGAAATAAGAGAGAAAAGAAG

AGTAAGAAGAAATATAAGAGCCACCATGGCCGGCCCCGCCACCCAGAGCCCCATGAAGCTGATGGC

CCTGCAGCTGCTGCTGTGGCACAGCGCCCTGTGGACCGTGCAGGAGGCCACCCCCCTCGGCCCCG

CCTCCTCCCTCCCCCAGTCCTTCCTCCTCAAGTGCCTCGAGCAGGTCCGCAAGATCCAGGGCGACG

GCGCCGCCCTCCAGGAGAAGCTCTGCGCCACCTACAAGCTCTGCCACCCCGAGGAGCTCGTCCTC

CTCGGCCACTCCCTCGGCATCCCCTGGGCCCCCCTCTCCTCCTGCCCCTCCCAGGCCCTCCAGCTC

GCCGGCTGCCTCTCCCAGCTCCACTCCGGCCTCTTCCTCTACCAGGGCCTCCTCCAGGCCCTCGAG

GGCATCTCCCCCGAGCTCGGCCCCACCCTCGACACCCTCCAGCTCGACGTCGCCGACTTCGCCAC

CACCATCTGGCAGCAGATGGAGGAGCTCGGCATGGCCCCCGCCCTCCAGCCCACCCAGGGCGCCA

TGCCCGCCTTCGCCTCCGCCTTCCAGCGCCGCGCCGGCGGCGTCCTCGTCGCCTCCCACCTCCAG

TCCTTCCTCGAGGTCTCCTACCGCGTCCTCCGCCACCTCGCCCAGCCCTGATAATAGGCTGGAGCC

TCGGTGGCCATGCTTCTTGCCCCTTGGGCCTCCCCCAGCCCCTCCTCCCCTTCCTGCACCCGTAC

CCCCGTGGTCTTTGAATAAAGTCTGAGTGGGCGGC

Luc DNA2.0 sequence (SEQ ID NO: 11):
TCAAGCTTTTGGACCCTCGTACAGAAGCTAATACGACTCACTATAGGGAAATAAGAGAGAAAAGAAG

AGTAAGAAGAAATATAAGAGCCACCATGGAAGATGCGAAGAACATCAAGAAGGGACCTGCCCCGTTT

TACCCTTTGGAGGACGGTACAGCAGGAGAACAGCTCCACAAGGCGATGAAACGCTACGCCCTGGTC

CCCGGAACGATTGCGTTTACCGATGCACATATTGAGGTAGACATCACATACGCAGAATACTTCGAAA

TGTCGGTGAGGCTGGCGGAAGCGATGAAGAGATATGGTCTTAACACTAATCACCGCATCGTGGTGT

GTTCGGAGAACTCATTGCAGTTTTTCATGCCGGTCCTTGGAGCACTTTTCATCGGGGTCGCAGTCGC

GCCAGCGAACGACATCTACAATGAGCGGGAACTCTTGAATAGCATGGGAATCTCCCAGCCGACGGT

CGTGTTTGTCTCCAAAAAGGGGCTGCAGAAAATCCTCAACGTGCAGAAGAAGCTCCCCATTATTCAA

AAGATCATCATTATGGATAGCAAGACAGATTACCAAGGGTTCCAGTCGATGTATACCTTTGTGACATC

GCATTTGCCGCCAGGGTTTAACGAGTATGACTTCGTCCCCGAGTCATTTGACAGAGATAAAACCATC

GCGCTGATTATGAATTCCTCGGGTAGCACCGGTTTGCCAAAGGGGGTGGCGTTGCCCCACCGCACT

GCTTGTGTGCGGTTCTCGCACGCTAGGGATCCTATCTTTGGTAATCAGATCATTCCCGACACAGCAA

TCCTGTCCGTGGTACCTTTTCATCACGGTTTTGGCATGTTCACGACTCTCGGCTATTTGATTTGCGGT

TTCAGGGTCGTACTTATGTATCGGTTCGAGGAAGAACTGTTTTTGAGATCCTTGCAAGATTACAAGAT

CCAGTCGGCCCTCCTTGTGCCAACGCTTTTCTCATTCTTTGCGAAATCGACACTTATTGATAAGTATG

ACCTTTCCAATCTGCATGAGATTGCCTCAGGGGGAGCGCCGCTTAGCAAGGAAGTCGGGGAGGCAG

TGGCCAAGCGCTTCCACCTTCCCGGAATTCGGCAGGGATACGGGCTCACGGAGACAACATCCGCGA

TCCTTATCACGCCCGAGGGTGACGATAAGCCGGGAGCCGTCGGAAAAGTGGTCCCCTTCTTTGAAG

CCAAGGTCGTAGACCTCGACACGGGAAAAACCCTCGGAGTGAACCAGAGGGGCGAGCTCTGCGTG

AGAGGGCCGATGATCATGTCAGGTTACGTGAATAACCCTGAAGCGACGAATGCGCTGATCGACAAG

GATGGGTGGTTGCATTCGGAGACATTGCCTATGGGATGAGGATGAGCACTTCTTTATCGTAGATC

GACTTAAGAGCTTGATCAAATACAAAGGCTATCAGGTAGCGCCTGCCGAGCTCGAGTCAATCCTGCT

CCAGCACCCCAACATTTTCGACGCCGGAGTGGCCGGGTTGCCCGATGACGACGCGGGTGAGCTGC

CAGCGGCCGTGGTAGTCCTCGAACATGGGAAAACAATGACCGAAAAGGAGATCGTGGACTACGTAG

CATCACAAGTGACGACTGCGAAGAAACTGAGGGGAGGGGTAGTCTTTGTGGACGAGGTCCCGAAAG

GCTTGACTGGGAAGCTTGACGCTCGCAAAATCCGGGAAATCCTGATTAAGGCAAAGAAAGGCGGGA

```
AAATCGCTGTCTGATAATAGGCTGGAGCCTCGGTGGCCATGCTTCTTGCCCCTTGGGCCTCCCCCC

AGCCCCTCCTCCCCTTCCTGCACCCGTACCCCGTGGTCTTTGAATAAAGTCTGAGTGGGCGGC

Luc CO3 sequence (SEQ ID NO: 12):
TCAAGCTTTTGGACCCTCGTACAGAAGCTAATACGACTCACTATAGGGAAATAAGAGAGAAAAGAAG

AGTAAGAAGAAATATAAGAGCCACCATGGAGGACGCCAAGAACATCAAGAAGGGCCCCGCCCCCTT

CTACCCCCTGGAGGACGGCACCGCCGGCGAGCAGCTGCACAAGGCCATGAAGCGGTACGCCCTGG

TGCCCGGCACCATCGCCTTCACCGACGCCCACATCGAGGTGGACATCACCTACGCCGAGTACTTCG

AGATGAGCGTGCGGCTGGCCGAGGCCATGAAGCGGTACGGCCTGAACACCAACCACCGGATCGTG

GTGTGCAGCGAGAACAGCCTGCAGTTCTTCATGCCCGTGCTGGGCGCCCTGTTCATCGGCGTGGCC

GTGGCCCCCGCCAACGACATCTACAACGAGCGGGAGCTGCTGAACAGCATGGGCATCAGCCAGCC

CACCGTGGTGTTCGTGAGCAAGAAGGGCCTGCAGAAGATCCTGAACGTGCAGAAGAAGCTGCCCAT

CATCCAGAAGATCATCATCATGGACAGCAAGACCGACTACCAGGGCTTCCAGAGCATGTACACCTTC

GTGACCAGCCACCTGCCCCCCGGCTTCAACGAGTACGACTTCGTGCCCGAGAGCTTCGACCGGGA

CAAGACCATCGCCCTGATCATGAACAGCAGCGGCAGCACCGGCCTGCCCAAGGGCGTGGCCCTGC

CCCACCGGACCGCCTGCGTGCGGTTCAGCCACGCCCGGGACCCCATCTTCGGCAACCAGATCATC

CCCGACACCGCCATCCTGAGCGTGGTGCCCTTCCACCACGGCTTCGGCATGTTCACCACCCTGGGC

TACCTGATCTGCGGCTTCCGGGTGGTGCTGATGTACCGGTTCGAGGAGGAGCTGTTCCTGCGGAGC

CTGCAGGACTACAAGATCCAGAGCGCCCTGCTGGTGCCCACCCTGTTCAGCTTCTTCGCCAAGAGC

ACCCTGATCGACAAGTACGACCTGAGCAACCTGCACGAGATCGCCAGCGGCGGCGCCCCCCTGAG

CAAGGAGGTGGGCGAGGCCGTGGCCAAGCGGTTCCACCTGCCCGGCATCCGGCAGGGCTACGGC

CTGACCGAGACCACCAGCGCCATCCTGATCACCCCCGAGGGCGACGACAAGCCCGGCGCCGTGGG

CAAGGTGGTGCCCTTCTTCGAGGCCAAGGTGGTGGACCTGGACACCGGCAAGACCCTGGGCGTGA

ACCAGCGGGGCGAGCTGTGCGTGCGGGGCCCCATGATCATGAGCGGCTACGTGAACAACCCCGAG

GCCACCAACGCCCTGATCGACAAGGACGGCTGGCTGCACAGCGGCGACATCGCCTACTGGGACGA

GGACGAGCACTTCTTCATCGTGGACCGGCTGAAGAGCCTGATCAAGTACAAGGGCTACCAGGTGGC

CCCCGCCGAGCTGGAGAGCATCCTGCTGCAGCACCCCAACATCTTCGACGCCGGCGTGGCCGGCC

TGCCCGACGACGACGCCGGCGAGCTGCCCGCCGCCGTGGTGGTGCTGGAGCACGGCAAGACCAT

GACCGAGAAGGAGATCGTGGACTACGTGGCCAGCCAGGTGACCACCGCCAAGAAGCTGCGGGGCG

GCGTGGTGTTCGTGGACGAGGTGCCCAAGGGCCTGACCGGCAAGCTGGACGCCCGGAAGATCCG

GGAGATCCTGATCAAGGCCAAGAAGGGCGGCAAGATCGCCGTGTGATAATAGGCTGGAGCCTCGG

TGGCCATGCTTCTTGCCCCTTGGGCCTCCCCCCAGCCCCTCCTCCCCTTCCTGCACCCGTACCCCC

GTGGTCTTTGAATAAAGTCTGAGTGGGCGGC

Luc CO7 sequence (SEQ ID NO: 13):
TCAAGCTTTTGGACCCTCGTACAGAAGCTAATACGACTCACTATAGGGAAATAAGAGAGAAAAGAAG

AGTAAGAAGAAATATAAGAGCCACCATGGAGGACGCCAAGAACATCAAGAAGGGCCCCGCCCCCTT

CTACCCCCTGGAGGACGGCACCGCCGGCGAGCAGCTGCACAAGGCCATGAAGAGGTACGCGCTGG

TGCCGGGGACGATCGCGTTCACGGACGCGCACATCGAGGTGGACATCACGTACGCGGAGTACTTC

GAGATGAGCGTGAGGCTGGCGGAGGCGATGAAGAGGTACGGGCTGAACACGAACCACAGGATCGT

GGTGTGCAGCGAGAACAGCCTGCAGTTCTTCATGCCGGTGCTGGGGGCGCTGTTCATCGGGGTGG

CGGTGGCGCCGGCGAACGACATCTACAACGAGAGGGAGCTGCTGAACAGCATGGGGATCAGCCAG

CCGACGGTGGTGTTCGTGAGCAAGAAGGGGCTGCAGAAGATCCTGAACGTGCAGAAGAAGCTGCC

GATCATCCAGAAGATCATCATCATGGACAGCAAGACGGACTACCAGGGGTTCCAGAGCATGTACAC
```

GTTCGTGACGAGCCACCTGCCGCCGGGGTTCAACGAGTACGACTTCGTGCCGGAGAGCTTCGACA

GGGACAAGACGATCGCGCTGATCATGAACAGCAGCGGGAGCACGGGGCTGCCGAAGGGGGTGGC

GCTGCCGCACAGGACGGCGTGCGTGAGGTTCAGCCACGCGAGGGACCCGATCTTCGGGAACCAGA

TCATCCCGGACACGGCGATCCTGAGCGTGGTGCCGTTCCACCACGGGTTCGGGATGTTCACGACG

CTGGGGTACCTGATCTGCGGGTTCAGGGTGGTGCTGATGTACAGGTTCGAGGAGGAGCTGTTCCTG

AGGAGCCTGCAGGACTACAAGATCCAGAGCGCGCTGCTGGTGCCGACGCTGTTCAGCTTCTTCGCG

AAGAGCACGCTGATCGACAAGTACGACCTGAGCAACCTGCACGAGATCGCGAGCGGGGGGCGCC

GCTGAGCAAGGAGGTGGGGGAGGCGGTGGCGAAGAGGTTCCACCTGCCGGGGATCAGGCAGGGG

TACGGGCTGACGGAGACGACGAGCGCGATCCTGATCACGCCGGAGGGGACGACAAGCCGGGGG

CGGTGGGGAAGGTGGTGCCGTTCTTCGAGGCGAAGGTGGTGGACCTGGACACGGGGAAGACGCT

GGGGGTGAACCAGAGGGGGGAGCTGTGCGTGAGGGGGCCGATGATCATGAGCGGGTACGTGAAC

AACCCGGAGGCGACGAACGCGCTGATCGACAAGGACGGGTGGCTGCACAGCGGGGACATCGCGTA

CTGGGACGAGGACGAGCACTTCTTCATCGTGGACAGGCTGAAGAGCCTGATCAAGTACAAGGGGTA

CCAGGTGGCGCCGGCGGAGCTGGAGAGCATCCTGCTGCAGCACCCGAACATCTTCGACGCGGGG

GTGGCGGGGCTGCCGGACGACGACGCGGGGGAGCTGCCGGCGGCGGTGGTGGTGCTGGAGCAC

GGGAAGACGATGACGGAGAAGGAGATCGTGGACTACGTGGCGAGCCAGGTGACGACGGCGAAGAA

GCTGAGGGGGGGGGTGGTGTTCGTGGACGAGGTGCCGAAGGGGCTGACGGGGAAGCTGGACGCG

AGGAAGATCAGGGAGATCCTGATCAAGGCGAAGAAGGGGGGGAAGATCGCGGTGTGATAATAGGC

TGGAGCCTCGGTGGCCATGCTTCTTGCCCCTTGGGCCTCCCCCAGCCCCTCCTCCCCTTCCTGCA

CCCGTACCCCCGTGGTCTTTGAATAAAGTCTGAGTGGGCGGC mCherry wild-type (SEQ ID NO: 14)
TCAAGCTTTTGGACCCTCGTACAGAAGCTAATACGACTCACTATAGGGAAATAAGAGAGAAAAGAAG

AGTAAGAAGAAATATAAGAGCCACCATGGTATCCAAGGGGGAGGAGGACAACATGGCGATCATCAA

GGAGTTCATGCGATTCAAGGTGCACATGGAAGGTTCGGTCAACGGACACGAATTTGAAATCGAAGG

AGAGGGTGAAGGAAGGCCCTATGAAGGGACACAGACCGCGAAACTCAAGGTCACGAAAGGGGGAC

CACTTCCTTTCGCCTGGGACATTCTTTCGCCCCAGTTTATGTACGGGTCCAAAGCATATGTGAAGCAT

CCCGCCGATATTCCTGACTATCTGAAACTCAGCTTTCCCGAGGGATTCAAGTGGGAGCGGGTCATGA

ACTTTGAGGACGGGGGTGTAGTCACCGTAACCCAAGACTCAAGCCTCCAAGACGGCGAGTTCATCT

ACAAGGTCAAACTGCGGGGACTAACTTTCCGTCGGATGGGCCGGTGATGCAGAAGAAAACGATGG

GATGGGAAGCGTCATCGGAGAGGATGTACCCAGAAGATGGTGCATTGAAGGGGAGATCAAGCAG

AGACTGAAGTTGAAAGATGGGGGACATTATGATGCCGAGGTGAAAACGACATACAAAGCGAAAAAG

CCGGTGCAGCTTCCCGGAGCGTATAATGTGAATATCAAGTTGGATATTACTTCACACAATGAGGACT

ACACAATTGTCGAACAGTACGAACGCGCTGAGGGTAGACACTCGACGGGAGGCATGGACGAGTTGT

ACAAATGATAATAGGCTGGAGCCTCGGTGGCCATGCTTCTTGCCCCTTGGGCCTCCCCCAGCCCC

TCCTCCCCTTCCTGCACCCGTACCCCCGTGGTCTTTGAATAAAGTCTGAGTGGGCGGC mCherry CO3 sequence (SEQ ID NO: 15)
TCAAGCTTTTGGACCCTCGTACAGAAGCTAATACGACTCACTATAGGGAAATAAGAGAGAAAAGAAG

AGTAAGAAGAAATATAAGAGCCACCATGGTGAGCAAGGGCGAGGAGGACAACATGGCCATCATCAA

GGAGTTCATGCGGTTCAAGGTGCACATGGAGGGCAGCGTGAACGGCCACGAGTTCGAGATCGAGG

GCGAGGGCGAGGGCCGGCCCTACGAGGGCACCCAGACCGCCAAGCTGAAGGTGACCAAGGGCGG

CCCCCTGCCCTTCGCCTGGGACATCCTGAGCCCCCAGTTCATGTACGGCAGCAAGGCCTACGTGAA

-continued

GCACCCCGCCGACATCCCCGACTACCTGAAGCTGAGCTTCCCCGAGGGCTTCAAGTGGGAGCGGG

TGATGAACTTCGAGGACGGCGGCGTGGTGACCGTGACCCAGGACAGCAGCCTGCAGGACGGCGAG

TTCATCTACAAGGTGAAGCTGCGGGGCACCAACTTCCCCAGCGACGGCCCCGTGATGCAGAAGAAG

ACCATGGGCTGGGAGGCCAGCAGCGAGCGGATGTACCCCGAGGACGGCGCCCTGAAGGGCGAGA

TCAAGCAGCGGCTGAAGCTGAAGGACGGCGGCCACTACGACGCCGAGGTGAAGACCACCTACAAG

GCCAAGAAGCCCGTGCAGCTGCCCGGCGCCTACAACGTGAACATCAAGCTGGACATCACCAGCCAC

AACGAGGACTACACCATCGTGGAGCAGTACGAGCGGGCCGAGGGCCGGCACAGCACCGGCGGCA

TGGACGAGCTGTACAAGTGATAATAGGCTGGAGCCTCGGTGGCCATGCTTCTTGCCCCTTGGGCCT

CCCCCCAGCCCCTCCTCCCCTTCCTGCACCCGTACCCCCGTGGTCTTTGAATAAAGTCTGAGTGGG

CGGC mCherry CO7 sequence (SEQ ID NO: 16)
TCAAGCTTTTGGACCCTCGTACAGAAGCTAATACGACTCACTATAGGGAAATAAGAGAGAAAAGAAG

AGTAAGAAGAAATATAAGAGCCACCATGGTGAGCAAGGGCGAGGAGGACAACATGGCCATCATCAA

GGAGTTCATGCGGTTCAAGGTGCACATGGAGGGCAGCGTGAACGGCCACGAGTTCGAGATCGAGG

GGGAGGGGGAGGGGAGGCCGTACGAGGGGACGCAGACGGCGAAGCTGAAGGTGACGAAGGGGG

GGCCGCTGCCGTTCGCGTGGGACATCCTGAGCCCGCAGTTCATGTACGGGAGCAAGGCGTACGTG

AAGCACCCGGCGGACATCCCGGACTACCTGAAGCTGAGCTTCCCGGAGGGGTTCAAGTGGGAGAG

GGTGATGAACTTCGAGGACGGGGGGGTGGTGACGGTGACGCAGGACAGCAGCCTGCAGGACGGG

GAGTTCATCTACAAGGTGAAGCTGAGGGGGACGAACTTCCCGAGCGACGGGCCGGTGATGCAGAA

GAAGACGATGGGGTGGGAGGCGAGCAGCGAGAGGATGTACCCGGAGGACGGGGCGCTGAAGGGG

GAGATCAAGCAGAGGCTGAAGCTGAAGGACGGGGGGCACTACGACGCGGAGGTGAAGACGACGTA

CAAGGCGAAGAAGCCGGTGCAGCTGCCGGGGGCGTACAACGTGAACATCAAGCTGGACATCACGA

GCCACAACGAGGACTACACGATCGTGGAGCAGTACGAGAGGGCGGAGGGGAGGCACAGCACGGGG

GGGGATGGACGAGCTGTACAAGTGATAATAGGCTGGAGCCTCGGTGGCCATGCTTCTTGCCCCTTG

GGCCTCCCCCCAGCCCCTCCTCCCCTTCCTGCACCCGTACCCCCGTGGTCTTTGAATAAAGTCTGA

GTGGGCGGC mCherry CO9 sequence (SEQ ID NO: 17)
TCAAGCTTTTGGACCCTCGTACAGAAGCTAATACGACTCACTATAGGGAAATAAGAGAGAAAAGA

AGAGTAAGAAGAAATATAAGAGCCACCATGGTGAGCAAGGGCGAGGAGGACAACATGGCCATC

ATCAAGGAGTTCATGCGGTTCAAGGTGCACATGGAGGGCAGCGTGAACGGCCACGAGTTCGAG

ATCGAGGGCGAGGGCGAGGGCCGCCCCTACGAGGGCACCCAGACCGCCAAGCTCAAGGTCAC

CAAGGGCGGCCCCCTCCCCTTCGCCTGGGACATCCTCTCCCCCCAGTTCATGTACGGCTCCAA

GGCCTACGTCAAGCACCCCGCCGACATCCCCGACTACCTCAAGCTCTCCTTCCCCGAGGGCTT

CAAGTGGGAGCGCGTCATGAACTTCGAGGACGGCGGCGTCGTCACCGTCACCCAGGACTCCTC

CCTCCAGGACGGCGAGTTCATCTACAAGGTCAAGCTCCGCGGCACCAACTTCCCCTCCGACGG

CCCCGTCATGCAGAAGAAGACCATGGGCTGGGAGGCCTCCTCCGAGCGCATGTACCCCGAGGA

CGGCGCCCTCAAGGGCGAGATCAAGCAGCGCCTCAAGCTCAAGGACGGCGGCCACTACGACG

CCGAGGTCAAGACCACCTACAAGGCCAAGAAGCCCGTCCAGCTCCCCGGCGCCTACAACGTCA

ACATCAAGCTCGACATCACCTCCCACAACGAGGACTACACCATCGTCGAGCAGTACGAGCGCG

CCGAGGGCCGCCACTCCACCGGCGGCATGGACGAGCTCTACAAGTGATAATAGGCTGGAGCCT

CGGTGGCCATGCTTCTTGCCCCTTGGGCCTCCCCCCAGCCCCTCCTCCCCTTCCTGCACCCGTA

CCCCCGTGGTCTTTGAATAAAGTCTGAGTGGGCGGC

Example 13. Transfection in HeLa Cells

The day before transfection, 20,000 HeLa cells (ATCC no. CCL-2; Manassas, Va.) were harvested by treatment with Trypsin-EDTA solution (LifeTechnologies, Grand Island, N.Y.) and seeded in a total volume of 100 µl EMEM medium (supplemented with 10% FCS and 1× Glutamax) per well in a 96-well cell culture plate (Corning, Manassas, Va.). The cells were grown at 37° C. in 5% $CO_2$ atmosphere overnight. Next day, 83 ng of Luciferase modRNA or 250 ng of human GCSF modRNA, harboring chemical alterations on the bases or the ribose units, were diluted in 10 µL final volume of OPTI-MEM (LifeTechnologies, Grand Island, N.Y.). Lipofectamine 2000 (LifeTechnologies, Grand Island, N.Y.) was used as transfection reagent and 0.2 µL were diluted in 10 µL final volume of OPTI-MEM. After 5 min incubation at room temperature, both solutions were combined and incubated additional 15 min at room temperature. Then the 20 µL were added to the 100 µL cell culture medium containing the HeLa cells. The plates were then incubated as described before. For transfection with mCherry or nano-Luc, a mixture of mRNA expressing mCherry or nanoLuc is mixed with 0.5 µL of Lipofectamine2000 (Life Technologies; cat#11668019) and OptiMem (Life Tehnologies; cat#31985062). A final volume of 20 µL of this mixture is added to 100 µL of cells. The final amount of human EPO, G-CSF, Firefly Luciferase, mCherry and nanoLuc mRNA used per well is 250 ng except for nanoLuc mRNA which we used at 25 ng per well, respectively.

After 18 h to 22 h incubation, cells expressing luciferase were lysed with 100 µl Passive Lysis Buffer (Promega, Madison, Wis.) according to manufacturer instructions. Aliquots of the lysates were transferred to white opaque polystyrene 96-well plates (Corning, Manassas, Va.) and combined with 100 µL complete luciferase assay solution (Promega, Madison, Wis.). The lysate volumes were adjusted or diluted until no more than 2 mio relative light units per well were detected for the strongest signal producing samples. The background signal of the plates without reagent was about 200 relative light units per well. The plate reader was a BioTek Synergy H1 (BioTek, Winooski, Vt.). The results are shown in Table 13.

For the cells transfected with mCherry, mCherry fluorescence reading was measured directly of the cells at excitation of 585 nm and emission of 615 nm wavelength. The results are shown in Table 14.

After 18 h to 22 h incubation, cell culture supernatants of cells expressing human EPO were collected and centrifuged at 10,000 rcf for 2 min. The cleared supernatants were transferred and analyzed with a human GCSF-specific or EPO ELISA kit (both from R&D Systems, Minneapolis, Minn.; Cat. #s SCS50, DEPOO, respectively) according to the manufacturer instructions. All samples were diluted until the determined values were within the linear range of the human EPO ELISA standard curve. The results are shown in Table 15.

TABLE 13

Expression of FFLuc in HeLa cells

| Construct | FFLuc expression (RLU; 24 hrs) |
|---|---|
| 1-methyl pseudo U (DNA2.0) | 78300 |
| 1-methyl pseudo U (CO7) | 115150 |
| 5-methoxy-uridine (CO3) | 162900 |
| 5-methoxy-uridine (CO7) | 68550 |
| 5-methoxy-uridine (CO9) | 93150 |

TABLE 14

Expression of mCherry in HeLa cells

| Construct | mCherry expression (FLU; 24 hrs) |
|---|---|
| 1-methyl pseudo U (WT) | 1137 |
| 1-methyl pseudo U (CO7) | 2229 |
| 5-methoxy-uridine (CO3) | 1464 |
| 5-methoxy-uridine (CO7) | 3007 |
| 5-methoxy-uridine (CO9) | 4344 |

TABLE 15

Expression of hEPO in HeLa cells

| Construct | hEPO expression in HeLa (mIU/mL; 24 hours) |
|---|---|
| 1-methyl pseudo U (DNA2.0) | 250537 |
| 5-methoxy-uridine (CO3) | 253718 |
| 5-methoxy-uridine (CO7) | 290925 |
| 5-methoxy-uridine (CO9) | 123977 |

Example 14. Transfection in BJ Fibroblasts

At 2 or 3 days prior to transfection, 100,000 BJ fibroblast cells (ATCC no. CRL-2522; Manassas, Va.) were harvested by treatment with trypsin-EDTA solution (LifeTechnologies, Grand Island, N.Y.) and seeded in a total volume of 500 µL EMEM medium (supplemented with 10% FCS and 10% Glutamax, both LifeTechnologies, Grand Island, N.Y.) per well in 24-well cell culture plates (Corning, Manassas, Va.). The cells were grown at 37° C. in a 5% $CO_2$ atmosphere overnight. On the next day, 500 ng modRNA, harboring chemical alterations on the bases or the ribose units, were diluted in 25 µL final volume of OPTI-MEM (LifeTechnologies, Grand Island, N.Y.). Lipofectamine 2000 (LifeTechnologies, Grand Island, N.Y.) was used as transfection reagent and 1.0 µL was diluted in 25 µL final volume of OPTI-MEM. After 5 min incubation at room temperature, both solutions were combined and incubated an additional 15 min at room temperature. The 50 µL were added to the 500 µL cell culture medium containing the BJ fibroblast cells. The plates were then incubated as described above.

After 18 h to 22 h incubation, cell culture supernatants of cells expressing human GCSF or human EPO were collected and centrifuged at 10,000 rcf for 2 min. The cleared supernatants were transferred and analyzed with a human GCSF-specific or EPO ELISA kit (both from R&D Systems, Minneapolis, Minn.; Cat. #s SCS50, DEPOO, respectively) according to the manufacturer instructions. All samples were diluted until the determined values were within the linear range of the human GCSF or EPO ELISA standard curve. The results are shown in Tables 16, 17, and 18.

TABLE 16

Expression of hEPO in BJ Fibroblast cells

| Construct | hEPO expression in BJ (mIU/mL; 48 hours) |
|---|---|
| 1-methyl pseudo U (DNA2.0) | 153713 |
| 5-methoxy-uridine (CO3) | 146050 |
| 5-methoxy-uridine (CO7) | 158195 |
| 5-methoxy-uridine (CO9) | 68986 |

TABLE 17

Expression of GCSF in BJ Fibroblast cells (25 ng/well)

| Construct | GCSF expression in BJ (pg/mL; 48 hours) |
|---|---|
| 1-methyl pseudo U (DNA2.0) | 153172 |
| 5-methoxy-uridine (CO3) | 366060 |
| 5-methoxy-uridine (CO7) | 190776 |
| 5-methoxy-uridine (CO9) | 119084 |

TABLE 18

Expression of GCSF in BJ Fibroblast cells (15 ng/well)

| Construct | GCSF expression in BJ (pg/mL; 48 hours) |
|---|---|
| 1-methyl pseudo U (DNA2.0) | 357902 |
| 5-methoxy-uridine (CO3) | 766241 |
| 5-methoxy-uridine (CO7) | 555814 |
| 5-methoxy-uridine (CO9) | 330441 |

Example 15. Cytokine Screen in BJ Fibroblast Cells

At 2 or 3 days prior to transfection, 100,000 BJ fibroblast cells (ATCC no. CRL-2522; Manassas, Va.) were harvested by treatment with trypsin-EDTA solution (LifeTechnologies, Grand Island, N.Y.) and seeded in a total volume of 500 ul EMEM medium (supplemented with 10% FCS and 10% Glutamax, both LifeTechnologies, Grand Island, N.Y.) per well in 24-well cell culture plates (Corning, Manassas, Va.). The cells were grown at 37° C. in a 5% $CO_2$ atmosphere overnight. On the next day, 500 ng modRNA, harboring chemical alterations on the bases or the ribose units, were diluted in 25 µL final volume of OPTI-MEM (LifeTechnologies, Grand Island, N.Y.). Lipofectamine 2000 (LifeTechnologies, Grand Island, N.Y.) was used as transfection reagent and 1.0 µL was diluted in 25 µL final volume of OPTI-MEM. After 5 min incubation at room temperature, both solutions were combined and incubated an additional 15 min at room temperature. The 50 µL were added to the 500 µL cell culture medium containing the BJ fibroblast cells. The plates were then incubated as described above.

After 18 h to 22 h incubation, cell culture supernatants were collected and centrifuged at 10,000 rcf for 2 min. The cleared supernatants were transferred and analyzed with a human IFN-beta ELISA (R&D Systems, Minneapolis, Minn.; Cat. #s 41410-2) and human CCL-5/RANTES ELISA (R&D Systems, Minneapolis, Minn.; Cat. #s SRNOOB) according to the manufacturer instructions. All samples were diluted until the determined values were within the linear range of the ELISA standard curves using a BioTek Synergy H1 µlate reader (BioTek, Winooski, Vt.). The results are shown in Tables 19, 20, and 21.

TABLE 19

INFβ expression in BJ Fibroblast cells by GCSF mRNA

| Construct | IFN-b expression in BJ (pg/mL; 48 hours) |
|---|---|
| 1-methyl pseudo U (DNA2.0) | 20 |
| 5-methoxy-uridine (CO3) | 0 |
| 5-methoxy-uridine (CO7) | 0 |
| 5-methoxy-uridine (CO9) | 0 |

TABLE 20

INFβ expression in BJ Fibroblast cells by FFLuc mRNA

| Construct | IFN-b expression in BJ (pg/mL; 48 hours) |
|---|---|
| 1-methyl pseudo U (CO7) | 194 |
| 5-methoxy-uridine (CO3) | 0 |
| 5-methoxy-uridine (CO7) | 0 |
| 5-methoxy-uridine (CO9) | 0 |

TABLE 21

INFβ expression in BJ Fibroblast cells by mCherry mRNA

| Construct | IFN-b expression in BJ (pg/mL; 48 hours) |
|---|---|
| 1-methyl pseudo U (CO7) | 309 |
| 5-methoxy-uridine (CO3) | 0 |
| 5-methoxy-uridine (CO7) | 0 |
| 5-methoxy-uridine (CO9) | 0 |

Example 16. In Vivo Expression of mRNA

Using the method described in Example 11, in vivo expression of the alternative mRNA of Example 12 was studied. Female CD-1 mice were administered the mRNAs intravenously at 0.05 mg/kg. The results are shown in Tables 22, 23, and 24.

TABLE 22

In vivo expression of GCSF

| Dose group (0.05 mg/kg) | GCSF @ 6 hours (ng/mL) |
|---|---|
| 1-methyl pseudo (WT) | 71.4 |
| 5-methoxy-uridine (CO3) | 32.5 |
| 5-methoxy-uridine (CO7) | 8.6 |
| 5-methoxy-uridine (CO9) | 30.7 |

TABLE 23

In vivo expression of Luciferase

| Dose group (0.05 mg/kg) | Total flux @ 6 hours (RLU) |
|---|---|
| 1-methyl pseudo (DNA2.0) | $2.38 \times 10^8$ |
| 1-methyl pseudo (CO7) | $1.40 \times 10^9$ |
| 5-methoxy-uridine (CO3) | $5.26 \times 10^8$ |
| 5-methoxy-uridine (CO7) | $1.86 \times 10^8$ |

TABLE 24

In vivo expression of GCSF

| Dose group (0.05 mg/kg) | GCSF @ 3 hours (ng/mL) | GCSF @ 6 hours (ng/mL) | GCSF @ 24 hours (ng/mL) |
|---|---|---|---|
| 1-methyl pseudoU (DNA2.0) | 409.6 | 546.0 | 168.2 |
| 1-methyl pseudoU (CO3) | 517.9 | 637.4 | 274.0 |
| 1-methyl pseudoU (CO7) | 355.8 | 473.5 | 220.2 |
| 1-methyl pseudoU (CO9) | 547.7 | 726.3 | 124.5 |
| 5-methoxy-uridine (CO3) | 234.1 | 277.8 | 64.6 |
| 5-methoxy-uridine (CO7) | 308.6 | 341.9 | 83.3 |
| 5-methoxy-uridine (CO9) | 253.9 | 285.3 | 51.9 |

Example 17. In Vivo Expression of mRNA in Non-Human Primates

Cynomolgus monkeys are administered a standard MC3 formulation including an mRNA encoding hEPO. The expression of hEPO was measured using an ELISA method before and 2, 6, 24, 48, 72, 96, and 120 hours after administration. Male monkeys were administered the formulation at a dose rate of 5 mL/kg/h for 1 hour.

TABLE 25

In vivo expression of hEPO

| Dose group (0.05 mg/kg) | hEPO Cmax (ng/mL) | AUC (hr*pg/mL) |
|---|---|---|
| 1-methyl pseudo (DNA2.0) | 70.0 | 954954 |
| 5-methoxy-uridine (CO9) | 50.6 | 984832 |

TABLE 26

In vivo expression of hEPO

| Dose group (0.05 mg/kg) | hEPO @ 6 hours (ng/mL) | hEPO @ 12 hours (ng/mL) | hEPO @ 24 hours (ng/mL) |
|---|---|---|---|
| 1-methyl pseudoU (DNA2.0) | 72.7 | 14.7 | 2.1 |
| 5-methoxy-uridine (CO9) | 87.1 | 62.6 | 18.9 |

Example 18. mRNA-Templated In Vitro Transcription

Human Epo 1-methylpseudouridine-containing mRNA was produced by run-off in vitro transcription using standard 4 h plasmid-based IVT reaction conditions. The material was subjected to reverse phase purification, and the INF-β clear fractions were pooled. From this pooled material, a standard 1-methylpseudouridine-containing and 5-methoxy-uridine-containing 4 h plasmid-based IVT reaction was run but in place of DNA template, INF-β clear mRNA was added to a final concentration of 1 mg/mL. After 4 h, the reaction was split in two, with part being used for LC analysis and part to be transfected into BJ fibroblasts using L-2000 according to the manufacturer suggested protocol. After 48 hours, the presence of INF-β was determined by ELISA. LC analysis showed the presence of n+1 polymers to be in much higher abundance in the samples incubated with 1-methylpseudouridine-containing nucleotides compared to 5-methoxy-uridine-containing nucleotides. Additionally, the 1-methylpseudouridine-containing sample showed significantly more INF-β response compared to the 5-methoxy-uridine-containing sample.

Example 19. In Vitro Transcription Temperature Dependence

Figure 3:
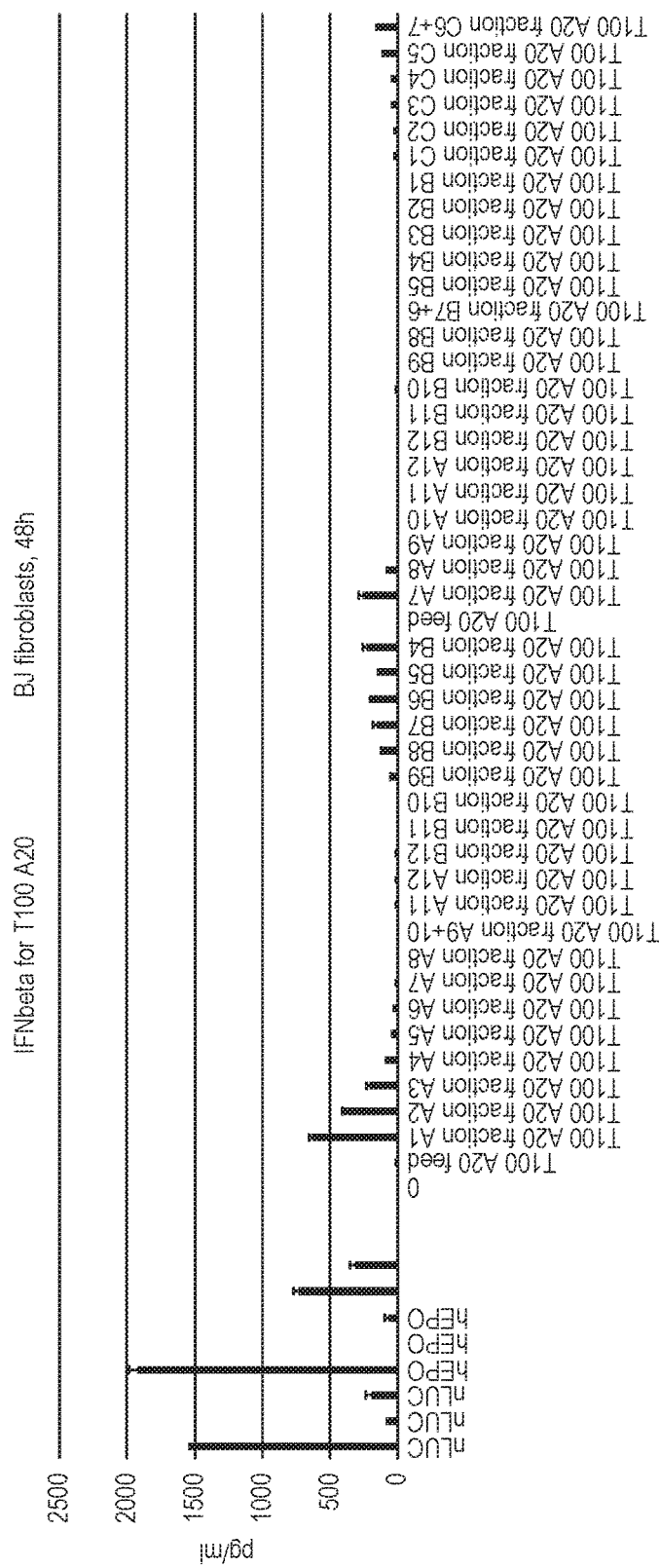
FIG. 3 is a graph of the induction of INFβ by mRNA produced by IVT at different temperatures.

Human Epo 1-methylpseudouridine-containing and 5-methoxy-uridine-containing mRNA was produced by run-off in vitro transcription using our standard 4 h plasmid-based IVT reaction conditions. The mRNA was split and part was subjected to oligo dT purification whereas the other part was crude reaction mixture. Both were transfected into BJ fibroblasts using L-2000, and INF-β levels were determined by ELISA. The dT purified and crude 5-methoxy-uridine-containing mRNA showed marginal INF-β whether the IVT was performed at 25° C. or 37° C., whereas the 1-methylpseudouridine-containing mRNA showed significant increases in INF-β induction at 25° C. compared to 37° C. The results are shown in FIG. 3.

Example 20. Production of mRNA with a 20 Consecutive Uridine Tail

Figure 4:
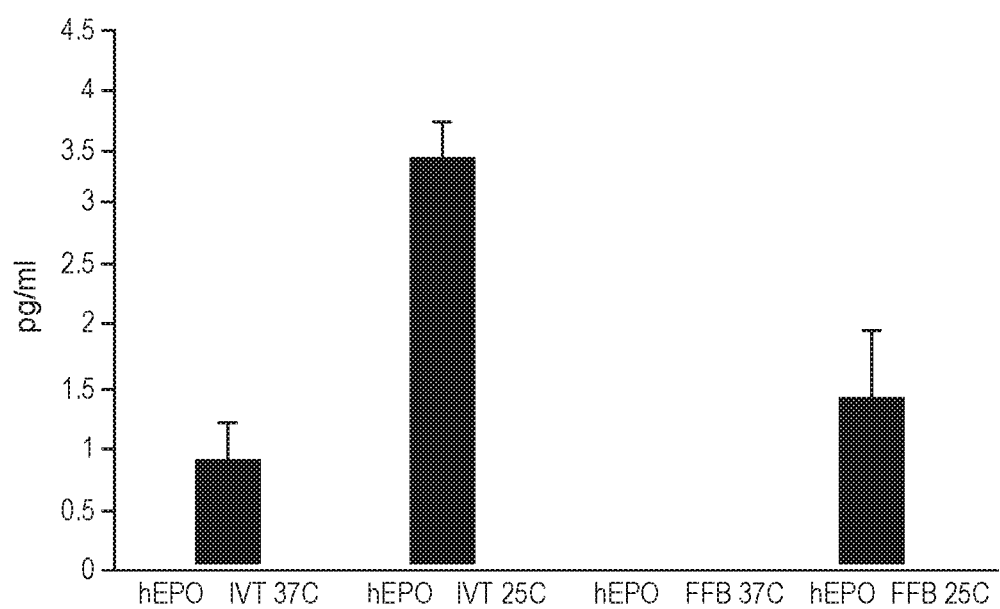
FIG. 4 is a graph of the induction of INFβ by mRNA with 3'-terminal poly-U feature.

A reverse PCR primer was designed to code for an mRNA with a tail structure of 100A20U-3'. PCR was completed as previously described, and run-off IVT was performed according to PCR-templated 4 h IVT conditions under either 1-methylpseudouridine-containing mRNA or 5-methoxy-uridine-containing mRNA conditions. The IVT was reverse-phase purified, the fractions were diafiltered into water, and transfected into BJ fibroblasts using L-2000. After 48 hours, INF-β levels were determined by ELISA. The results are shown in FIG. 4.

Other Embodiments

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

The invention claimed is:

1. A pharmaceutical composition comprising an mRNA encoding a polypeptide, and a pharmaceutically acceptable excipient, wherein the mRNA comprises:
   (i) a 5'-cap structure;
   (ii) a 5'-UTR;
   (iii) an open reading frame (ORF) encoding the polypeptide,
      wherein at least 95% of uracils in the ORF are 5-methoxyuracils; and
      wherein the uracil content in the ORF is between the theoretical minimum and 150% of the theoretical minimum,
   (iv) a 3'-UTR; and
   (v) a poly-A region;
      wherein the level of expression in a mammalian cell of the encoded polypeptide from the mRNA is increased relative to a reference mRNA comprising a reference open reading frame (rORF) encoding the polypeptide, wherein at least 95% of uracils in the rORF are 5-methoxyuracils, and wherein the uracil content in the rORF is from about 190% to about 200% of the theoretical minimum.

2. The pharmaceutical composition of claim 1, wherein the uracil content in the ORF is between the theoretical minimum and 125% of the theoretical minimum.

3. The pharmaceutical composition of claim 1, wherein the guanine content of the ORF is maximized for at least 50% of the codons, and wherein the ORF comprises at least one low frequency guanine maximized codon.

4. The pharmaceutical composition of claim 1, wherein the cytosine content of the ORF is maximized for at least 50% of the codons, and wherein the ORF comprises at least one low frequency cytosine maximized codon.

5. The pharmaceutical composition of claim 1, wherein the guanine and cytosine content of the ORF is maximized for at least 50% of the codons, and wherein the ORF comprises at least one low frequency guanine and cytosine maximized codon.

6. The pharmaceutical composition of claim 1, wherein the uracil content is less than 20% of the total nucleobase content in the ORF.

7. The pharmaceutical composition of claim 1, wherein the uracil content within any 20 nucleobase window within the ORF does not exceed 50%.

8. The pharmaceutical composition of claim 1, wherein the 5'-cap structure is cap0, cap1, or ARCA inosine, N1-methyl-guanosine, 2'-fluoro-guanosine, 7-deaza-guanosine, 8-oxo-guanosine, 2-amino-guanosine, LNA-guanosine, or 2-azido-guanosine.

9. The pharmaceutical composition of claim 1, wherein the 3'-UTR is an alpha-globin 3'-UTR.

10. The pharmaceutical composition of claim 1, wherein the poly-A region is between 80 to 120 nucleotides in length.

11. The pharmaceutical composition of claim 1, wherein, upon contacting a mammalian cell, the mRNA has a longer half-life, greater area under the curve of protein expression, or both, relative to a corresponding wild-type mRNA.

12. The pharmaceutical composition of claim 1, wherein the ORF further comprises at least one low-frequency codon.

13. The pharmaceutical composition of claim 1, wherein the 3'-UTR of the mRNA comprises at least one microRNA (miRNA) binding site.

14. The pharmaceutical composition of claim 13, wherein the miRNA is known to be expressed in liver cells or in immune cells.

15. The pharmaceutical composition of claim 14, wherein the miRNA is chosen from miR-142-5p, miR-146-5p, or miR-146-3p.

16. The pharmaceutical composition of claim 14, wherein the miRNA is miR-142-3p.

17. The pharmaceutical composition of claim 13, wherein the miRNA is known to be expressed in liver cells, and is miR-122-5p or miR-122-3p.

18. The pharmaceutical composition of claim 1, wherein the composition is in a single-unit dosage form.

19. The pharmaceutical composition of claim 1, wherein the composition is in a multi-unit dosage form.

20. The pharmaceutical composition of claim 1, wherein the mRNA is purified.

21. The pharmaceutical composition of claim 20, wherein the mRNA is purified without reverse phase chromatography.

* * * * *